(12) United States Patent  (10) Patent No.: US 9,290,515 B2
Yamawaki et al.  (45) Date of Patent: Mar. 22, 2016

(54) CEPHEM DERIVATIVE HAVING CATECHOL GROUP

(71) Applicant: SHIONOGI & CO., LTD., Osaka-shi, Osaka (JP)

(72) Inventors: Kenji Yamawaki, Toyonaka (JP); Masayuki Sano, Toyonaka (JP); Jun Sato, Toyonaka (JP)

(73) Assignee: SHIONOGI & CO., LTD, Osaka (JP)

( * ) Notice: Subject to any disclaimer, the term of this patent is extended or adjusted under 35 U.S.C. 154(b) by 22 days.

(21) Appl. No.: 14/349,227

(22) PCT Filed: Oct. 3, 2012

(86) PCT No.: PCT/JP2012/075625
§ 371 (c)(1),
(2) Date: Apr. 2, 2014

(87) PCT Pub. No.: WO2013/051597
PCT Pub. Date: Apr. 11, 2013

(65) Prior Publication Data
US 2014/0256697 A1    Sep. 11, 2014

(30) Foreign Application Priority Data

Oct. 4, 2011  (JP) .................................. 2011-220058

(51) Int. Cl.
*C07D 501/56* (2006.01)
*C07D 501/46* (2006.01)

(52) U.S. Cl.
CPC ............ *C07D 501/56* (2013.01); *C07D 501/46* (2013.01)

(58) Field of Classification Search
None
See application file for complete search history.

(56) References Cited

U.S. PATENT DOCUMENTS

| | | | |
|---|---|---|---|
| 4,406,899 | A | 9/1983 | Aburaki et al. |
| 4,647,556 | A | 3/1987 | Lattrell et al. |
| 5,095,012 | A | 3/1992 | Okita et al. |
| 2005/0153950 | A1 | 7/2005 | Nishitani et al. |

(Continued)

FOREIGN PATENT DOCUMENTS

| | | |
|---|---|---|
| AU | 676218 | 3/1997 |
| EP | 0 172 919 | 3/1986 |

(Continued)

OTHER PUBLICATIONS

CAPLUS printout of Japanese patent No. JP01175982.*

(Continued)

*Primary Examiner* — Rebecca Anderson
*Assistant Examiner* — Po-Chih Chen
(74) *Attorney, Agent, or Firm* — Hamre, Schumann, Mueller & Larson, P.C.

(57) ABSTRACT

A compound represented by formula (I) or a pharmaceutically acceptable salt thereof wherein A represents a group represented by one of formulae (i)-(iii); B represents a group represented by formula (v) or (vi); and E represents a substituted or unsubstituted heterocyclic group having a cationic nitrogen atom.

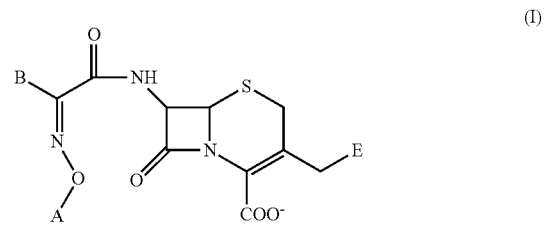

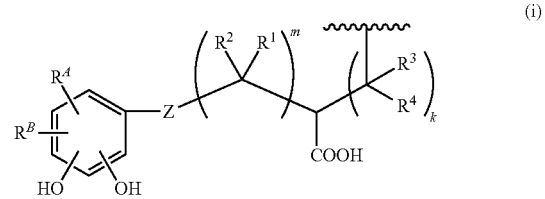

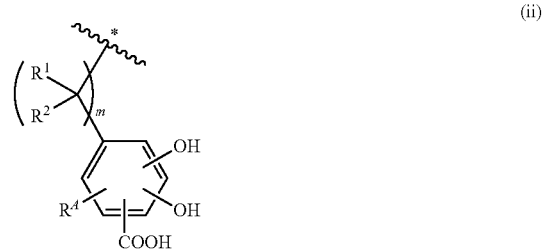

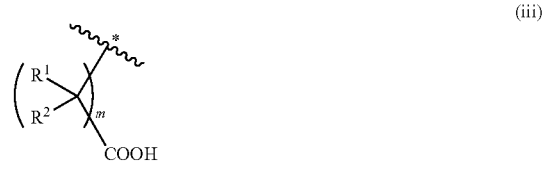

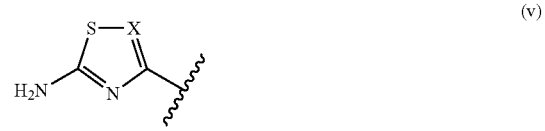

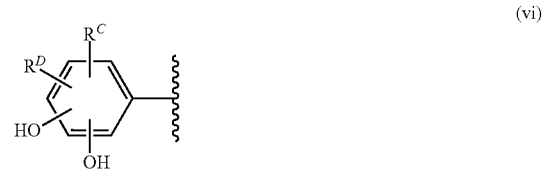

8 Claims, No Drawings

(56) References Cited

U.S. PATENT DOCUMENTS

| | | |
|---|---|---|
| 2009/0131655 A1 | 5/2009 | Nishitani et al. |
| 2011/0190254 A1 | 8/2011 | Nishitani et al. |
| 2013/0079319 A1 | 3/2013 | Yamawaki et al. |
| 2013/0102583 A1 | 4/2013 | Hisakawa et al. |

FOREIGN PATENT DOCUMENTS

| | | |
|---|---|---|
| EP | 0 303 172 | 2/1989 |
| EP | 0 345 671 | 12/1989 |
| EP | 0 416 410 | 3/1991 |
| JP | 60-197693 | 10/1985 |
| JP | 62-270589 | 11/1987 |
| JP | 1-175982 | 7/1989 |
| JP | 2-15090 | 1/1990 |
| JP | 2-28185 | 1/1990 |
| JP | 2-117678 | 5/1990 |
| JP | 2-221283 | 9/1990 |
| JP | 4-112891 | 4/1992 |
| JP | 5-213971 | 8/1993 |
| WO | WO 86/05786 | 10/1986 |
| WO | WO 86/05789 | 10/1986 |
| WO | WO 92/21683 | 12/1992 |
| WO | WO 2007/096740 | 8/2007 |
| WO | WO 2007/119511 | 10/2007 |

OTHER PUBLICATIONS

Takeda et al. *Journal of Antibiotics*, vol. 61, No. 1, pp. 36-39 (2008).
Hashizume et al. *Journal of Antibiotics*, vol .43, No. 12, pp. 1617-1620 (1990).
Weissberger et al. *Journal of Antibiotics*, vol. 42, No. 5, pp. 795-806 (1989).
Okita et al. *Journal of Antibiotics*, vol. 46, No. 5, pp. 833-839 (1993).
Imae et al. *Journal of Antibiotics*, vol. 46, pp. 840-849 (1993).
Imura et al. *Journal of Antibiotics*, vol. 46, pp. 850-857 (1993).
Baudart et al. *Journal of Antibiotics*, vol. 46, pp. 1458-1470 (1993).
Choi et al. *Journal of Antibiotics*, vol. 48, No. 11, pp. 1371-1374 (1995).
Arnould et al. *Journal of Medicinal Chemistry*, vol. 35, pp. 2631-2642 (1992).
Bird et al. *Journal of Medicinal Chemistry*, vol. 35, pp. 2643-2651 (1992).
Tsuji et al. *Bioorganic and Medicinal Chemistry Letters*, vol. 5, No. 9, pp. 963-966 (1995).
Adams et al. *Journal of Antibiotics*, vol. 48, No. 5, pp. 417-424 (1995).
Mochizuki et al. *Journal of Antibiotics*, vol. 41, No. 3, pp. 377-391 (1988).
Kim et al. *Journal of Antibiotics*, vol. 49, pp. 496-498 (1996).
Guest et al. *Journal of Antibiotics*, vol. 46, No. 8, pp. 1279-1288 (1993).
Yamano et al. *Applied Microbiology and Biotechnology*, vol. 40, pp. 892-897 (1994).

\* cited by examiner

CEPHEM DERIVATIVE HAVING CATECHOL GROUP

TECHNICAL FIELD

The invention is related to cephem compounds, which have a wide antimicrobial spectrum, and in particular exhibit potent antimicrobial activity against beta-lactamase producing Gram negative bacteria, and pharmaceutical composition comprising the same.

BACKGROUND ART

To date, a variety of beta-lactam drugs have been developed and beta-lactam drugs have become clinically extremely important antimicrobial drugs. However, there are increasing number of bacterial types which have obtained resistancy against beta-lactam drugs by producing beta-lactamase, which degrade beta-lactam drugs.

According to the Ambler molecular classification, beta-lactamase are largely classified into four classes. Specifically, those are Class A (TEM type, SHV type, CTX-M type and the like), Class B (IMP type, VIM type, L-1 type and the like), Class C (AmpC type) and Class D (OXA type and the like). Amongst these, Classes A, C and D types are largely classified into serine-beta-lactamase, and on the other hand, Class B type is classified into metallo-beta-lactamase. It has been known that both have respectively different mechanisms to each other in terms of hydrolysis of beta-lactam drugs.

Recently, clinical problem has been occurring due to the existence of Gram negative bacteria which have become highly resistant to beta-lactam drugs including Cephems and Carbapenems by production of Class A (ESBL) or D types serine-beta-lactamase and Class B type metallo-beta-lactamase which have extended their substrate spectrum. Particularly, metallo-beta-lactamase is known to be one of the causes of obtaining multi-resistancy in Gram negative bacteria. Cephem compounds which exhibit intermediate activity against metallo-beta-lactamase producing Gram negative bacteria are known (e.g., Patent Document 1 and Non-Patent Document 1). However, there is a demand for development of Cephem compounds which exhibit more potent antimicrobial activity, in particular effectivity against a variety of beta-lactamase producing Gram negative bacteria.

One of the known antimicrobials having high anti-Gram negative bactericidal activity is Cephem compounds having a catechol group intramolecularly (e.g., Non-Patent Documents 2-4). The action thereof is that the catechol group forms a chelate with $Fe^{3+}$, thereby the compound 1s efficiently incorporated into the bacterial body by means of $Fe^{3+}$ transportation system on the cellular membrane (tonB-dependent iron transport system). Therefore, research has been conducted on compounds having catechol or similar structure thereto, on the 3-side chain or 7-side chain on the Cephem backbone.

Patent Documents 2-8 and Non-patent Documents 2-11 and 16 disclose compounds having a catechol or a structure similar thereto on the 3-side chain of the Cephem backbone.

Patent Documents 9 and 12-14, and Non-patent Documents 12-15 disclose compounds having a catechol or a structure similar thereto on the 7-side chain of the Cephem backbone.

Non-patent Documents 7, 9, 10 and 12-15 describe Cephem compounds which have been stabilized against beta-lactamase.

However, these documents do not disclose the compounds of the subject invention. Furthermore, these documents, which describe Cephem compounds having catechol group intramolecularly, have no specific description regarding metallo-beta-lactamase of Class B type, or antibacterial activity against wide spectrum of Gram negative bacteria including Class B type.

Patent Documents 10 and 11 do not specifically disclose Cephem compounds having catechol type substituents. However, the present applicant filed an application of Cephem compounds having catechol type substituents (Patent Documents 12-14).

PRIOR ART DOCUMENT

Patent Document

[Patent Document 1] International Publication No. 2007/119511 pamphlet
[Patent Document 2] Japanese Laid-Open Publication No. 3-173893
[Patent Document 3] Japanese Laid-Open Publication No. 2-15090
[Patent Document 4] Japanese Laid-Open Publication No. 2-28187
[Patent Document 5] Japanese Laid-Open Publication No. 2-117678
[Patent Document 6] Japanese PCT National Phase Laid-Open Publication No. 6-510523
[Patent Document 7] Japanese Laid-Open Publication No. 5-213971
[Patent Document 8] Japanese Laid-Open Publication No. 2-28185
[Patent Document 9] Japanese Laid-Open Publication No. 6-345776
[Patent Document 10] International Publication No. 2007/096740 pamphlet
[Patent Document 11] International Publication No. 2003/078440 pamphlet
[Patent Document 12] International Publication No. 2010/050468
[Patent Document 13] International Patent Application No. PCT/JP2011/058497
[Patent Document 14] International Patent Application No. PCT/JP2011/058498
[Patent Document 15] European Patent Publication No. 472060A
[Patent Document 16] Japanese Laid-Open Publication No. S62-270589
[Patent Document 17] International Publication No. 1986/005789 pamphlet Non-Patent Document

[Non-patent document 1] The Journal of Antibiotics, vol. 61, pp. 36-39 (2008)
[Non-patent document 2] The Journal of Antibiotics, vol. 43, pp. 1617-1620 (1990)
[Non-patent document 3] The Journal of Antibiotics, vol. 42, pp. 795-806 (1989)
[Non-patent document 4] The Journal of Antibiotics, vol. 46, pp. 833-839 (1993)
[Non-patent document 5] The Journal of Antibiotics, vol. 46, pp. 840-849 (1993)
[Non-patent document 6] The Journal of Antibiotics, vol. 46, pp. 850-857 (1993)
[Non-patent document 7] The Journal of Antibiotics, vol. 46, pp. 1458-1470 (1993)

[Non-patent document 8] The Journal of Antibiotics, vol. 48, pp. 1371-1374 (1995)
[Non-patent document 9] The Journal of Medicinal Chemistry, vol. 35, pp. 2631-2642 (1992)
[Non-patent document 10] The Journal of Medicinal Chemistry, vol. 35, pp. 2643-2651 (1992)
[Non-patent document 11] Bioorganic & Medicinal Chemistry Letters, vol. 5, pp. 963-966 (1995)
[Non-patent document 12] The Journal of Antibiotics, vol. 48, pp. 417-424 (1995)
[Non-patent document 13] The Journal of Antibiotics, vol. 41, pp. 377-391 (1988)
[Non-patent document 14] The Journal of Antibiotics, vol. 49, pp. 496-498 (1996)
[Non-patent document 15] The Journal of Antibiotics, vol. 46, pp. 1279-1288 (1993)
[Non-patent document 16] Applied Microbiology and Biotechnology, vol. 40, pp. 892-897 (1994)

SUMMARY OF INVENTION

Problems to be Solved by the Invention

The subject invention provides Cephem compounds which exhibit potent antimicrobial spectrum against a variety of bacteria including Gram negative bacteria and/or Gram positive bacteria.

Preferably, the subject invention provides Cephem compounds which exhibit potent antimicrobial activity against beta-lactamase producing Gram negative bacteria.

More preferably, the subject invention provides Cephem compounds which exhibit potent antimicrobial activity against multi-drug resistant microbials, in particular, Class B type metallo-beta-lactamase producing Gram negative bacteria.

Still preferably, the subject invention provides Cephem compounds which exhibit effective antimicrobial activity against extended-spectrum beta-lactamase (ESBL) producing bacteria.

Most preferably, the subject invention provides Cephem compounds which do not exhibit cross-resistance against known Cephem drug or Carbapenem drugs.

Means for Solving the Problems

The subject invention provides Cephem compounds which have solved the above-mentioned problems having at least following structural features:
1) The compound of the subject invention has a heterocyclic group (E) having a cationic nitrogen atom on the 3-side chain.
2) The compound of the subject invention has a catechol-type substituent at the end of the oxime moiety (A) on the 7-side chain. Preferably, the compound has one or two chlorine atom(s) or fluorine atom(s) on the benzene ring of the catechol group. More preferably, the compound has one chlorine atom or fluorine atom. Particularly preferably, the compound has one chlorine atom.
2) The compound of the subject invention has a spacer part between the oxime moiety of the 7-side chain and the catechol-type substituent.
3) The spacer part has a group represented by Z, which is —C(=O)—N(—R$^5$)—, —N(—R$^5$)—C(=O)—, —S(=O)$_2$—N(—R$^5$)— or —N(—R$^5$)—S(=O)$_2$— wherein R$^5$ is a hydrogen atom or an alkyl group.
4) The compound of the subject invention has an aminothiadiazole-type ring, an aminothiazole-type ring or a catechol-type ring (B) on the 7-side chain, and has a carboxyl group on an end of an oxime moiety (A).

Specifically, the subject invention provides the following inventions:
(Item 1)
A compound of formula (I):

[Formula 1]

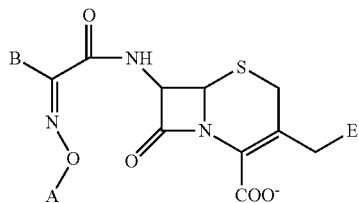

wherein,
A is a group of any one of the following formula (i) to (iii):

[Formula 2]

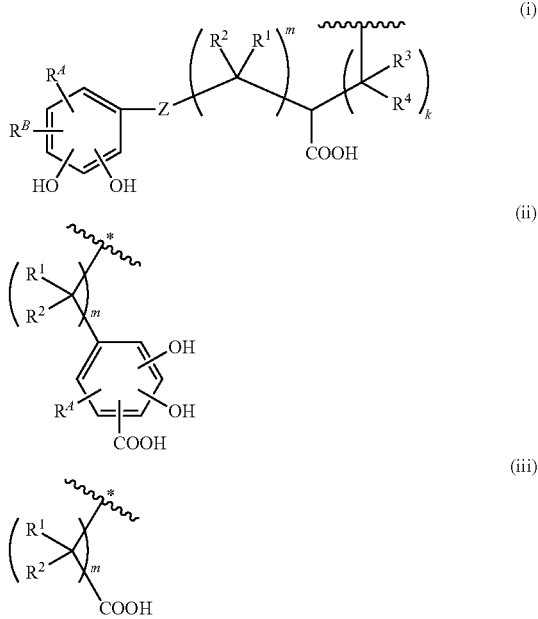

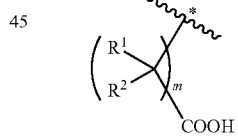

wherein, m and k are each independently an integer of 0 to 3;
Z is —C(=O)—N(—R$^5$)—, —N(—R$^5$)—C(=O)—, —S(=O)$_2$—N(—R$^5$)—, or —N(—R$^5$)—S(=O)$_2$—;
R$^1$ is each independently hydrogen atom, alkyl, carboxy, or haloalkyl;
R$^2$ is each independently hydrogen atom, alkyl, carboxy, or haloalkyl;
R$^3$ is each independently hydrogen atom, alkyl, or haloalkyl;
R$^4$ is each independently hydrogen atom, alkyl, or haloalkyl;
R$^1$ and R$^2$, and R$^3$ and R$^4$ taken together with a neighboring atom may form substituted or unsubstituted carbocyclic group, or substituted or unsubstituted heterocyclic group;
R$^5$ is hydrogen atom, or alkyl
R$^A$ and R$^B$ are each independently hydrogen atom, halogen atom, hydroxyl, carboxyl, alkyl, or haloalkyl;

B is a group of the following formula (v) or (vi):

[Formula 3]

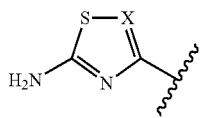
(v)

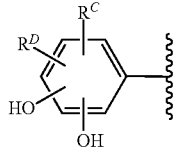
(vi)

wherein, X is —CH=, —C(—Cl)=, or —N=,
R$^C$ and R$^D$ are each independently hydrogen atom, halogen atom, hydroxyl, amino, alkyl, or haloalkyl;
E is a substituted or unsubstituted heterocyclic group having a cationic nitrogen atom,
provided that when A is formula (iii), B is formula (vi), or a pharmaceutically acceptable salt thereof.

(Item 2)

The compound or a pharmaceutically acceptable salt thereof according to Item 1,
wherein, E is selected from the following formula (1) to (40)

[Formula 4]

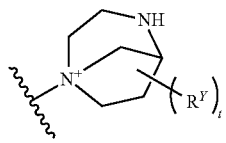
(1)

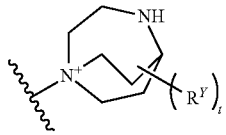
(2)

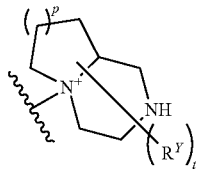
(3)

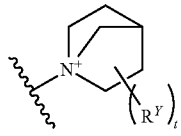
(4)

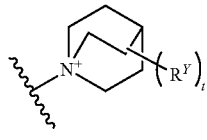
(5)

-continued

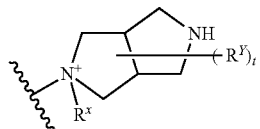
(6)

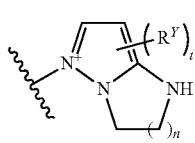
(7)

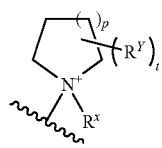
(8)

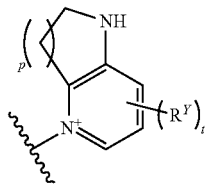
(9)

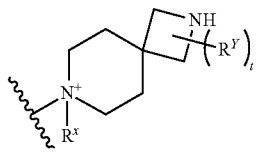
(10)

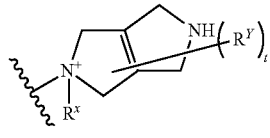
(11)

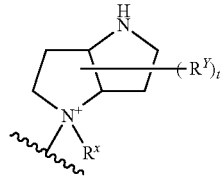
(12)

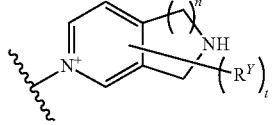
(13)

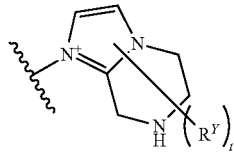
(14)

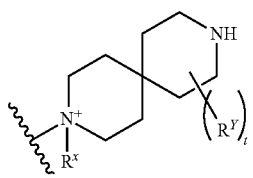
(15)
[Formula 5]
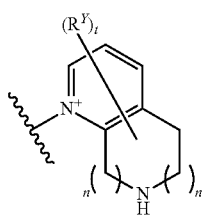
(16)
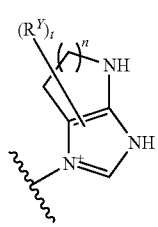
(17)
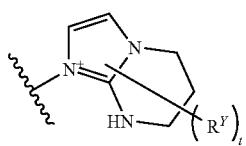
(18)
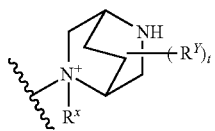
(19)
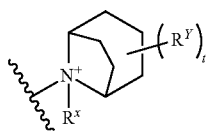
(20)
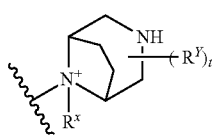
(21)
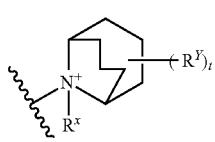
(22)
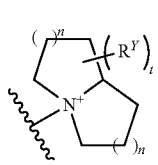
(23)
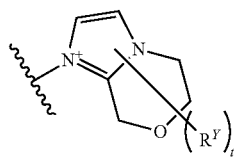
(24)
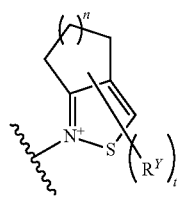
(25)
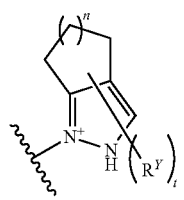
(26)
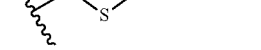
(27)
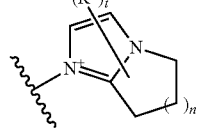
(28)
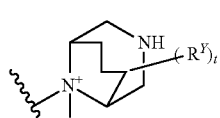
(29)
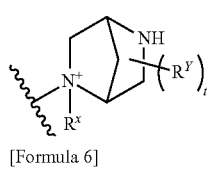
(30)
[Formula 6]
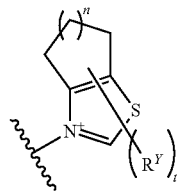
(31)
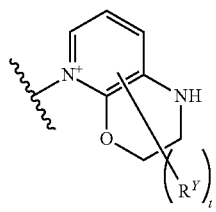
(32)

-continued

(33) 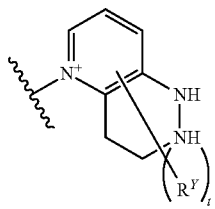

(34) 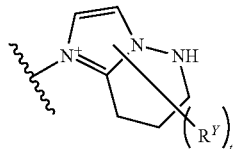

(35) 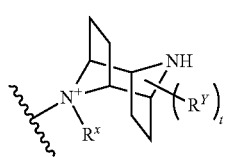

(36) 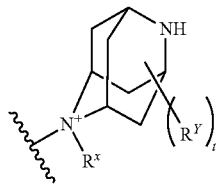

(37) 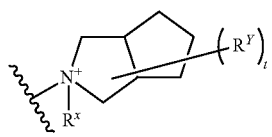

(38) 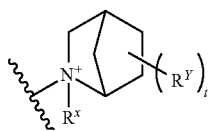

(39) 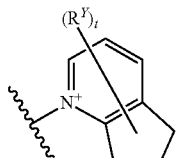

(40) 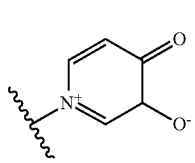

wherein,
$R^X$ is substituted or unsubstituted alkyl,
$R^Y$ is amino, hydroxyl, substituted or unsubstituted alkyl,
P is an integer of 1 to 3, n is an integer of 1 or 2, and t is an integer of 0 to 3.

(Item 3)
The compound, or a pharmaceutically acceptable salt thereof according to Item 2, wherein E is a group of formula (5), (8), (20), (23), (39), or (40).

(Item 4)
The compound, or a pharmaceutically acceptable salt thereof according to Item 2 or 3, wherein t is 0 or 1.

(Item 5)
The compound, or a pharmaceutically acceptable salt thereof according to any one of Items 1 to 4, wherein the formulae (i) and (ii) are a group of the following formula (ia) or (ib), and a group of formula (iia), respectively:

[Formula 7]

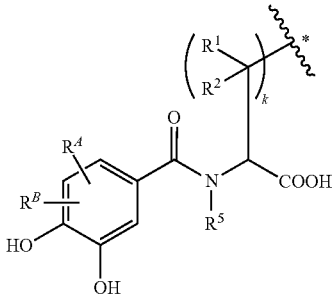
(ia)

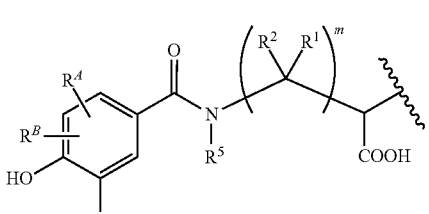
(ib)

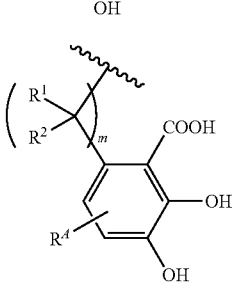
(iia)

wherein each symbol is the same as defined in Item 1.

(Item 6)
The compound, or a pharmaceutically acceptable salt thereof according to any one of Items 1 to 5,
wherein,
$R^1$ is each independently hydrogen atom, alkyl, or carboxy;
$R^2$ is each independently hydrogen atom, alkyl, or carboxy;
$R^3$ is each independently hydrogen atom or alkyl;
$R^4$ is each independently hydrogen atom or alkyl; and
$R^5$ is hydrogen atom or alkyl.

(Item 7)
The compound, or a pharmaceutically acceptable salt thereof according to any one of Items 1 to 6, wherein, $R^A$ and $R^B$ are each independently hydrogen atom, halogen atom or carboxy.

(Item 8)
The compound, or a pharmaceutically acceptable salt thereof according to any one of Items 1 to 7, wherein B is a group of formula (v).

(Item 9)
A pharmaceutical composition, comprising the compound or the pharmaceutically acceptable salt thereof according to any one of Items 1 to 8.

(Item 9')
A pharmaceutical composition according to Item 9 which has an antimacrobial activity.
(Item 10)
A method for treating an infectious disease, characterized in that the compound or the pharmaceutically acceptable salt thereof according to any one of items 1 to 8 is administered.
(Item 11)
The compound, or the pharmaceutically acceptable salt thereof according to any one of items 1 to 8 for the treatment of an infectious disease.
(Item 12)
Use of the compound, or the pharmaceutically acceptable salt thereof according to any one of items 1 to 8, for manufacturing an infectious disease therapeutic agent.

Effects of the Invention

The compounds of the subject invention are useful as a pharmaceutical product in that the compounds having at least one of the following features:
1) The compound exhibits broad antimicrobial spectrum against a variety of bacteria including Gram negative bacteria;
2) The compounds exhibit potent antimicrobial activity against beta-lactamase producing Gram negative bacteria;
3) The compounds exhibit potent antimicrobial activity against multi drug resistant bacteria and multi drug resistant pseudomonas, in particular, Class B type, metallo-beta-lactamase producing Gram negative bacteria;
4) The compounds exhibit potent antimicrobial activity against extended-spectrum beta-lactamase (ESBL) producing bacteria;
5) The compounds do not exhibit cross resistance with known Cephem drugs and/or Carbapenem drugs; and
6) The compounds do not exhibit side effects such as fever after administration into the body.
7) The compounds are highly soluble in water and suitable for parenteral injection.

EMBODIMENTS FOR CARRYING OUT THE INVENTION

The respective terms used herein are as defined alone or in combination with other terms as follows:
"Halogen" includes fluorine, chlorine, bromine and iodine. Preferable are fluorine, chlorine, and bromine, further preferable are fluorine, and chlorine, particularly preferable is chlorine.
"Alkyl" includes straight or branched alkyls of a carbon number of 1 to 8, preferably 1 to 6, further preferably 1 to 4, and examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, etc.
"Haloalkyl" is a group in which an arbitrary position of the "alkyl" is substituted with one or more of the "halogen", and examples include monofluoromethyl, difluoromethyl, trifluoromethyl, monochloromethyl, dichloromethyl, trichloromethyl, monobromomethyl, monofluoroethyl, monochloroethyl, chlorodifluoromethyl, etc. Preferable are trifluoromethyl, and trichloromethyl.
Examples of the substituent of "substituted or unsubstituted alkyl" include same or different one or more group(s), preferably 1 to 3 group(s) selected from a substituent group Alpha.
Herein, the "substituent group Alpha" is a group consisting of halogen, hydroxy, alkyloxy, hydroxyalkyloxy, alkyloxyalkyloxy, carboxy, amino, acylamino, alkylamino, imino, hydroxyimino, alkyloxyimino, alkylthio, carbamoyl, alkylcarbamoyl, hydroxyalkylcarbamoyl, sulfamoyl, alkylsulfamoyl, alkylsulfinyl, cyano, nitro, carbocyclic group and heterocyclic group.
An alkyl moiety in "alkyloxy", "hydroxyalkyloxy", "alkyloxyalkyloxy", "alkylamino", "alkyloxyimino", "alkylthio", "alkylcarbamoyl", "hydroxyalkylcarbamoyl", "alkylsulfamoyl", "alkylsulfinyl" has the same meaning as the "alkyl".
Examples of a preferable embodiment of the substituent in "substituted or unsubstituted alkyl" include fluorine atom, chlorine atom, bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, alkylsulfamoyl, cyano, nitro, phenyl, cyclopropyl, cyclobutyl, cyclohexyl, pyridyl, morpholinyl, etc.
Examples of a preferable embodiment of "substituted or unsubstituted alkyl" include methyl, ethyl, isopropyl, tert-butyl, monofluoromethyl, difluoromethyl, trifluoromethyl, carboxymethyl, carboxyethyl, carbamoylmethyl, carbamoylethyl, hydroxymethyl, hydroxyethyl, methoxymethyl, ethoxymethyl, methoxyethyl, ethoxyethyl, methylthiomethyl, ethylthiomethyl, benzyl, 4-hydroxybenzyl, 4-methoxybenzyl, 4-carboxybenzyl, aminoethyl, and

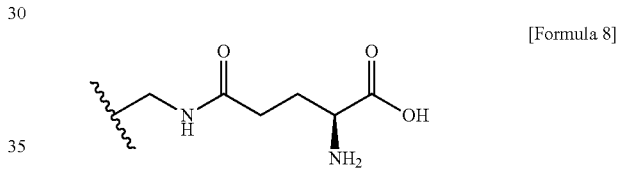

[Formula 8]

etc.
"Carbocyclic group" includes cycloalkyl, cycloalkenyl, aryl and non-aromatic fused carbocyclic group, etc. All of them include the above-mentioned monovalent groups, but also the above-mentioned divalent groups (cycloalkylene, cycloalkenylene, arylene).
"Cycloalkyl" is a carbocyclic group of a carbon number of 3 to 10, preferably a carbon number of 3 to 8, more preferably a carbon number of 4 to 8, and examples include cyclopropyl, cyclobutyl, cyclopentyl, cyclohexyl, cycloheptyl, cyclooctyl, cyclononyl and cyclodecyl, etc.
"Cycloalkenyl" includes the above-mentioned cycloalkyls which have one or more double bond(s) at an arbitrary position in a ring and, specifically, examples include cyclopropenyl, cyclobutenyl, cyclopentenyl, cyclohexenyl, cycloheptynyl, cyclooctynyl and cyclohexadienyl, etc.
"Aryl" includes phenyl, naphthyl, anthryl and phenanthryl, etc. and, particularly, phenyl is preferable.
"Non-aromatic fused carbocyclic group" includes groups in which two or more cyclic groups selected from the above-mentioned "cycloalkyl", "cycloalkenyl" and "aryl" are fused and, specifically, examples include indanyl, indenyl, tetrahydronaphthyl and fluorenyl, etc.
"Heterocyclic group" includes heterocyclic groups having one or more hetero atom(s) arbitrarily selected from O, S and N in a ring and, specifically, examples include 5- to 6-membered heteroaryls such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl and thienyl, etc.;

bicyclic fused heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, pyrazolopyridine, triazolopyridyl, imidazothiazolyl, pyrazinopyridazinyl, quinazolinyl, quinolyl, isoquinolyl, naphthyridinyl, dihydrobenzofuryl, tetrahydroquinolyl, tetrahydroisoquinolyl, dihydrobenzoxazine, tetrahydrobenzothienyl, etc.;

tricyclic fused heterocyclic groups such as carbazolyl, acridinyl, xanthenyl, phenothiazinyl, phenoxathiinyl, phenoxazinyl, dibenzofuryl, imidazoquinolyl, etc.;

non-aromatic heterocyclic groups such as dioxanyl, thiiranyl, oxiranyl, oxathiolanyl, azetidinyl, thianyl, thiazolidine, pyrrolidinyl, pyrrolinyl, imidazolidinyl, imidazolinyl, pyrazolidinyl, pyrazolinyl, piperidyl, piperazinyl, morpholinyl, thiomorpholinyl, thiomorpholino, dihydropyridyl, dihydrobenzimidazolyl, tetrahydropyridyl, tetrahydrofuryl, tetrahydropyranyl, tetrahydrothiazolyl, tetrahydroisothiazolyl, dihydrooxazinyl, hexahydroazepinyl, tetrahydrodiazepinyl, etc. Preferable is a 5- to 6-membered heteroaryl or a non-aromatic heterocyclic group.

More preferable is 5- to 6-membered heteroaryl.

Examples of the substituent of "substituted or unsubstituted carbocyclic group", and "substituted or unsubstituted heterocyclic group" include substituted or unsubstituted alkyl, and one or more group(s) selected from a substituent group Alpha.

Examples of a preferable embodiment of the substituent in "substituted or unsubstituted carbocyclic group", and "substituted or unsubstituted heterocyclic group" include methyl, ethylisopropyl, tert-butyl, fluorine atom, chlorine atom, bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, etc.

Examples of "5-membered heterocyclic group" include pyrrolidine, pyrazolidine, imidazolidine, tetrahydrofuran, tetrahydrothiophene, furan, pyrrole, oxazole, oxadiazole, isoxazole, etc.

Examples of "$R^1$ and $R^2$, and $R^3$ and $R^4$ taken together with a neighboring atom may form a substituted or unsubstituted carbocyclic group, or a substituted or unsubstituted heterocyclic group" include the cases in which

[Formula 9]

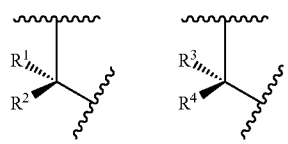

wherein each symbol is as defined in the item 1,
is cycloalkyl, cycloalkenyl, or a non-aromatic heterocyclic group optionally having a group selected from a substituent group Alpha on the ring, and examples include the following formulae:

[Formula 10]

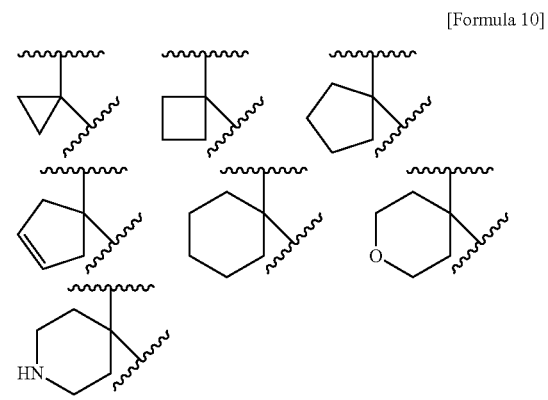

optionally having a group selected from a substituent group Alpha on a ring.

"Heterocyclic group having a substituted or unsubstituted cationic nitrogen atom" of "E" is a heterocyclic group having one or more, preferably one, +1 valent quaternary nitrogen atom(s) ($N^+$), as an atom constituting the heterocycle.

"Heterocyclic group having a substituted or unsubstituted cationic nitrogen atom" of "E" includes heterocyclic groups in which a hydrogen atom on a carbon atom and/or a nitrogen atom of each cyclic group is replaced with substituted or unsubstituted alkyl, or same or different one or more group(s) selected from a substituent group Alpha. Examples of a preferable embodiment of the substituent include methyl, ethylisopropyl, tert-butyl, fluorine atom, chlorine atom, bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, alkylsulfamoyl, cyano, nitro, phenyl, cyclopropyl, cyclobutyl, cyclohexyl, pyridyl, morpholinyl, etc. A more preferable embodiment is unsubstituted.

A carboxyl group and/or a hydroxyl group possessed by the compound of the subject invention also includes those groups in which a hydrogen ion is eliminated into the anion state (—$COO^-$ group and/or —$O^-$ group).

An amino group possessed by the compound of the subject invention also includes amino groups to which a hydrogen ion is bound into the ammonium salt state (—$NH_3^+$ group).

Preferable embodiments of each variable in the formula (I) are shown below, but the scope of the subject invention is not limited to those described below.

Examples of a preferable embodiment of "A" include the formula (i):

[Formula 11]

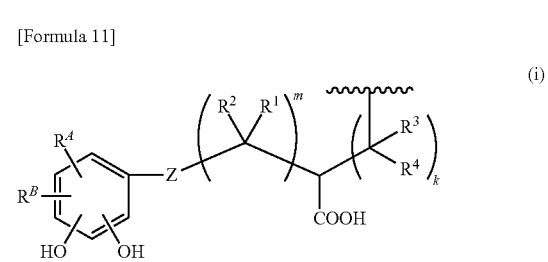

wherein each symbol is as defined in the Item 1.

Examples of a more preferable embodiment of "A" include the formula (ia) and formula (ib):

[Formula 12]

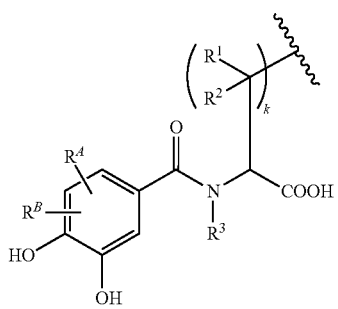

(ia)

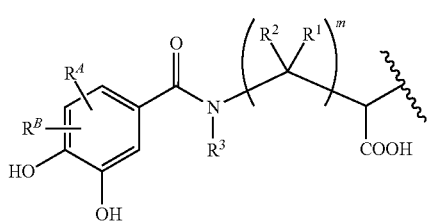

(ib)

wherein each symbol is as defined in the Item 1.

Herewith, the compounds exhibit potent antimacrobial activity against multi drug resistant bacteria and highly-resistant bacteria of a variety of Gram-negative bacterium.

Examples of a preferable embodiment of "B" include the formula (v):

[Formula 13]

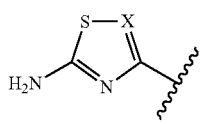

(v)

wherein each symbol is as defined in the Item 1.

Examples of a more preferable embodiment of "B" include the following formulae:

[Formula 14]

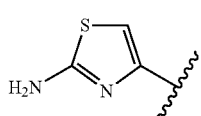 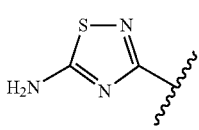

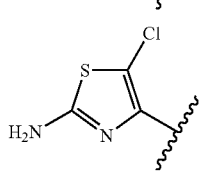

Examples of a preferable embodiment of "Z" include —C(=O)—NH—, —NH—C(=O)—, —S(=O)$_2$—NH—, or —NH—S(=O)$_2$—.

Examples of "R$^1$", "R$^2$", "R$^3$" and "R$^4$" include a hydrogen atom, fluorine atom, chlorine atom, methyl, ethyl, isopropyl, tert-butyl, monofluoromethyl, difluoromethyl, trifluoromethyl, etc.

Examples of a preferable combination of (R$^1$, R$^2$) and (R$^3$, R$^4$) include (hydrogen atom, hydrogen atom), (methyl, hydrogen atom), (hydrogen atom, methyl), (methyl, methyl), (ethyl, hydrogen atom), (hydrogen atom, ethyl), (ethyl, ethyl), etc. A more preferable combination is (hydrogen atom, hydrogen atom), or (methyl, methyl).

Examples of a preferable embodiment of the case where "R$^1$ and R$^2$, and R$^3$ and R$^4$ taken together with a neighboring atom may form a substituted or unsubstituted carbocyclic group, or a substituted or unsubstituted heterocyclic group" include substituted or unsubstituted 3- to 8-membered cycloalkyl, substituted or unsubstituted 3- to 8-membered cycloalkenyl, or a substituted or unsubstituted 3- to 8-membered non-aromatic heterocyclic group. More preferably, the formula:

[Formula 15]

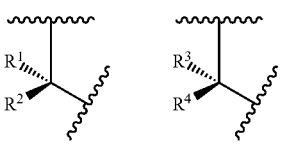

wherein each symbol is as defined in the Item 1 is

[Formula 16]

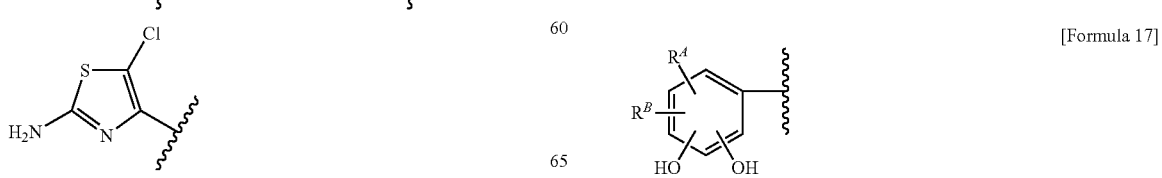

And, "m" is preferably 0 or 1, and 0 is particularly preferable.

And, "k" is preferably 0 or 1, and 0 is particularly preferable.

"R$^5$" is preferably a hydrogen atom, methyl, ethyl, or isopropyl. More preferable is a hydrogen atom.

Examples of a preferable embodiment of the formula:

[Formula 17]

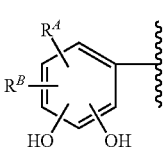

include the formulae:
[Formula 18]
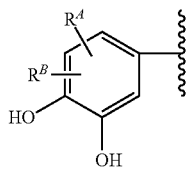 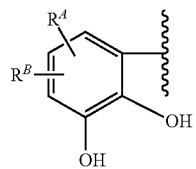
(wherein $R^A$ and $R^B$ are as defined in the Item 1)
Examples of a more preferable embodiment include
[Formula 19]
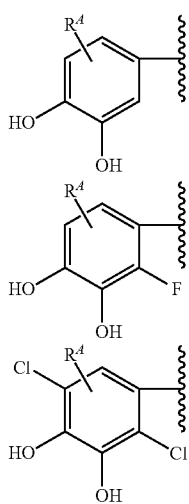
Examples of "E" include the following groups.
[Formula 20]
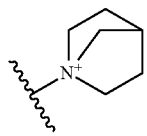 (1A)
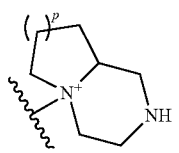 (2A)
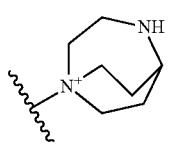 (3A)
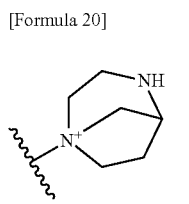 (4A)
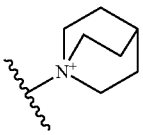 (5A)
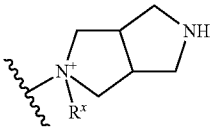 (6A)
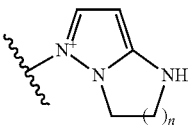 (7A)
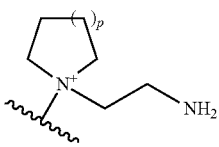 (8A)
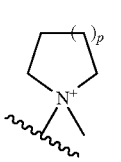 (8A′)
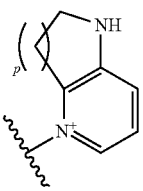 (9A)
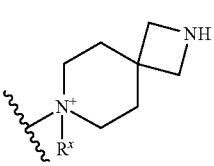 (10A)
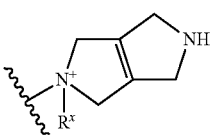 (11A)
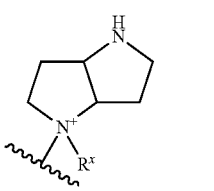 (12A)
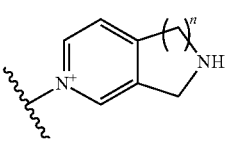 (13A)

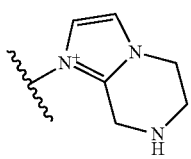
(14A)
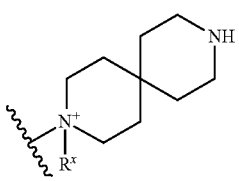
(15A)
[Formula 21]
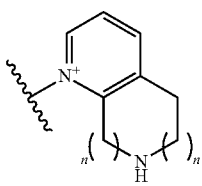
(16A)
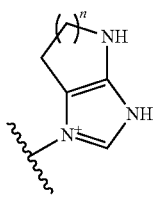
(17A)
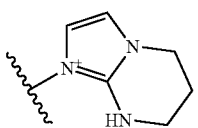
(18A)
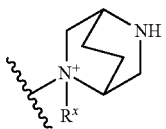
(19A)
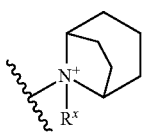
(20A)
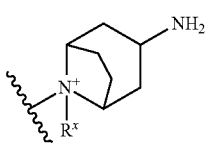
(20A′)
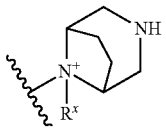
(21A)
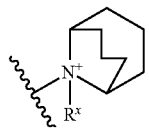
(22A)
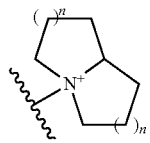
(23A)
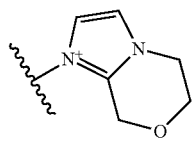
(24A)
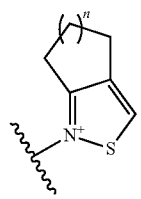
(25A)
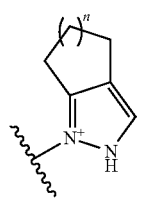
(26A)
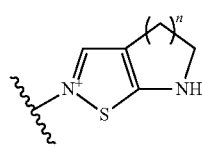
(27A)
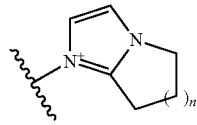
(28A)
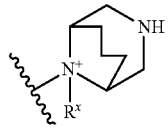
(29A)
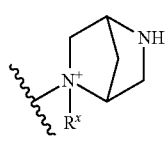
(30A)

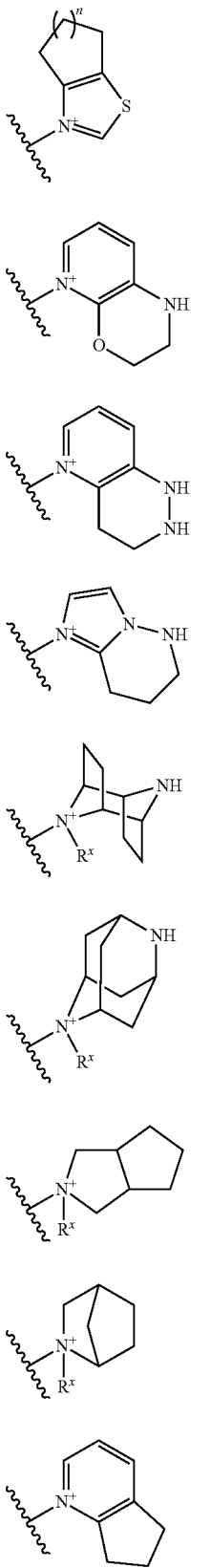
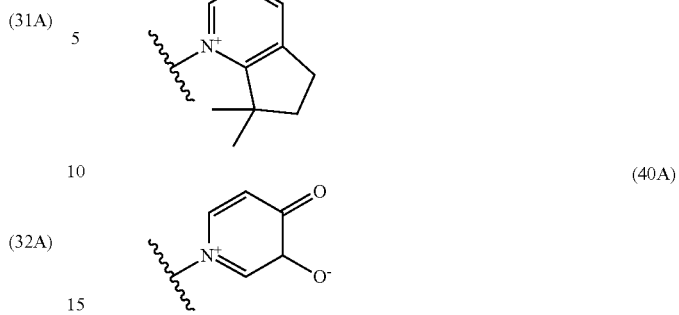
wherein p is an integer of 1 to 3, n is 1 or 2, and $R^x$ is substituted or unsubstituted alkyl.
Herein, preferable examples of $R^x$ include methyl, ethyl, trifluoromethyl, carboxymethyl, carbamoylmethyl, hydroxyethyl, aminoethyl, etc.
Further preferable examples of "E" include the following formulae:
[Formula 23]
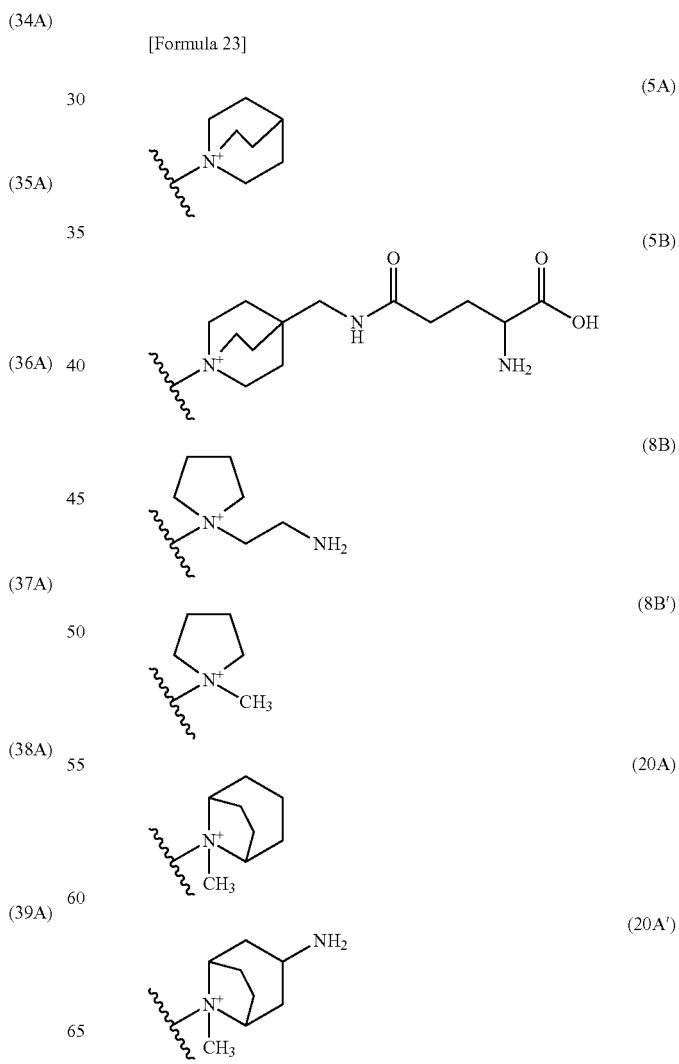

-continued

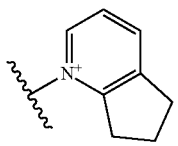
(39A)

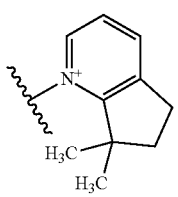
(39A')

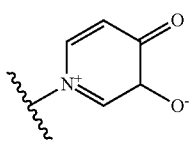
(40A)

etc.

Preferable combinations of A, B, and E are that A is above-mentioned formula (i) or (ii), B is above-mentioned formula (v), and E is above-mentioned formula (5), (8), (20), (23), (39) or (40). More preferable combinations are that A is above-mentioned formula (ia), (ib) or (iia), B is above-mentioned formula (v), and E is above-mentioned (5A), (5B), (8B), (8B'), (20A), (20A'), (23A), (39A), (39A') or (40A).

Nomenclature of a substituted position on the cephem skeleton of the formula (I) is as follows. The 7-side chain and the 3-side chain herein represent groups which bind to the 7-position and the 3-position of the following cephem skeleton.

[Formula 24]

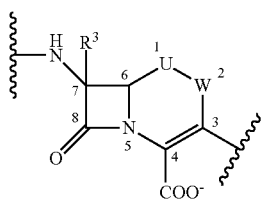

A salt of the formula (I) includes salts in which a hydrogen atom of a 4-position carboxyl group, a carboxyl group on the 7-side chain and/or a hydroxyl group on a catechol group is dissociated to form a salt with a counter cation, salts in which an amino group on the 7-side chain forms a salt with an inorganic acid or an organic acid, and salts in which the 3-side chain quaternary amine moiety forms a salt with a counter anion.

Examples of a pharmaceutically acceptable salt of the formula (I) include salts or intramolecular salts formed with an inorganic base, ammonia, an organic base, an inorganic acid, an organic acid, a basic amino acid, a halogen ion, etc. Examples of the inorganic base include alkali metals (Na, K etc.), and alkaline earth metals (Mg etc.), and examples of the organic base include procaine, 2-phenylethylbenzylamine, dibenzylethylenediamine, ethanolamine, diethanolamine, trishydroxymethylaminomethane, polyhydroxyalkylamine, N-methylglucosamine, etc. Examples of the inorganic acid include hydrochloric acid, hydrobromic acid, sulfuric acid, nitric acid, phosphoric acid, etc. Examples of the organic acid include p-toluenesulfonic acid, methanesulfonic acid, formic acid, acetic acid, trifluoroacetic acid, maleic acid, etc. Examples of the basic amino acid include lysine, arginine, ornithine, histidine, etc.

The compound represented by the formula (I) of the subject invention or a pharmaceutically acceptable salt thereof may form a solvate (e.g. hydrate etc.) and/or polymorphic crystal, and the subject invention also includes those various solvates and polymorphic crystals. In such "solvate", an arbitrary number of solvent molecules (e.g. water molecule etc.) may be coordinated to the compound represented by the formula (I). By leaving the compound represented by the formula (I) or a pharmaceutically acceptable salt thereof in the atmosphere, it may absorb a moisture to adhere with adsorbed water or form a hydrate thereof. Also, a crystalline polymorphism of the compound of Formula (I) or pharmaceutically acceptable salt thereof can be formed by recrystallization.

The compound represented by the formula (I) of the subject invention or a pharmaceutically acceptable salt thereof may form a prodrug, and the subject invention also includes such various prodrugs. The prodrug is a derivative of the compound of the subject invention having a group which can be chemically or metabolically degraded to become a pharmaceutically active compound of the subject invention in vivo by solvolysis or under physiological condition. The prodrug includes compounds which enzymatically undergo oxidation, reduction, hydrolysis etc. under the physiological condition in a living body, and are converted into the compound represented by the formula (I), compounds which are hydrolyzed by gastric acid etc., and are converted into the compound represented by the formula (I) etc. A method of selecting a suitable prodrug derivative and a process for producing the prodrug are described, for example, in Design of Prodrugs, Elsevier, Amsterdam 1985. The prodrug may be active compound in itself.

The compound (I) of the subject invention is not limited to particular isomers, but includes all possible isomers and racemates as those exemplified below.

For example, the formula:

[Formula 25]

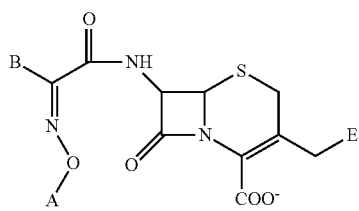
(I)

wherein each symbol is as defined in the Item 1 in the formula (I) includes the formula:

[Formula 26]

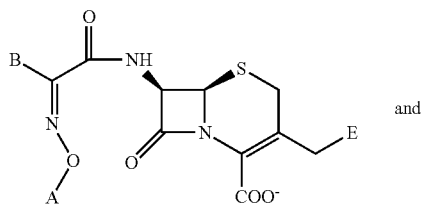
and

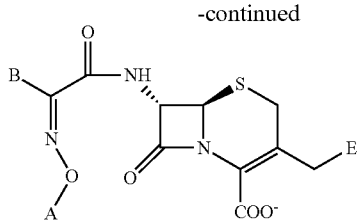

wherein each symbol is as defined in the Item 1, etc.

For example, the formula of E in the formula (I) includes a group which forms a resonance structure, and also includes a group in which a cationic nitrogen atom becomes a zero-valent nitrogen atom (e.g.: 40A), as shown in the following formula:

[Formula 27]

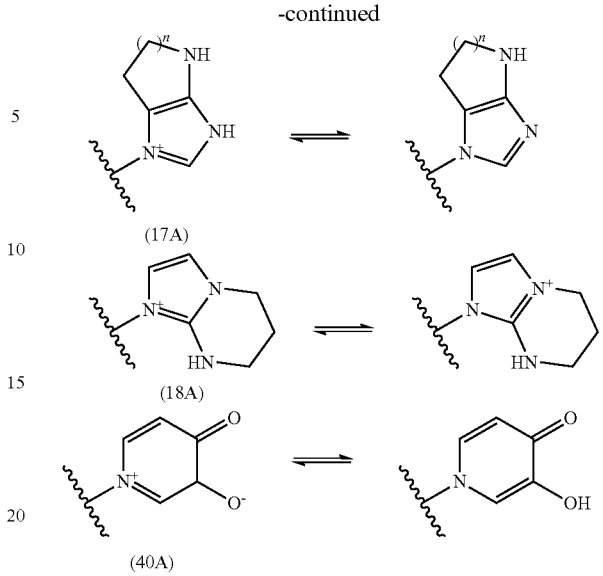

wherein each symbol is as defined in the Item 1.

The compound represented by the formula (I) in connection with the subject invention can be produced, for example, by the following general synthesis method.

[Formula 28]

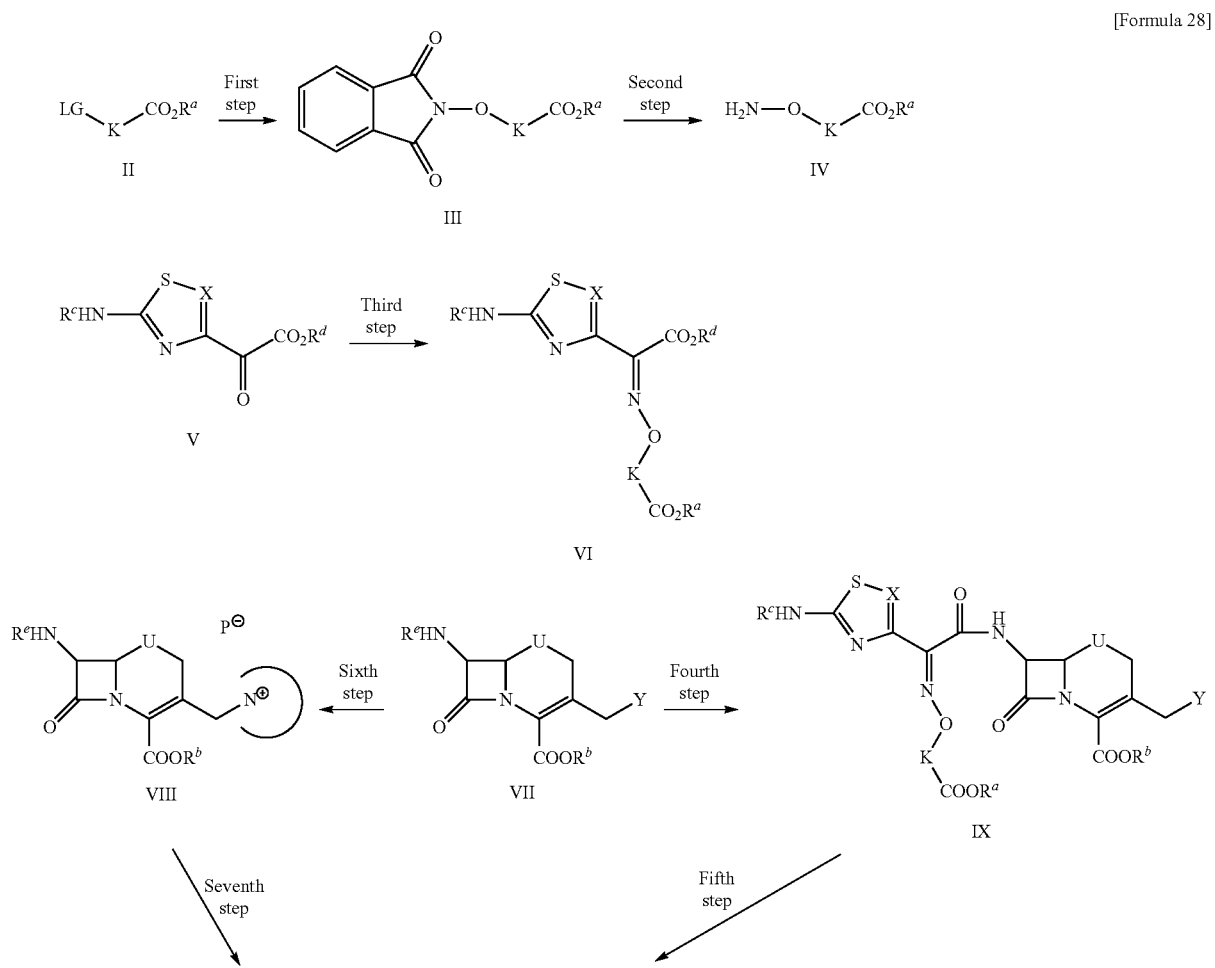

-continued

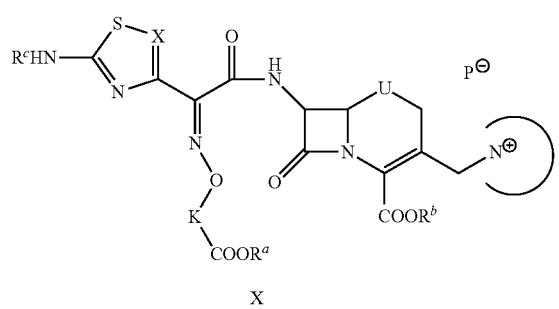 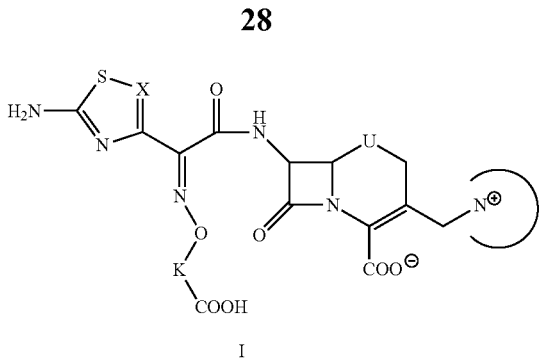

X           Eighth step:           I wherein X, U, $R^a$, $R^b$, and $R^c$ are as defined above, $P^-$ is a counter anion of a quaternary nitrogen atom, U is S or S=O, K represents the formula:

[Formula 29]

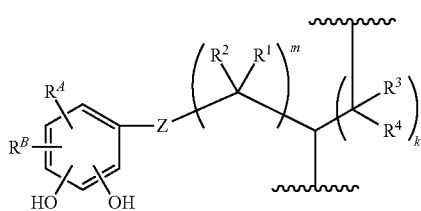

wherein each symbol is as defined above,
the formula:

[Formula 30]

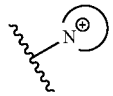

represents a part of (E) of the formula (I) including a heterocyclic group part having a cationic nitrogen atom on the 3-side chain, LG and Y represent a leaving group (e.g. hydroxy, halogen (Cl, Br, I), optionally substituted carbamoyloxy, acyloxy, methanesulfonyloxy, toluenesulfonyloxy, etc.),
$R^d$ represents hydrogen or a carboxy protective group, and $R^e$ represents hydrogen or an amino protective group.

1) Synthesis of 7-Side Chain Raw Material: Compound (VI)
First Step:

Compound (III) is obtained by a reaction with N-hydroxyphthalimide, in the presence of Compound (II) (LG is hydroxy) and a Mitsunobu reagent, or in the presence of Compound (II) (LG is other leaving group) and a base (sodium hydride, sodium methoxide etc.).

The amount of N-hydroxyphthalimide is usually about 1 to 5 mole, preferably 1 to 2 mole, relative to Compound (II).

Examples of the reaction solvent include ethers (e.g.: dioxane, tetrahydrofuran, diethyl ether, tert-butyl methyl ether, diisopropyl ether), halogenated hydrocarbons (e.g.: dichloromethane, chloroform, carbon tetrachloride), hydrocarbons (e.g.: n-hexane, benzene, toluene), amides (e.g.: formamide, N, N-dimethylformamide, N,N-dimethylacetamide, N-methylpyrrolidone), etc., or mixed solvents thereof.

The reaction temperature is usually about −50 to 100° C., preferably about −40 to 50° C., more preferably about −30 to 0° C.

Second Step:

Compound (IV) is obtained by adding N-methylhydrazine or hydrazine to Compound (III) to react them.

The amount of N-methylhydrazine or hydrazine is about 1 to 10 mole, preferably 1 to 5 mole, further preferably 1 to 2 mole, relative to Compound (III).

Examples of the reaction solvent include ethers (e.g.: dioxane, tetrahydrofuran, diethyl ether, tert-butyl methyl ether, diisopropyl ether), esters (e.g.: ethyl formate, ethyl acetate, isopropyl acetate), halogenated hydrocarbons (e.g.: dichloromethane, chloroform, carbon tetrachloride), hydrocarbons (e.g.: n-hexane, benzene, toluene), alcohols (e.g.: methanol, ethanol, isopropanol), amides (e.g.: formamide, N,N-dimethylformamide, N,N-dimethylacetamide, N-methylpyrrolidone), ketones (e.g.: acetone, methyl ethyl ketone), nitriles (e.g.: MeCN, propionitrile), dimethyl sulfoxide, water, etc., or mixed solvents thereof, etc.

The reaction temperature is usually about 0 to 100° C., preferably about 0 to 50° C., more preferably about 10 to 30° C.

Third Step:

Compound (VI) is obtained by adding Compound (IV) to Compound (V) which is commercially available or is obtained by the known method, to react them (this is described, for example, in Bioorganic & Medicinal Chemistry, vol. 15, P. 6716-6732 (2007)).

Examples of the reaction solvent include ethers (e.g.: dioxane, tetrahydrofuran, diethyl ether, tert-butyl methyl ether, diisopropyl ether), esters (e.g.: ethyl formate, ethyl acetate, isopropyl acetate), halogenated hydrocarbons (e.g.: dichloromethane, chloroform, carbon tetrachloride), hydrocarbons (e.g.: n-hexane, benzene, toluene), alcohols (e.g.: methanol, ethanol, isopropanol), amides (e.g.: formamide, N,N-dimethylformamide, N,N-dimethylacetamide, N-methylpyrrolidone), ketones (e.g.: acetone, methyl ethyl ketone), nitriles (e.g.: MeCN, propionitrile), dimethyl sulfoxide, water, etc., or mixed solvents thereof, etc.

The reaction temperature is usually about 0 to 100° C., preferably about 0 to 50° C., more preferably about 10 to 30° C.

2) 7-Position Amidation and 3-Position Side Chain Formation;
Synthesis of Compound (X)
Fourth Step (7-Position Amidation Reaction):

Compound (IX) is obtained by reacting Compound (VII) which is commercially available or is synthesized according to the method described in a reference (e.g.: JP-A No. 60-231684, JP-A No. 62-149682 etc.), and Compound (VI). In this case, preferably, $R^a$ and $R^b$ are a carboxy protective group, $R^c$ is an amino protective group, and $R^d$ and $R^e$ are hydrogen.

The amount of Compound (VI) is usually about 1 to 5 mole, preferably 1 to 2 mole, relative to 1 mole of Compound (VII).

Examples of the reaction solvent include ethers (e.g.: dioxane, tetrahydrofuran, diethyl ether, tert-butyl methyl ether, diisopropyl ether), esters (e.g.: ethyl formate, ethyl acetate, isopropyl acetate), halogenated hydrocarbons (e.g.: dichloromethane, chloroform, carbon tetrachloride), hydrocarbons (e.g.: n-hexane, benzene, toluene), amides (e.g.: formamide, N,N-dimethylformamide, N,N-dimethylacetamide, N-methylpyrrolidone), ketones (e.g.: acetone, methyl ethyl ketone), nitriles (e.g.: MeCN, propionitrile), dimethyl sulfoxide, water etc., or mixed solvents thereof, etc.

The reaction temperature is usually about −40 to 80° C., preferably about −20 to 50° C., more preferably about −10 to 30° C.

The amidation reaction may be performed after a carboxyl moiety is converted into a reactive derivative (e.g.: inorganic base salt, organic base salt, acid halide, acid azide, acid anhydride, mixed acid anhydride, active amide, active ester, active thioester). Examples of the inorganic base include alkali metals (e.g.: Na, K etc.), alkaline earth metals (e.g.: Ca, Mg) etc., examples of the organic base include trimethylamine, triethylamine, tert-butyldimethylamine, dibenzylmethylamine, benzyldimethylamine, N-methylmorpholine, diisopropylethylamine etc., examples of the acid halide include acid chloride, acid bromide etc., examples of the mixed acid anhydride include monoalkylcarbonic acid mixed acid anhydride, aliphatic carboxylic acid mixed acid anhydride, aromatic carboxylic acid mixed acid anhydride, organic sulfonic acid mixed acid anhydride etc., and examples of the active amide include amides with a nitrogen-containing heterocyclic compound. Examples of the active ester include organic phosphoric acid esters (e.g.: diethoxyphosphoric acid ester, diphenoxyphosphoric acid ester etc.), p-nitrophenyl ester, 2,4-dinitrophenyl ester, cyanomethyl ester, etc. Examples of the active thioester include esters with an aromatic heterocyclic thiol compound (e.g.: 2-pyridylthiol ester) etc. In addition, in the above-mentioned reaction, a suitable condensing agent may be optionally used. As the condensing agent, 1-dimethylaminopropyl-3-ethylcarbodiimide.hydrochloride (WSCD.HCl), N,N'-dicyclohexylcarbodiimide, N,N'-carbonyldiimidazole, N,N'-thiocarbonyldiimidazole, N-ethoxycarbonyl-2-ethoxy-1,2-dihydroquinoline, phosphorus oxychloride, alkyloxyacetylene, 2-chloropyridinium methyl iodide, 2-fluoropyridinium methyl iodide, trifluoroacetic acid anhydride etc. are used.

Fifth Step (3-Position Side Chain Formation Reaction):

Compound (X) is obtained by reacting Compound (IX) and corresponding tertiary amine. In this case, preferably, $R^a$ and $R^b$ are a carboxy protective group, and $R^c$ is an amino protective group.

The amount of corresponding tertiary amine is usually 1 to 5 mole, preferably 1 to 2 mole, relative to 1 mole of Compound (IX).

Examples of the reaction solvent include ethers (e.g.: dioxane, tetrahydrofuran, diethyl ether, tert-butyl methyl ether, diisopropyl ether), esters (e.g.: ethyl formate, ethyl acetate, isopropyl acetate), halogenated hydrocarbons (e.g.: dichloromethane, chloroform, carbon tetrachloride), hydrocarbons (e.g.: n-hexane, benzene, toluene), amides (e.g.: formamide, N,N-dimethylformamide, N,N-dimethylacetamide, N-methylpyrrolidone), ketones (e.g.: acetone, methyl ethyl ketone), nitriles (e.g.: MeCN, propionitrile), dimethyl sulfoxide, water, etc., or mixed solvents thereof, etc.

The reaction temperature is usually −20 to 60° C., preferably −10 to 40° C., more preferably 0 to 20° C.

In addition, a compound in which U=S in Compound (X) can be obtained by reducing U=SO in Compound (X). Examples of the reducing agent include potassium iodide-acetyl chloride, etc.

3) 3-Position Side Chain Formation and 7-Position Amidation;

Synthesis of Compound (X)

Sixth Step (3-Position Side Chain Formation Reaction):

Compound (VIII) is obtained by reacting Compound (VII) and corresponding tertiary amine. In this case, preferably, $R^b$ is a carboxy protective group, and $R^e$ is an amino protective group.

The amount of corresponding tertiary amine is usually 1 to 5 mole, preferably 1 to 2 mole, relative to 1 mole of Compound (VII).

Examples of the reaction solvent include ethers (e.g.: dioxane, tetrahydrofuran, diethyl ether, tert-butyl methyl ether, diisopropyl ether), esters (e.g.: ethyl formate, ethyl acetate, isopropyl acetate), halogenated hydrocarbons (e.g.: dichloromethane, chloroform, carbon tetrachloride), hydrocarbons (e.g.: n-hexane, benzene, toluene), amides (e.g.: formamide, N,N-dimethylformamide, N,N-dimethylacetamide, N-methylpyrrolidone), ketones (e.g.: acetone, methyl ethyl ketone), nitriles (e.g.: MeCN, propionitrile), dimethyl sulfoxide, water, etc., or mixed solvents thereof, etc.

The reaction temperature is usually −20 to 60° C., preferably −10 to 40° C., more preferably 0 to 20° C.

In addition, tertiary amine moiety (corresponding to a substituent E of the Item 1) used in the 3-position side chain formation reaction of the fifth step and the sixth step may be commercially available reagents or can be obtained by the known method and/or the method described in the present description.

Seventh Step (7-Position Amidation Reaction):

Compound (X) is obtained by reacting Compound (VIII) and Compound (VI). In this case, preferably, $R^a$ and $R^b$ are a carboxy protective group, $R^c$ is an amino protective group, and $R^d$ and $R^e$ are hydrogen.

The amount of Compound (VI) is usually about 1 to 5 mole, preferably 1 to 2 mole, relative to 1 mole of Compound (VIII).

Examples of the reaction solvent include ethers (e.g.: dioxane, tetrahydrofuran, diethyl ether, tert-butyl methyl ether, diisopropyl ether), esters (e.g.: ethyl formate, ethyl acetate, isopropyl acetate), halogenated hydrocarbons (e.g.: dichloromethane, chloroform, carbon tetrachloride), hydrocarbons (e.g.: n-hexane, benzene, toluene), amides (e.g.: formamide, N,N-dimethylformamide, N,N-dimethylacetamide, N-methylpyrrolidone), ketones (e.g.: acetone, methyl ethyl ketone), nitriles (e.g.: MeCN, propionitrile), dimethyl sulfoxide, water, etc., or mixed solvents thereof, etc.

The reaction temperature is usually about −40 to 80° C., preferably about −20 to 50° C., more preferably about −10 to 30° C.

The above-mentioned amidation reaction may be performed after a carboxyl moiety is converted into a reactive derivative (e.g.: inorganic base salt, organic base salt, acid halide, acid azide, acid anhydride, mixed acid anhydride, active amide, active ester, active thioester). Examples of the inorganic base include alkali metals (e.g.: Na, K etc.), alkaline earth metals (e.g.: Ca, Mg) etc., examples of the organic base include trimethylamine, triethylamine, tert-butyldimethylamine, dibenzylmethylamine, benzyldimethylamine, N-methylmorpholine, diisopropylethylamine etc., examples of the acid halide include acid chloride, acid bromide etc., examples of the mixed acid anhydride include monoalkylcarbonic acid mixed acid anhydride, aliphatic carboxylic acid mixed acid anhydride, aromatic carboxylic acid mixed acid anhydride, organic sulfonic acid mixed acid anhydride, etc., and examples of the active amide include amides with a nitrogen-containing heterocyclic compound. Examples of the active ester include organic phosphoric acid esters (e.g.: diethoxyphosphoric acid ester, diphenoxyphosphoric acid ester etc.), p-nitrophenyl ester, 2,4-dinitrophenyl ester, cyanomethyl ester, etc. Examples of the active thioester include esters with an aromatic heterocyclic thiol compound (e.g.: 2-pyridylthiol ester) etc. In addition, in the above-mentioned reaction, a suitable condensing agent may be optionally used. As the condensing agent, for example, l-dimethylaminopropyl-3-ethylcarbodiimide.hydrochloride (WSCD.HCl), N,N'-dicyclohexylcarbodiimide, N,N'-carbonyldiimidazole, N,N'-thiocarbonyldiimidazole, N-ethoxycarbonyl-2-ethoxy-1,2-dihydroquinoline, phosphorus oxychloride, alkyloxyacetylene, 2-chloropyridinium methyl iodide, 2-fluoropyridinium methyl iodide, trifluoroacetic acid anhydride etc. are used.

4) Deprotecting Reaction

Eighth Step:

Compound (I) is obtained by subjecting Compound (X) to a deprotecting reaction by the method well-known to a person skilled in the art.

Examples of the reaction solvent include ethers (e.g.: anisole, dioxane, tetrahydrofuran, diethyl ether, tert-butyl methyl ether, diisopropyl ether), esters (e.g.: ethyl formate, ethyl acetate, n-butyl acetate), halogenated hydrocarbons (e.g.: dichloromethane, chloroform, carbon tetrachloride, hydrocarbons (e.g.: n-hexane, benzene, toluene), amides (e.g.: formamide, N,N-dimethylformamide, N,N-dimethylacetamide, N-methylpyrrolidone), ketones (e.g.: acetone, methyl ethyl ketone), nitriles (e.g.: MeCN, propionitrile), nitros (e.g.: nitromethane, nitroethane, nitrobenzene), dimethyl sulfoxide, water, etc. These solvents may be used alone, or may be used by mixing two or more kinds.

The reaction temperature is usually about −30 to 100° C., preferably about 0 to 50° C., more preferably about 0 to 10° C.

As a catalyst, a Lewis acid (e.g.: $AlCl_3$, $SnCl_4$, $TiCl_4$), protonic acid (e.g.: HCl, HBr, $H_2SO_4$, HCOOH) etc. can be used.

In addition, the obtained compound may be further chemically modified, and thereby an ester, or a compound of which an amino on the thiazole ring at the 7-position thereof is protected, or a pharmaceutically acceptable salt, or a solvate thereof can be synthesized.

The compound of the subject invention has a wide antimicrobial spectrum, and can be used for preventing or treating various diseases generated by pathogenic microbes in various kinds of mammal including human, for example, infection of the airway, urinary tract infectious disease, respiratory tract infection, sepsis, nephritis, cholecystitis, oral infectious disease, endocarditis, pneumonia, marrow meningitis, tympanitis, enterocolitis, empyema, wound infection, opportunistic infection, etc.

The compound of the subject invention exhibits high antimicrobial activity against, particularly, Gram negative bacteria, preferably, Enterobacteriaceae Gram negative bacteria (*Eschericha coli, Klebsiella, Serratia, Enterobacter, Citrobacter, Morganella, Providencia, Proteus*, etc.), Gram negative bacteria which colonize in respiratory apparatuses (*Hemophilus, Moraxella* etc.) and glucose non-fermentation Gram negative bacteria (*Pseudomonas aeruginosa, Pseudomonas* other than *Pseudomonas aeruginosa, Stenotrophomonas, Burkholderia, Acinetobacter* etc.). The compound of the subject invention is stable to beta-lactamase belonging to Classes A, B, C and D produced by these Gram negative bacteria, and has high antimicrobial activity against various beta-lactam drug resistant Gram negative bacteria such as ESBL producing bacteria. Particularly, since the compound of the subject invention is also extremely stable to metallo-beta-lactamase belonging to Class B, including IMP type, VIM type, L-1 type etc., it is also effective against Gram negative bacteria which are resistant to various beta-lactam drugs such as Cephems and Carbapenems. Further preferable compounds also have, as disposition, the characteristics that a blood concentration is high, an effect lasting time is long, and/or tissue transitivity is remarkable, etc. In addition, preferable compounds are safe in respect of the side effects. In addition, preferable compounds have high water-solubility and, particularly, they are suitable as injection drugs.

Compound (I) can be administered parenterally or orally as injectables, capsules, tablets, or granules, and is preferably administered as injectables. As a dose, usually, about 0.1 to 100 mg/day, preferably about 0.5 to 50 mg/day may be administered per 1 kg of body weight of a patient or an animal, preferably by dividing into two to four times a day. A carrier when used as injectables is, for example, distilled water, physiological saline, and a base etc. for adjusting pH may be used. A carrier when used as capsules, granules, or tablets may be known excipients (e.g.: starch, lactose, white sugar, calcium carbonate, calcium phosphate, etc.), binders (e.g.: starch, gum arabic, carboxymethylcellulose, hydroxypropylcellulose, crystalline cellulose, etc.), lubricants (e.g.: magnesium stearate, talc, etc.) etc.

EXAMPLES

The subject invention will be explained in more detail below byway of Examples and Reference Examples, as well as Test Examples, but the subject invention is not limited to them.

In Example, the meaning of each abbreviation is as follows.

BH: benzhydryl

Bn: benzyl

Boc: tert-butoxycarbonyl

DMA: N,N-dimethylacetamide

DME: dimethoxyethane

DMF: N,N-dimethylformamide

EDC: 1-ethyl-3-(3-dimethylaminopropyl)carbodiimide

HATU: O-(7-azabenzotriazol-1-yl)-1,1,3,3-tetramethyluronium hexafluorophosphate

HOBt: 1-hydroxybenzotriazole mCPBA: m-chloroperbenzoic acid

PMB: paramethoxybenzyl

ODS: octadecylsilyl t-Bu: tert-butyl

Tr: trityl

MeCN: acetonitrile

Me: methyl

Example 1
Synthesis of Compound I-1
[Formula 31]
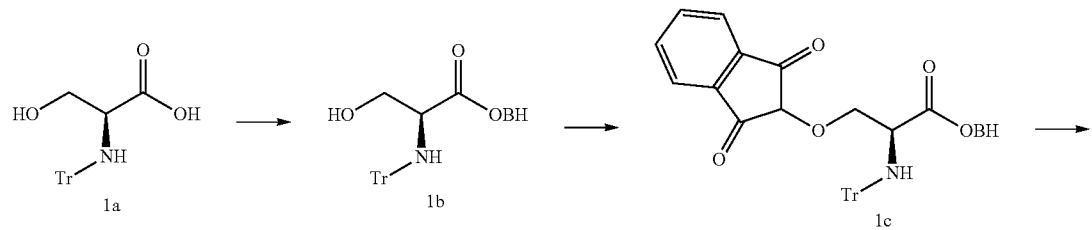
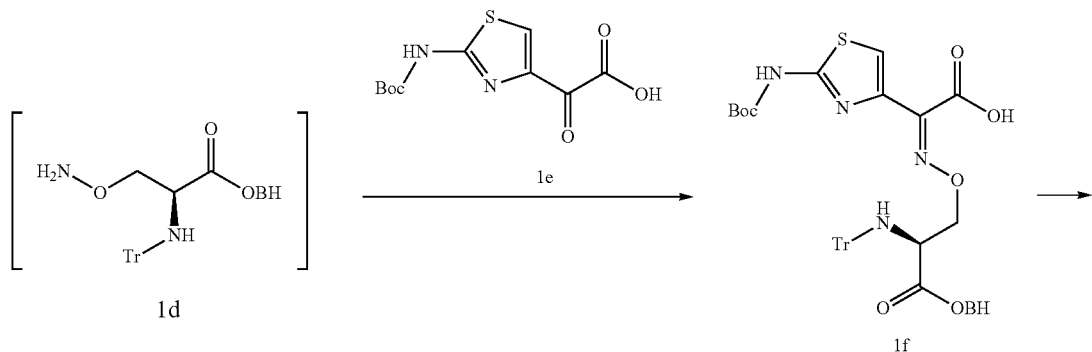
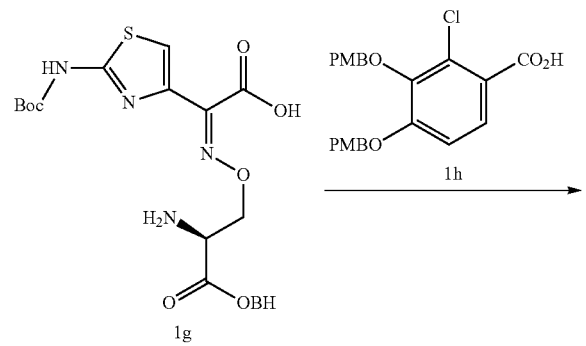
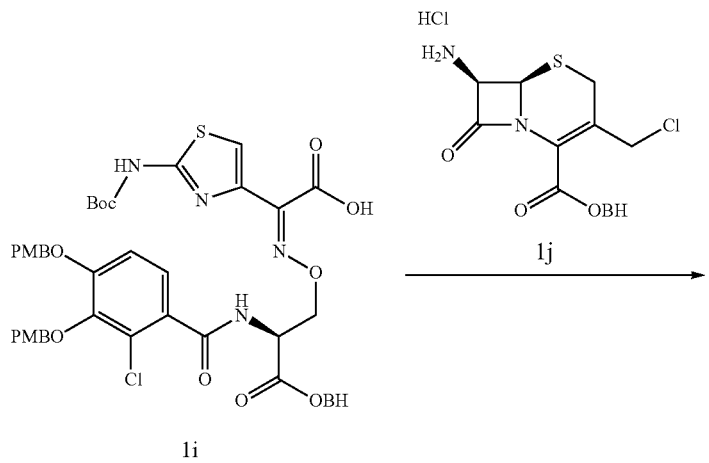

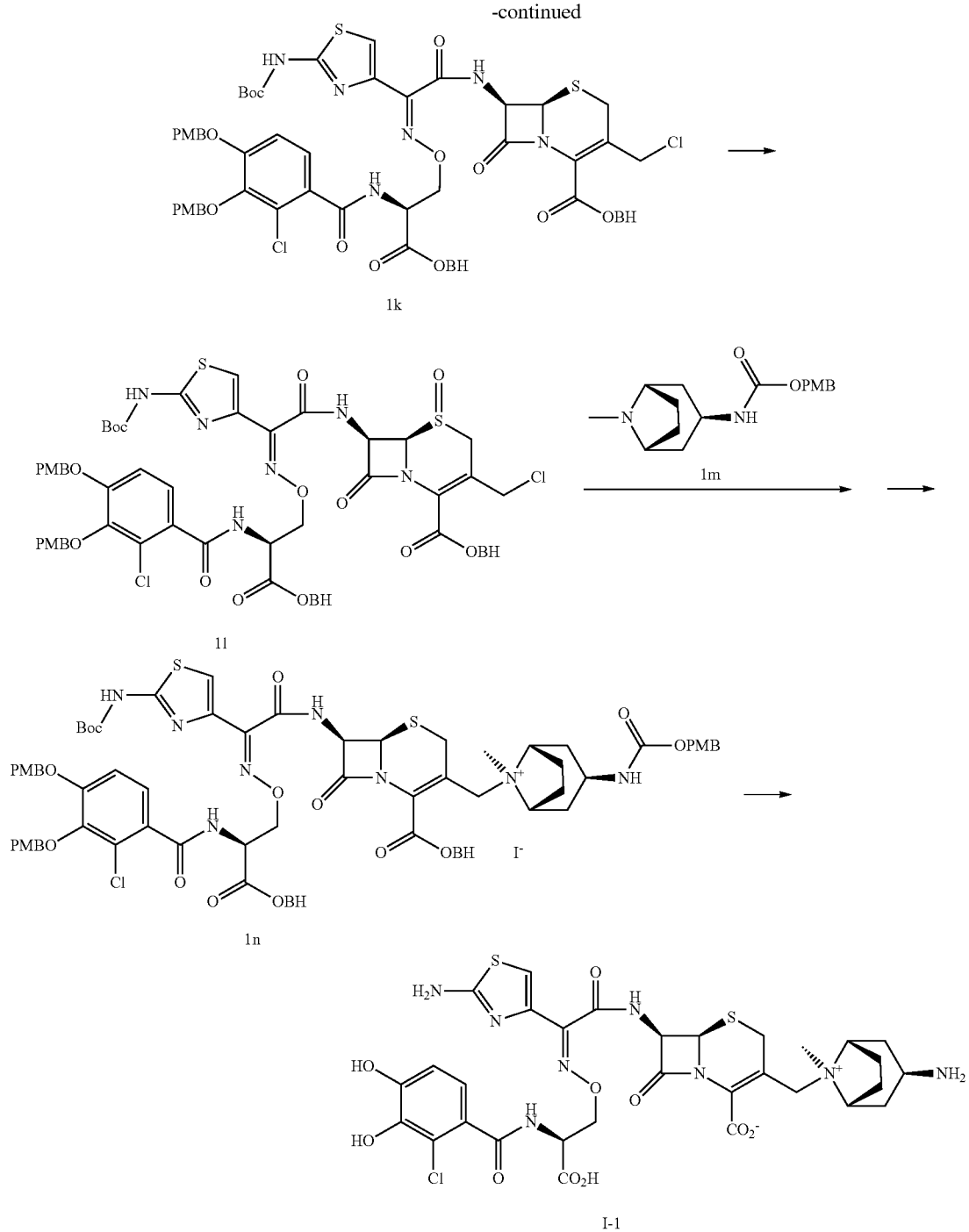

Step 1: Compound 1a→Compound 1b

After a tetrahydrofuran (20 ml) solution of diphenyldiazomethane (10.72 g, 55.2 mmol) was added to a tetrahydrofuran (150 ml) solution of compound 1a (15.98 g, 46.0 mmol) synthesized referring to J. Org. Chem. 2008, 73, 517-521, the mixture was stirred at room temperature overnight. The reaction solution was concentrated under reduced pressure, subjected to silica gel column chromatography, and eluted with hexane/ethyl acetate, and fractions containing the desired compound were concentrated under reduced pressure to obtain compound 1b (20.97 g, 89%).

$^1$H-NMR (CDCl$_3$) δ: 7.45-7.09 (25H, m), 6.46 (1H, s), 3.67-3.59 (2H, m), 3.41-3.34 (1H, m), 3.12 (1H, br s), 2.26-2.17 (1H, m).

Step 2: Compound 1b→Compound 1c

To a tetrahydrofuran (210 ml) solution of compound 1b (20.97 g, 40.8 mmol) and N-hydroxyphthalimide (7.33 g, 44.9 mmol) were added dimethylazodicarboxylic acid (6.63 ml, 44.9 mmol) and triphenylphosphine (11.78 g, 44.9 mmol) under ice-cooling. After the mixture was stirred at room temperature overnight, N-hydroxyphthalimide (1.33 g, 8.17 mmol), dimethylazodicarboxylic acid (1.21 ml, 8.17 mmol) and triphenylphosphine (2.14 g, 8.17 mmol) were added, and the mixture was stirred at room temperature for 2 hours. The reaction solution was diluted with toluene, and tetrahydrofuran was distilled off under reduced pressure. The precipitated solid was removed by filtration, the filtrate was concentrated under reduced pressure, subjected to silica gel column chromatography, and eluted with hexane/ethyl acetate. Fractions containing the desired compound were concentrated under reduced pressure to obtain compound 1c (20.71 g, 77%).

$^1$H-NMR (CDCl$_3$) δ: 7.79-7.70 (4H, m), 7.52-7.49 (6H, m), 7.33-7.05 (19H, m), 6.45 (1H, s), 4.43 (1H, dd, J=9.38, 2.52 Hz), 3.86-3.75 (2H, m), 3.29 (1H, d, J=9.15 Hz).

Step 3: Compound 1c→Compound 1d+Compound 1e→Compound 1f

After a dichloromethane (200 mL) solution of compound 1c (20.71 g, 31.4 mmol) was cooled to −40° C., methylhydrazine (1.76 ml, 31.4 mmol) was added, and the mixture was stirred for 3 hours under ice-cooling. After the reaction solution was filtered, methanol (90 mL) and compound 1e (8.56 g, 33.0 mmol) were added to the filtrate, and the mixture was stirred at room temperature for 2 hours. Concentration under reduced pressure afforded compound 1f (26.38 g). Compound 1f was used in the next reaction without purification.

Step 4: Compound 1f→Compound 1g

The total amount (corresponding to 31.4 mmol) of the resulting compound 1f was dissolved in acetone (250 mL), 6 mol/L hydrochloric acid (5.23 ml, 31.4 mmol) was added, and the mixture was stirred at room temperature for 1 hour. To the reaction solution was added the HP20-SS resin, and acetone was distilled off under reduced pressure. The resulting mixed solution was purified by HP20-SS column chromatography. Fractions containing the desired compound were concentrated under reduced pressure, and the precipitated solid was filtered to obtain compound 1g (16.44 g, 97%).

$^1$H-NMR (DMSO-d$_6$) δ: 11.64 (1H, s), 7.47-7.18 (14H, m), 6.83 (1H, s), 4.59-4.50 (1H, m), 4.32-4.24 (2H, m), 1.47 (9H, s).

Step 5: Compound 1g+Compound 1h→Compound 1i

Compound 1h (13.47 g, 31.4 mmol) was suspended in dichloromethane (100 ml), 1-chloro-N,N,2-trimethyl-1-propenylamine (4.53 ml, 34.3 mmol) was added under ice-cooling, and the mixture was stirred at room temperature for 30 minutes. The reaction solution was poured into an ice-cooled dichloromethane (100 ml) solution of compound 1g (15.44 g, 28.6 mmol) and triethylamine (8.71 ml, 62.8 mmol), and the mixture was stirred for 1 hour under ice-cooling. The reaction solution was diluted with dichloromethane, and the organic layer was washed with hydrochloric acid, water and brine, and dried over magnesium sulfate. After magnesium sulfate was filtered, the filtrate was concentrated under reduced pressure to obtain compound 1i (30.15 g). Compound 1i was used in the next reaction without purification.

Step 6: Compound 1i+Compound 1j→Compound 1k

The total amount (corresponding to 31.4 mmol) of the resulting compound 1i and compound 1j (14.2 g, 31.4 mmol) were suspended in dichloromethane (300 ml), and cooled to −40° C., and dichlorophenylphosphoric acid (7.04 ml, 47.1 mmol) was added. Then, N-methylmorpholine (15.53 ml, 141 mmol) was added dropwise at −40° C., and the mixture was stirred at −40° C. to −30° C. for 4 hours. The reaction solution was diluted with dichloromethane, washed with 0.2 mol/L hydrochloric acid, an aqueous saturated sodium bicarbonate solution, and brine, and dried over magnesium sulfate. After magnesium sulfate was filtered, the filtrate was concentrated under reduced pressure, subjected to silica gel column chromatography, and eluted with hexane/ethyl acetate. Fractions containing the desired compound were concentrated under reduced pressure to obtain compound 1k (27.33 g, 65%) as a crude product. Compound 1k was used in the next reaction without further purification.

Step 7: Compound 1k→Compound 1l

After a dichloromethane (300 mL) solution of compound 1k (27.33 g, 20.27 mmol) was cooled to −50° C., a dichloromethane (25 mL) solution of mCPBA (4.84 g, 18.24 mmol) was added, and the mixture was stirred at −50° C. to −40° C. for 1 hour. The reaction solution was diluted with dichloromethane, washed with a 5% aqueous sodium hydrogen sulfite solution, an aqueous saturated sodium bicarbonate solution, and brine, and dried over magnesium sulfate. After magnesium sulfate was filtered, the filtrate was concentrated under reduced pressure, subjected to silica gel column chromatography, and eluted with hexane/ethyl acetate. Fractions containing the desired compound were concentrated under reduced pressure to obtain compound 1l (17.84 g, 65%).

$^1$H-NMR (CDCl$_3$) δ: 8.14 (1H, d, J=8.39 Hz), 7.95 (1H, br s), 7.64 (1H, d, J=9.30 Hz), 7.44 (2H, d, J=6.71 Hz), 7.35-7.23 (23H, m), 6.91-6.76 (8H, m), 5.98 (1H, dd, J=9.30, 4.58 Hz), 5.24 (1H, dt, J=8.18, 3.13 Hz), 4.97-4.68 (6H, m), 4.42 (1H, d, J=4.73 Hz), 4.01 (1H, d, J=12.20 Hz), 3.82-3.72 (7H, m), 3.26 (1H, d, J=18.68 Hz), 3.10 (1H, d, J=18.68 Hz), 1.52 (9H, s).

Step 8: Compound 1l+Compound 1m→Compound I-1

To a DMF (2 mL) solution of compound 1l (1.36 g, 1.00 mmol) was added sodium iodide (300 mg, 2.00 mmol), and the mixture was stirred at room temperature for 5 minutes. After cooled to 0° C., compound 1m (0.34 g, 1.10 mmol) was added, and the mixture was stirred at 0 to 10° C. for 7 hours. After DMF (6 mL) was added, the mixture was cooled to −40° C., phosphorus tribromide (189 μl, 2.00 mmol) was added, and the mixture was stirred at −40° C. for 30 minutes. The reaction mixture was slowly added to an ice-cooled 5% aqueous sodium chloride solution (20 ml) containing sodium thiosulfate (1 g). The precipitated solid was filtered, washed with water, suspended in water, and lyophilized to obtain compound 1n as a pale orange solid. The resulting compound 1n was used in the next reaction without purification.

The total amount of the resulting compound 1n was dissolved in dichloromethane (10 ml), and the solution was cooled to −40° C., anisole (1.092 ml, 10.0 mmol) and a 2 mol/L aluminum chloride/nitromethane solution (5.00 ml, 10.0 mmol) were sequentially added, and the mixture was stirred at 0° C. for 1 hour. The reaction solution was dissolved in water, 2 mol/L hydrochloric acid, and acetonitrile, and washed with diisopropyl ether. To the aqueous layer was added the HP20-SS resin, and acetonitrile was distilled off under reduced pressure. The resulting mixed solution was subjected to ODS column chromatography, and eluted with 20 mmol/L hydrochloric acid/acetonitrile. To fractions containing the desired compound was added the HP20-SS resin, and acetonitrile was distilled off under reduced pressure. The resulting mixed solution was subjected to HP20-SS column chromatography, and eluted with water/acetonitrile. The resulting solution was concentrated under reduced pressure, and lyophilized to obtain compound I-1 (204.2 mg, 22%) as a white powder.

$^1$H-NMR (D$_2$O) δ: 7.10 (1H, d, J=8.48 Hz), 7.02 (1H, s), 6.90 (1H, d, J=8.48 Hz), 5.82 (1H, d, J=4.95 Hz), 5.19 (1H, d, J=4.95 Hz), 4.94-4.92 (1H, m), 4.58 (1H, d, J=13.60 Hz), 4.07-3.72 (5H, m), 3.56 (1H, d, J=16.45 Hz), 3.04-2.80 (7H, m), 2.66-2.48 (2H, m), 2.30-2.11 (4H, m).

Elemental analysis: C31H35ClN8O10S2(H2O)8(HCl)0.1
Cal'd: C, 40.16; H, 5.56; Cl, 4.21; N, 12.09; S, 6.92(%).
Found: C, 40.13; H, 5.45; Cl, 4.17; N, 12.09; S, 7.22(%).

Example 2
Synthesis of Compound I-2
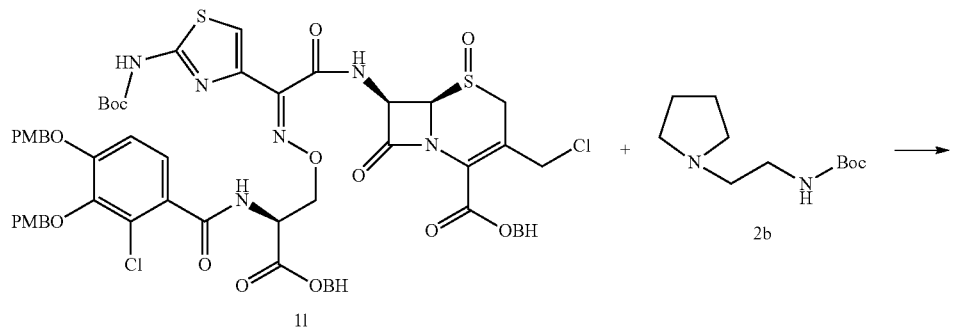
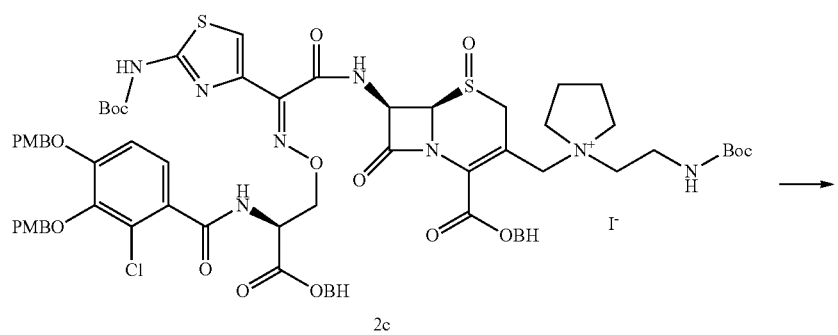
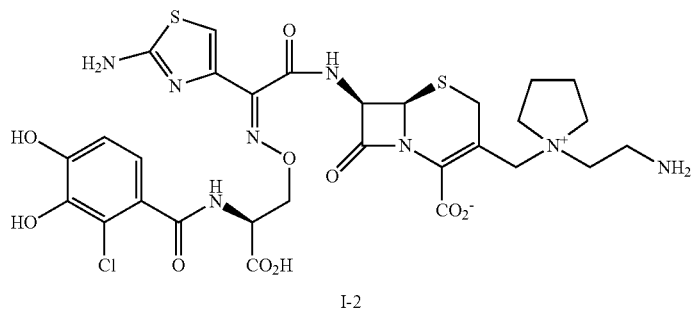
Step: Compound 11+Compound 2b→Compound I-2
Using compound 11 (1.36 g, 1.00 mmol) and compound 2b (236 mg, 1.10 mmol), the desired compound was synthesized as described in step 8 of Example 1.
Yield 226.1 mg, (26%)
$^1$H-NMR (D$_2$O) δ: 7.08 (1H, d, J=8.54 Hz), 7.00 (1H, s), 6.89 (1H, d, J=8.54 Hz), 5.82 (1H, d, J=4.80 Hz), 5.19 (1H, d, J=4.80 Hz), 4.68-4.66 (2H, m), 3.84 (1H, d, J=13.88 Hz), 3.64-3.39 (10H, m), 3.08 (1H, d, J=16.93 Hz), 2.23 (4H, br s).
Elemental analysis: C29H33ClN8O10S2(H2O)6.1
Cal'd: C, 40.36; H, 5.28; Cl, 4.11; N, 12.98; S, 7.43(%).
Found: C, 40.54; H, 5.15; Cl, 4.40; N, 12.98; S, 7.49(%).
Example 3
Synthesis of Compound I-3
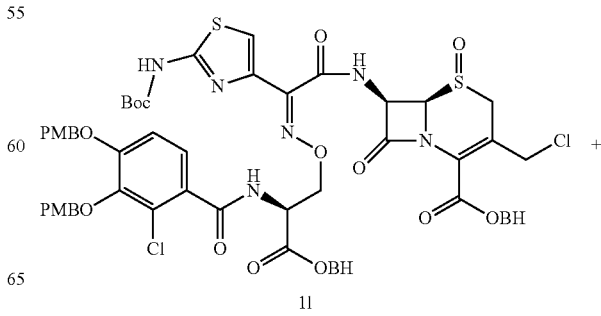

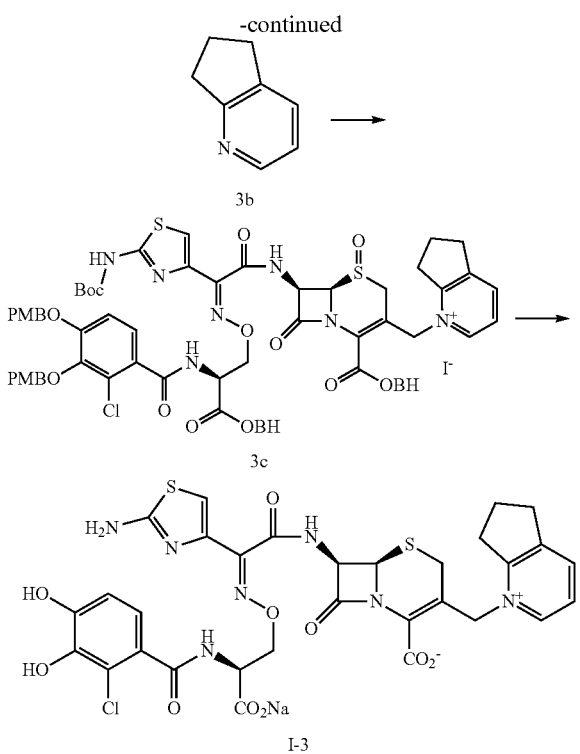

Step: Compound 1l+Compound 3b→Compound I-3

Using compound 1l (1.36 g, 1.00 mmol) and compound 3b (126 μl, 1.10 mmol), the desired compound was synthesized as described in step 8 of Example 1.

Yield: 471.5 mg, (42%)

$^1$H-NMR (D$_2$O) δ: 8.41 (1H, d, J=5.95 Hz), 8.18 (1H, d, J=7.63 Hz), 7.65 (1H, t, J=6.94 Hz), 7.01 (1H, d, J=8.24 Hz), 6.95 (1H, s), 6.77 (1H, d, J=8.24 Hz), 5.80 (1H, d, J=4.80 Hz), 5.41 (1H, d, J=15.17 Hz), 5.14 (1H, d, J=15.17 Hz), 5.08 (1H, d, J=4.80 Hz), 4.70-4.65 (1H, m), 4.61-4.55 (2H, m), 3.32-3.08 (5H, m), 2.78 (1H, d, J=17.69 Hz), 2.32-2.20 (2H, m).

Elemental analysis: C31H27ClN7O10S2Na(H2O)7.3

Cal'd: C, 40.84; H, 4.60; Cl, 3.89; N, 10.75; S, 7.03; Na, 2.52(%).

Found: C, 40.97; H, 4.53; Cl, 3.40; N, 10.77; S, 6.73; Na, 2.49(%).

Example 4

Synthesis of Compound I-4

[Formula 34]

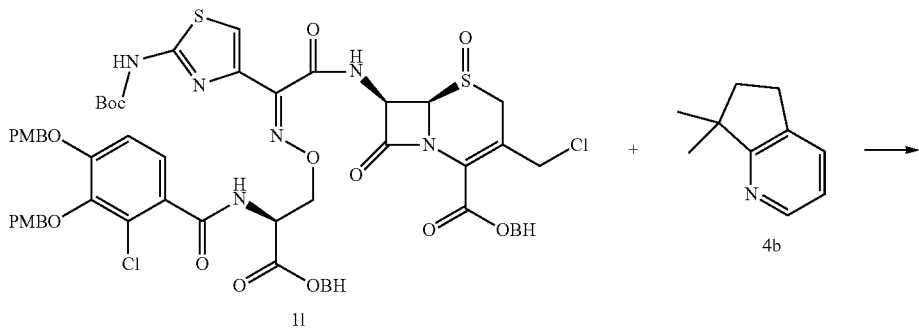

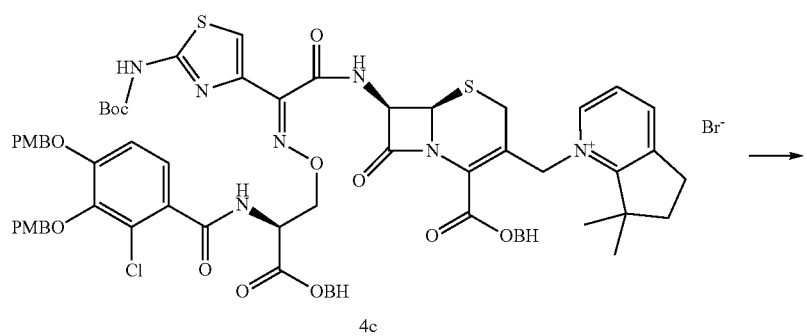

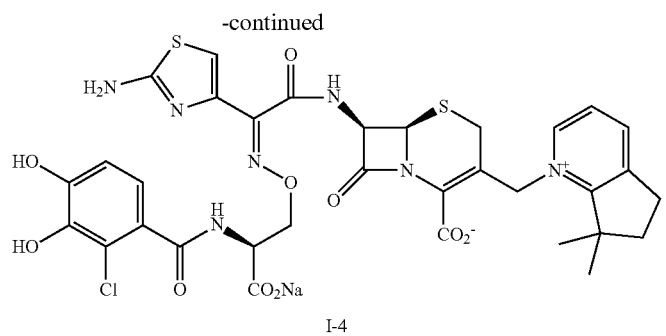

I-4

Step: Compound 11+Compound 4b→Compound I-4

To a DMF (1.5 mL) solution of compound 11 (1.23 g, 0.900 mmol) and compound 4b (132 mg, 0.900 mmol) synthesized referring to Bioorg. Med. Chem. Lett. 8 (1998) 453-458 was added sodium bromide (185 mg, 1.80 mmol), and the mixture was stirred at room temperature for 10 days. After DMF (4.5 mL) was added, the mixture was cooled to −40° C., phosphorus tribromide (170 µl, 1.80 mmol) was added, and the mixture was stirred at −40° C. for 30 minutes. The reaction mixture was slowly added to an ice-cooled 5% aqueous sodium chloride solution (20 ml) containing sodium thiosulfate (1 g). The precipitated solid was filtered, washed with water, suspended in water, and lyophilized to obtain compound 4c as a white solid. Using the resulting compound 4c, the desired compound was synthesized as described in step 8 of Example 1.

Yield 222.9 mg, (25%)

$^1$H-NMR (D$_2$O) δ: 8.37 (1H, d, J=6.56 Hz), 8.22 (1H, d, J=7.47 Hz), 7.62 (1H, t, J=6.86 Hz), 7.02-6.99 (2H, m), 6.77 (1H, d, J=8.39 Hz), 5.82 (1H, d, J=4.80 Hz), 5.38 (1H, d, J=14.95 Hz), 5.32 (1H, d, J=14.95 Hz), 5.17 (1H, d, J=4.80 Hz), 4.66-4.60 (3H, m), 3.34 (1H, d, J=17.69 Hz), 3.09 (2H, t, J=7.13 Hz), 2.75 (1H, d, J=17.69 Hz), 2.19 (2H, t, J=7.13 Hz), 1.53 (3H, s), 1.49 (3H, s).

Elemental analysis: C33H31ClN7O10S2Na(H2O)8 (NaHCO3)0.1

Cal'd: C, 41.38; H, 4.94; Cl, 3.69; N, 10.21; S, 6.68; Na, 2.63(%).

Found: C, 41.28; H, 4.76; Cl, 3.71; N, 10.39; S, 6.89; Na, 2.55(%).

Example 5

Synthesis of Compound I-5

[Formula 35]

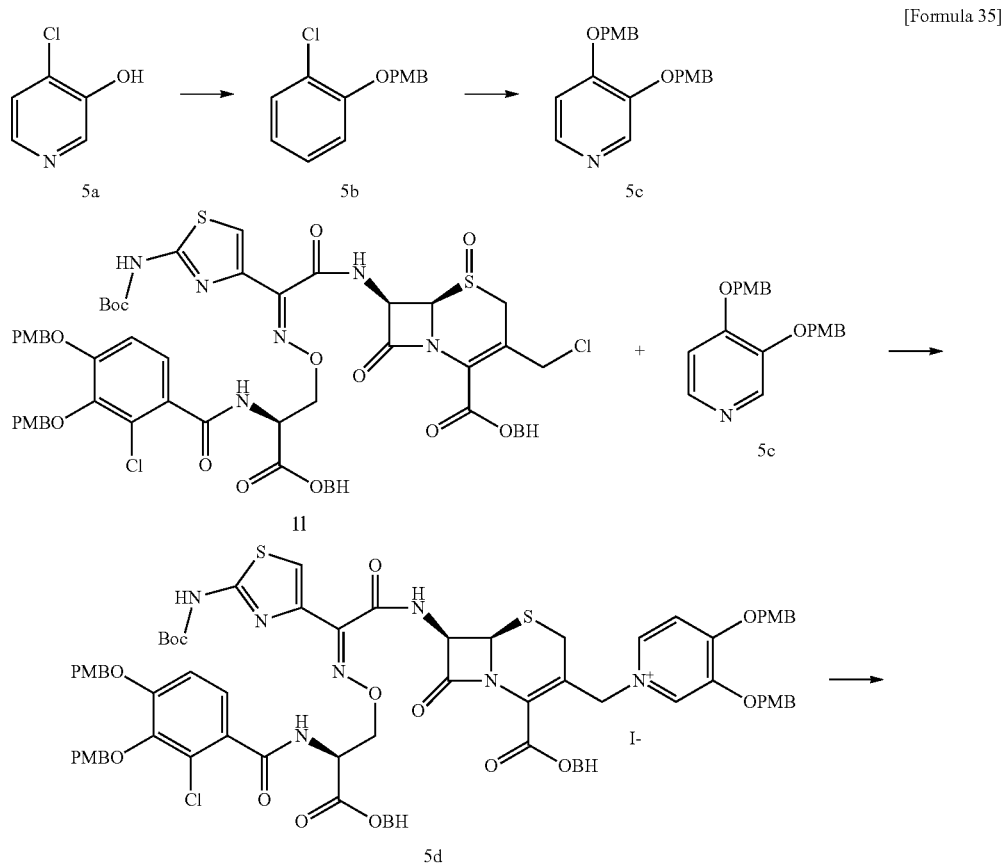

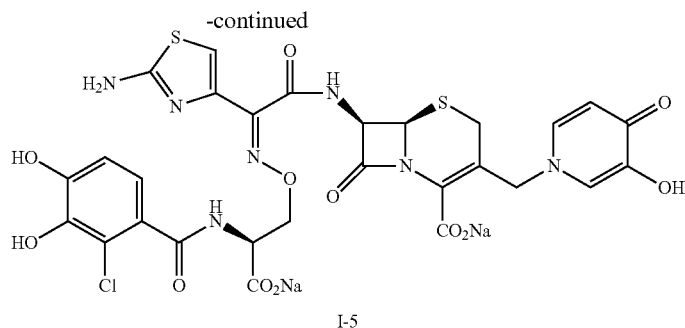

I-5

Step 1: Compound 5a→Compound 5b

To a tetrahydrofuran (100 ml) solution of compound 5a (10.00 g, 77 mmol) and 4-methoxybenzyl alcohol (11.53 ml, 93 mmol) were added dimethylazodicarboxylic acid (10.0 ml, 67.8 mmol) and a 2.7 mol/L dimethylazodicarboxylic acid/toluene solution (9.43 ml, 25.5 mmol) and triphenylphosphine (24.30 g, 93 mmol) under ice-cooling. After stirred at room temperature over night, a 2.7 mol/L dimethylazodicarboxylic acid/toluene solution (17.15 ml, 46.3 mmol) and triphenylphosphine (12.15 g, 46.3 mmol) were added, and the mixture was stirred at room temperature for 2 hours. After tetrahydrofuran was distilled off under reduced pressure, the reaction solution was diluted with dichloromethane, washed with an aqueous saturated sodium carbonate solution, and brine, and dried over magnesium sulfate. After magnesium sulfate was filtered, the filtrate was concentrated under reduced pressure, subjected to silica gel column chromatography, and eluted with hexane/ethyl acetate. Fractions containing the desired compound were concentrated under reduced pressure to obtain compound 5b (5.30 g, 28%).

$^1$H-NMR (CDCl$_3$) δ: 8.31 (1H, s), 8.14 (1H, d, J=4.96 Hz), 7.37 (2H, d, J=8.54 Hz), 7.31 (1H, d, J=4.96 Hz), 6.92 (2H, d, J=8.54 Hz), 5.17 (2H, s), 3.82 (3H, s).

Step 2: Compound 5b→Compound 5c

Sodium hydride (384 mg, 9.61 mmol) was suspended in DME (10 ml), and 4-methoxybenzyl alcohol (1.20 ml, 9.61 mmol) was added under ice-cooling. After stirred at room temperature for 30 minutes, a DME (10 ml) solution of compound 5b (2.00 g, 8.01 mmol) was added, the mixture was stirred overnight under heating at reflux. The reaction solution was diluted with ethyl acetate, washed with water, and brine, and dried over magnesium sulfate. After magnesium sulfate was filtered, the filtrate was concentrated under reduced pressure, subjected to silica gel column chromatography, and eluted with hexane/ethyl acetate. Fractions containing the desired compound were concentrated under reduced pressure to obtain compound 5c (1.34 g, 48%).

$^1$H-NMR (CDCl$_3$) δ: 8.17 (1H, s), 8.11 (1H, d, J=5.34 Hz), 7.35-7.30 (4H, m), 6.93-6.82 (5H, m), 5.12 (2H, s), 5.09 (2H, s), 3.82 (3H, s), 3.80 (3H, s).

Step 3: Compound 11+Compound 5c→Compound I-5

Using compound 11 (1.36 g, 1.00 mmol) and compound 5c (387 mg, 1.10 mmol), the desired compound was synthesized as described in step 8 of Example 1.

Yield 410.7 mg, (41%)

$^1$H-NMR (D$_2$O) δ: 7.67-7.62 (2H, m), 7.05-7.01 (2H, m), 6.82 (1H, d, J=8.39 Hz), 6.58 (1H, d, J=6.88 Hz), 5.81 (1H, d, J=4.78 Hz), 5.03 (1H, d, J=4.78 Hz), 4.91-4.88 (2H, m), 4.66-4.63 (2H, m), 3.11 (1H, d, J=17.71 Hz), 2.79 (1H, d, J=17.71 Hz).

Elemental analysis: C28H22ClN7O12S2Na2(H2O)9.1

Cal'd: C, 35.10; H, 4.23; Cl, 3.70; N, 10.23; S, 6.69; Na, 4.80(%).

Found: C, 35.08; H, 4.12; Cl, 3.74; N, 10.22; S, 6.72; Na, 4.88(%).

Example 6

Synthesis of Compound I-6

[Formula 36]

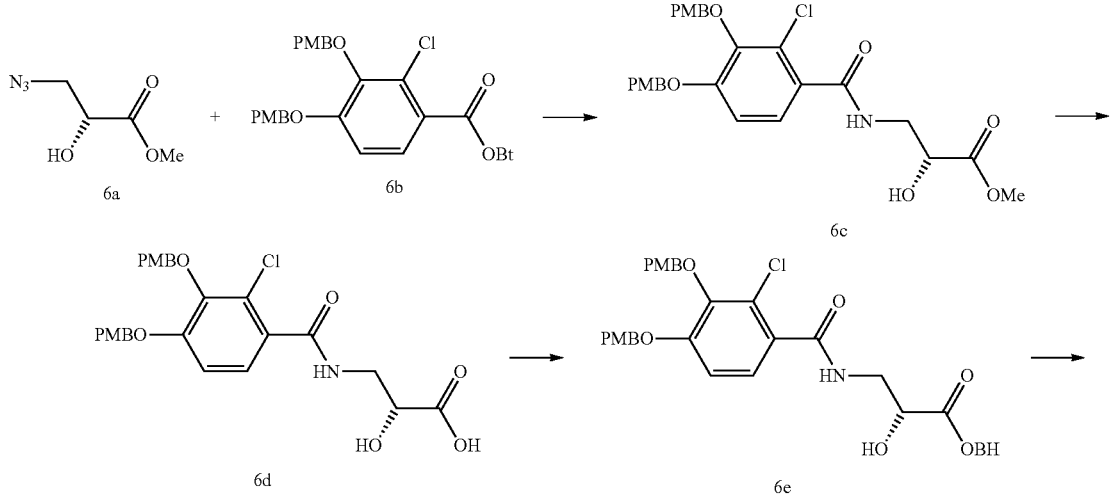

-continued
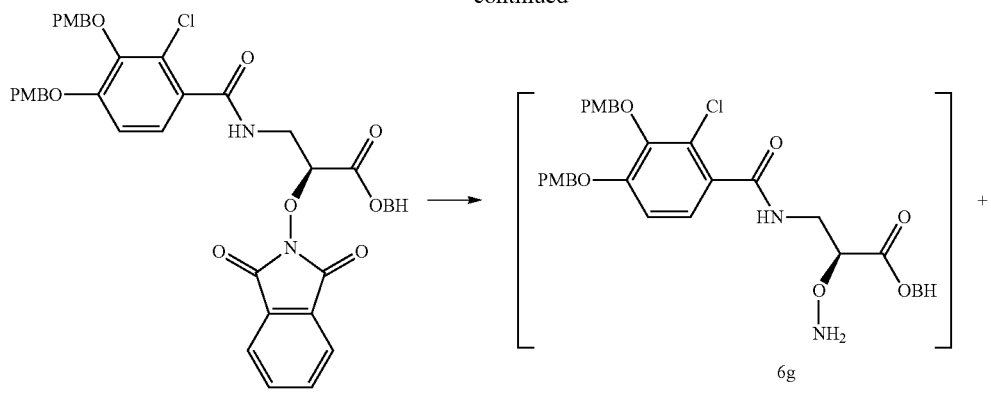
6f
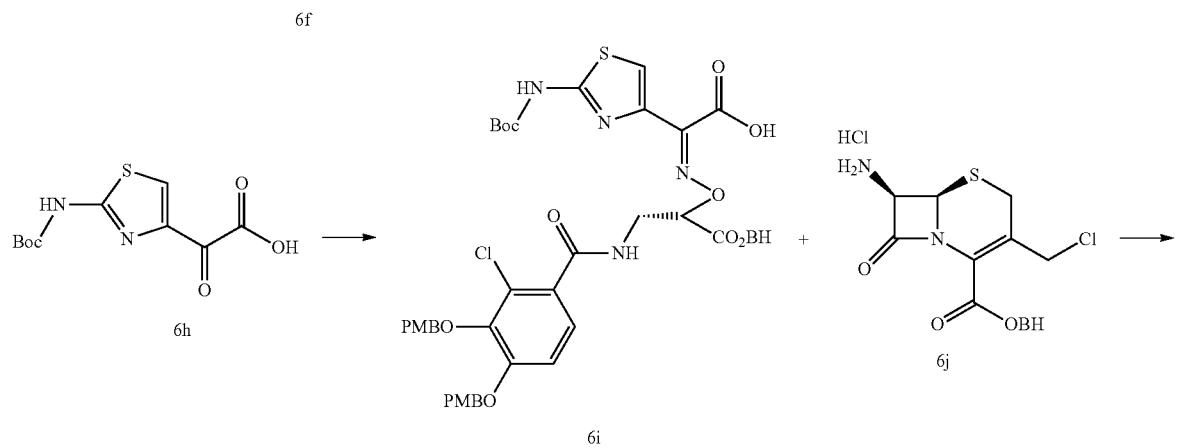
6h
6i
6j
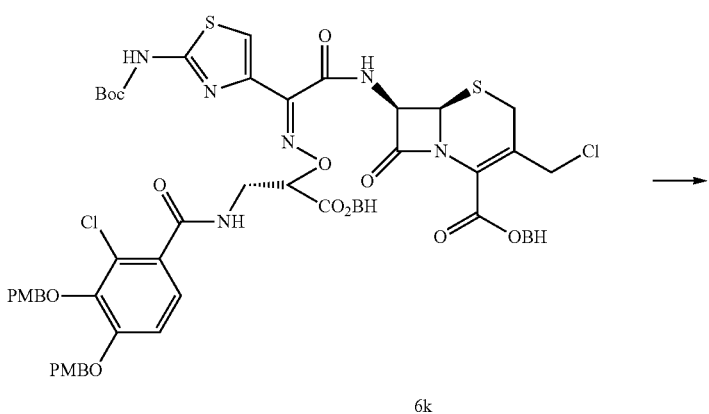
6k
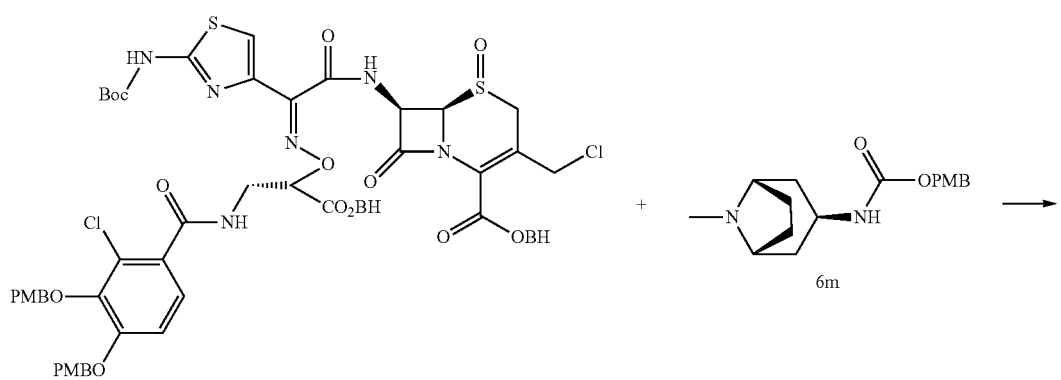
6l
6m

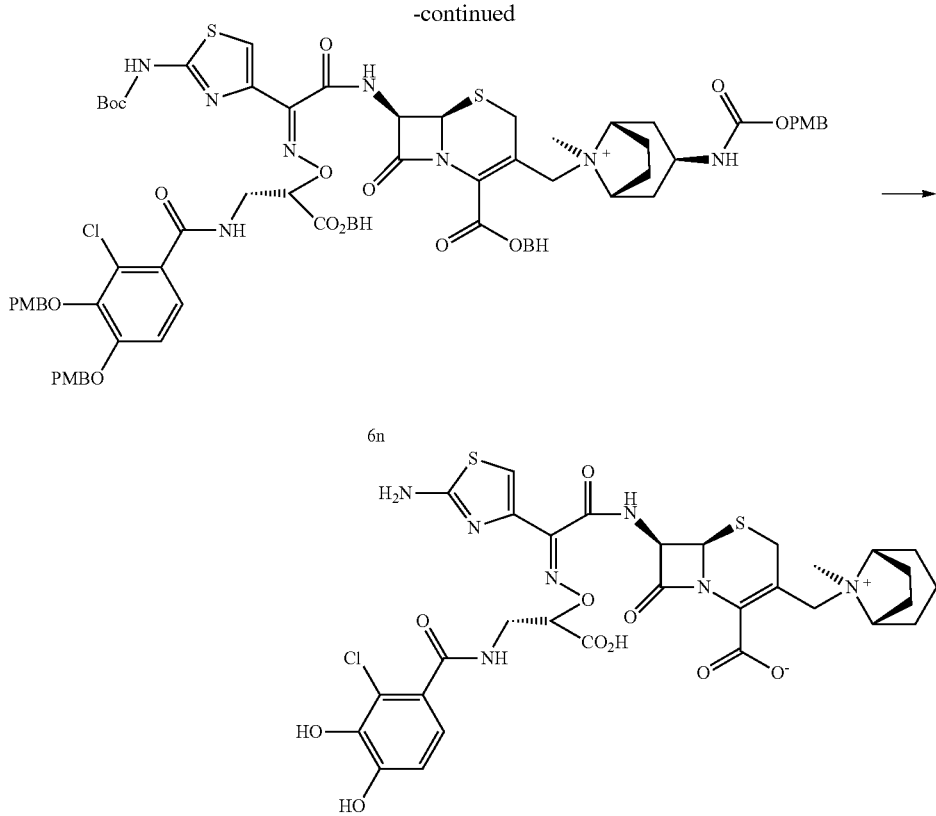

I-6

Step 1: Compound 6a+Compound 6b→Compound 6c

To a DMF (400 ml)/water (40 ml) solution of compound 6a (8.68 g, 59.8 mmol) and compound 6b (39.2 g, 71.8 mmol) which had been synthesized according to WO2006/127961 was added triphenylphosphine (20.39 g, 78 mmol) under ice-cooling, and the mixture was stirred at room temperature overnight. The reaction solution was concentrated under reduced pressure to obtain compound 6c (89.89 g). Compound 6c was used in the next reaction without purification.

Step 2: Compound 6c→Compound 6d

To a tetrahydrofuran (500 ml)/methanol (100 ml) of compound 6c (corresponding to 59.8 mmol) was added a 8 mol/L aqueous sodium hydroxide solution (14.95 ml, 120 mmol), and the mixture was stirred at room temperature for 3 hours. Further, an 8 mol/L aqueous sodium hydroxide solution (7.48 ml, 59.8 mmol) was added, and the mixture was stirred at room temperature for 1 hour. Under ice-cooling, water (100 ml), and 2 mol/L hydrochloric acid (100 ml) were sequentially added, tetrahydrofuran was distilled off under reduced pressure and, thereafter, the precipitated solid was filtered to obtain compound 6d (24.78 g, 80%). Compound 6d was used in the next reaction without purification.

$^1$H-NMR (DMSO-$d_6$) δ: 8.28 (1H, t, J=5.72 Hz), 7.42 (2H, d, J=8.54 Hz), 7.31 (2H, d, J=8.54 Hz), 7.19 (1H, d, J=8.62 Hz), 7.14 (1H, d, J=8.62 Hz), 6.97 (2H, d, J=8.54 Hz), 6.86 (2H, d, J=8.54 Hz), 5.14 (2H, s), 4.87 (2H, s), 4.13 (1H, dd, J=6.71, 5.20 Hz), 3.76 (3H, s), 3.74 (3H, s), 3.51 (1H, dt, J=13.27, 5.20 Hz), 3.40-3.31 (1H, m).

Step 3: Compound 6d→Compound 6e

Using compound 6d (24.78 g, 48.0 mmol), the desired compound was synthesized as described in step 1 of Example 1, subjected to silica gel column chromatography, and eluted with chloroform/ethyl acetate.

Yield 21.44 g, (65%)

$^1$H-NMR (CDCl$_3$) δ: 7.35-7.26 (13H, m), 7.24-7.18 (2H, m), 6.94-6.80 (6H, m), 6.59 (1H, t, J=5.49 Hz), 5.07 (2H, s), 4.92 (2H, s), 4.51 (1H, td, J=5.33, 3.70 Hz), 3.98 (1H, ddd, J=13.92, 5.49, 3.70 Hz), 3.86-3.77 (7H, m), 3.56 (1H, d, J=5.28 Hz).

Step 4: Compound 6e→Compound 6f

Using compound 6e (20.44 g, 30.0 mmol), N-hydroxyphthalimide (6.35 g, 39.0 mmol), diisopropylazodicarboxylic acid (7.57 ml, 39.0 mmol), and triphenylphosphine (10.22 g, 39.0 mmol), the desired compound was synthesized as described in step 2 of Example 1, subjected to silica gel column chromatography, and eluted with chloroform/ethyl acetate.

Yield 19.73 g, (80%)

$^1$H-NMR (CDCl$_3$) δ: 7.80-7.72 (4H, m), 7.37-7.20 (16H, m), 6.93-6.81 (6H, m), 5.08 (2H, s), 5.03 (1H, dd, J=5.87, 4.65 Hz), 4.94 (2H, s), 4.07-4.03 (2H, m), 3.83 (3H, s), 3.79 (3H, s).

Step 5: Compound 6f→Compound 6g+Compound 6h→Compound 6i

Using compound 6f (10.0 g. 12.1 mmol), the desired compound was synthesized as described in step 3 of Example 1, the reaction solution was diluted with dichloromethane, and the organic layer was washed with water, and brine, and dried over magnesium sulfate. After magnesium sulfate was filtered, the filtrate was concentrated under reduced pressure to obtain compound 6i (11.95 g). Compound 6i was used in the next reaction without purification.

Step 6: Compound 6i+Compound 6j→Compound 6k

Using compound 6i (corresponding to 12.1 mmol), the desired compound was synthesized as described in step 6 of Example 1.

Yield 11.81 g, (72%)

$^1$H-NMR (CDCl$_3$) δ: 8.46 (1H, d, J=9.00 Hz), 8.13 (1H, br s), 7.52 (2H, d, J=6.71 Hz), 7.43-7.21 (25H, m), 6.95-6.76 (6H, m), 6.51 (1H, d, J=8.69 Hz), 5.90 (1H, dd, J=9.07, 4.96 Hz), 5.30 (1H, dd, J=5.34, 2.59 Hz), 4.89-4.75 (3H, m), 4.66 (2H, s), 4.44-4.35 (1H, m), 4.02 (1H, d, J=11.90 Hz), 3.84-3.75 (8H, m), 3.42 (1H, d, J=18.53 Hz), 3.00 (1H, d, J=18.53 Hz), 1.54 (9H, s).

Step 7: Compound 6k→Compound 6l

Using compound 6k (11.81 g, 8.76 mmol), the desired compound was synthesized as described in step 7 of Example 1.

Yield 10.75 g, (90%)

$^1$H-NMR (CDCl$_3$) δ: 8.22 (1H, br s), 7.78 (1H, d, J=9.91 Hz), 7.41-7.12 (26H, m), 6.93-6.76 (7H, m), 6.11 (1H, dd, J=9.91, 4.88 Hz), 5.25-5.22 (1H, m), 4.97-4.81 (5H, m), 4.46 (1H, d, J=3.66 Hz), 4.19-3.97 (3H, m), 3.82-3.74 (7H, m), 3.53 (1H, d, J=18.53 Hz), 3.16 (1H, d, J=18.53 Hz), 1.53 (9H, s).

Step 8: Compound 6l+Compound 6m→Compound I-6

Using compound 6l (1.36 g, 1.00 mmol) and compound 6m (335 mg, 1.10 mmol), the desired compound was synthesized as described in step 8 of Example 1.

Yield 142.1 mg, (15%)

$^1$H-NMR (D$_2$O) δ: 7.02 (1H, s), 7.00 (1H, d, J=8.24 Hz), 6.88 (1H, d, J=8.24 Hz), 5.79 (1H, d, J=4.88 Hz), 5.26 (1H, d, J=4.88 Hz), 3.99-3.70 (6H, m), 3.05-2.77 (7H, m), 2.63-2.51 (2H, m), 2.30-2.09 (4H, m).

Elemental analysis: C31H35ClN8O10S2(H2O)7.9

Cal'd: C, 40.40; H, 5.56; Cl, 3.85; N, 12.16; S, 6.96(%).

Found: C, 40.42; H, 5.37; Cl, 3.99; N, 12.03; S, 6.90(%).

Example 7

Synthesis of Compound I-7

[Formula 37]

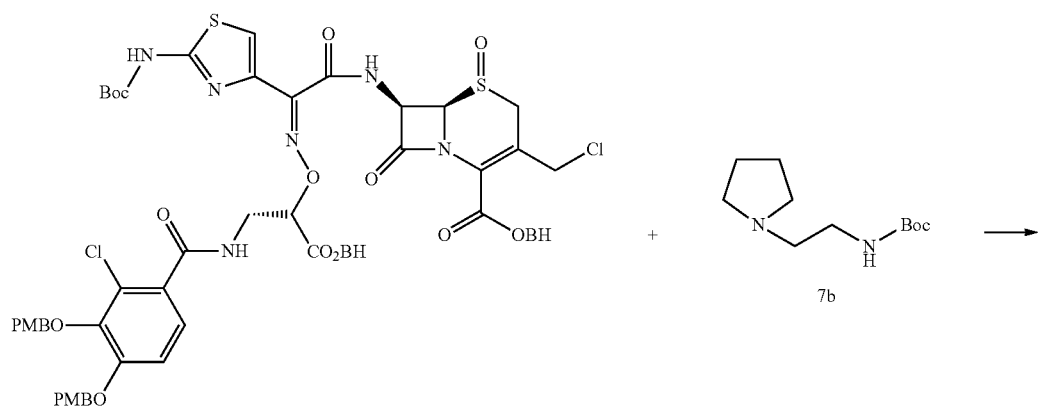

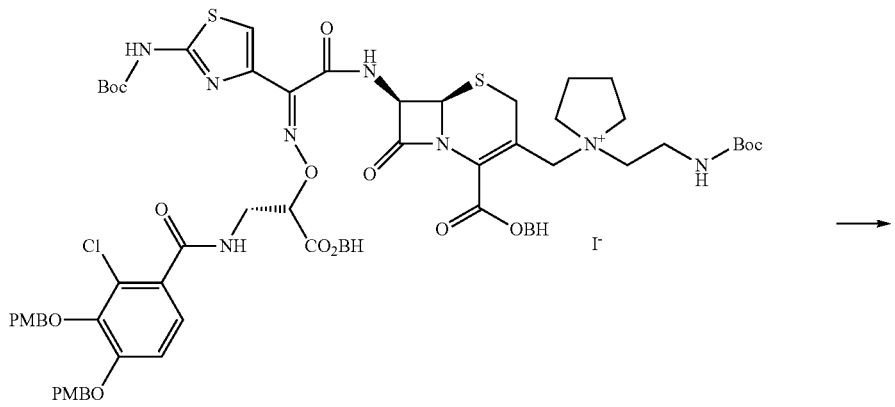

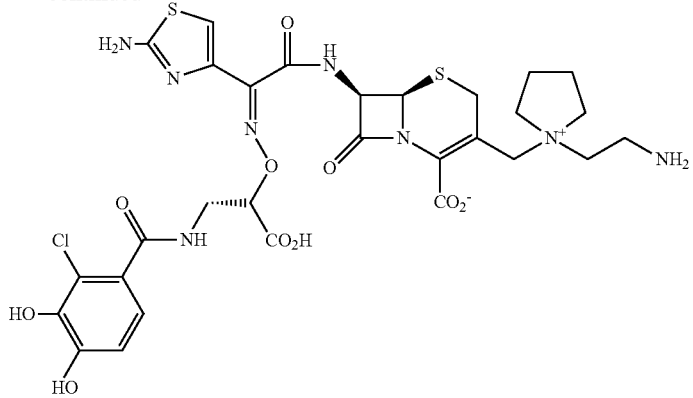

I-7

Step: Compound 6l+Compound 7b→Compound I-7

Using compound 6l (1.36 g, 1.00 mmol) and compound 7b (236 mg, 1.10 mmol), the desired compound was synthesized as described in step 8 of Example 1.

Yield 277.0 mg, (32%)

$^1$H-NMR (D$_2$O) δ: 7.02 (1H, s), 6.98 (1H, d, J=8.24 Hz), 6.87 (1H, d, J=8.24 Hz), 5.80 (1H, d, J=5.11 Hz), 5.26 (1H, d, J=5.11 Hz), 3.88-3.38 (12H, m), 3.09 (1H, d, J=17.08 Hz), 2.22 (4H, br s).

Elemental analysis: C29H33ClN8O10S2(H2O)6.2

Cal'd: C, 40.27; H, 5.29; Cl, 4.10; N, 12.96; S, 7.41(%).

Found: C, 40.21; H, 5.18; Cl, 4.07; N, 13.04; S, 7.40(%).

Example 8

Synthesis of Compound I-8

[Formula 38]

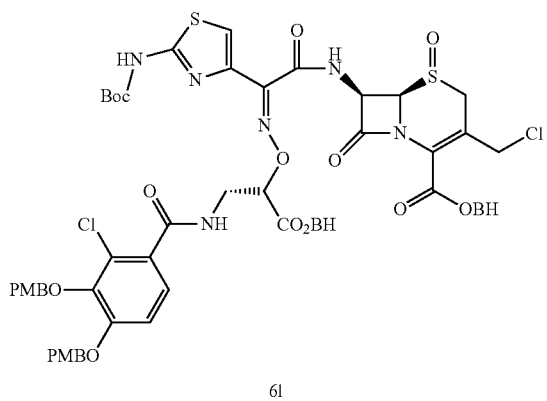

61

+

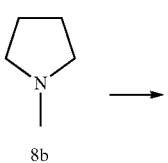

8b

→

8c

I-8

Step: Compound 6l+Compound 8b→Compound I-8

Using compound 6l (1.36 g, 1.00 mmol) and compound 8b (104 μg, 1.00 mmol), the desired compound was synthesized as described in step 8 of Example 1.

Yield 440.4 mg, (47%)

$^1$H-NMR (D$_2$O) δ: 7.04 (1H, s), 6.99 (1H, d, J=8.31 Hz), 6.88 (1H, d, J=8.31 Hz), 5.81 (1H, d, J=4.95 Hz), 5.25 (1H, d, J=4.95 Hz), 4.92-4.85 (1H, m), 4.69 (1H, d, J=11.25 Hz), 3.94-3.67 (4H, m), 3.51-3.45 (4H, m), 3.01 (1H, d, J=16.95 Hz), 2.94 (3H, s), 2.28-2.17 (4H, m).

Elemental analysis: C28H29ClN7O10S2Na(H2O)7.2 (NaHCO3)0.06

Cal'd: C, 38.26; H, 4.97; Cl, 4.02; N, 11.13; S, 7.28; Na, 2.77(%).

Found: C, 38.07; H, 5.03; Cl, 3.92; N, 11.36; S, 7.13; Na, 2.78(%).

Example 9
Synthesis of Compound I-9
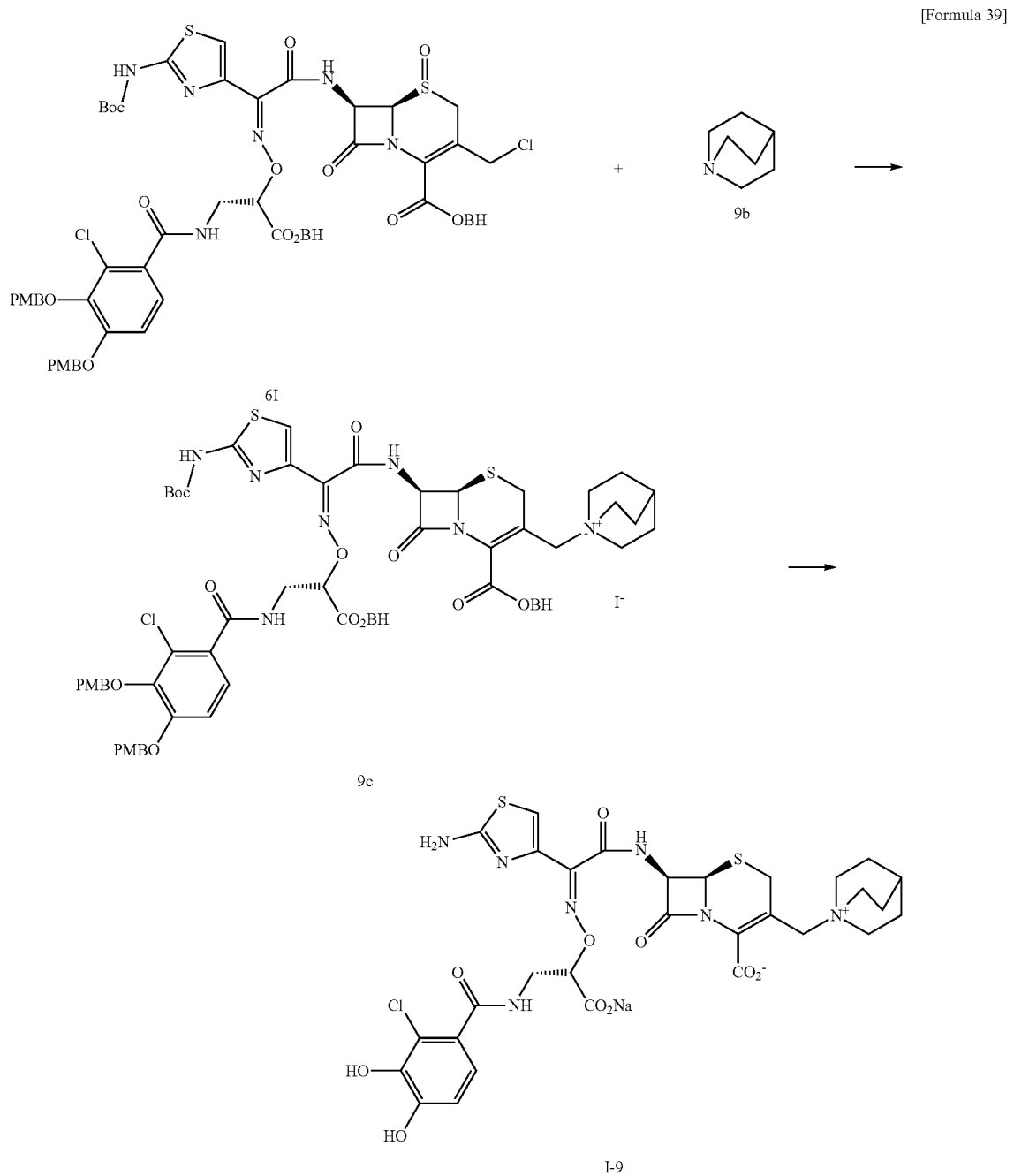
[Formula 39]
Step: Compound 6l+Compound 9b→Compound 9c
Using compound 6l (1.36 g, 1.00 mmol) and compound 9b (111 mg, 1.00 mmol), the desired compound was synthesized as described in step 8 of Example 1.
Yield 238.0 mg, (25%)
$^1$H-NMR (D$_2$O) δ: 7.03 (1H, s), 6.99 (1H, d, J=8.39 Hz), 6.88 (1H, d, J=8.39 Hz), 5.81 (1H, d, J=4.95 Hz), 5.24 (1H, d, J=4.95 Hz), 4.91-4.86 (1H, m), 4.49 (1H, d, J=13.93 Hz), 3.96-3.74 (2H, m), 3.66 (1H, d, J=16.79 Hz), 3.58 (1H, d, J=13.93 Hz), 3.44-3.26 (6H, m), 2.95 (1H, d, J=16.79 Hz), 2.20-2.16 (1H, m), 2.00-1.95 (6H, m).
Elemental analysis: C30H31ClN7O10S2Na(H2O)8.6
Cal'd: C, 38.86; H, 5.24; Cl, 3.82; N, 10.58; S, 6.92; Na, 2.48(%).
Found: C, 38.82; H, 5.10; Cl, 3.76; N, 10.61; S, 6.85; Na, 2.53(%).

Example 10
Synthesis of Compound I-10
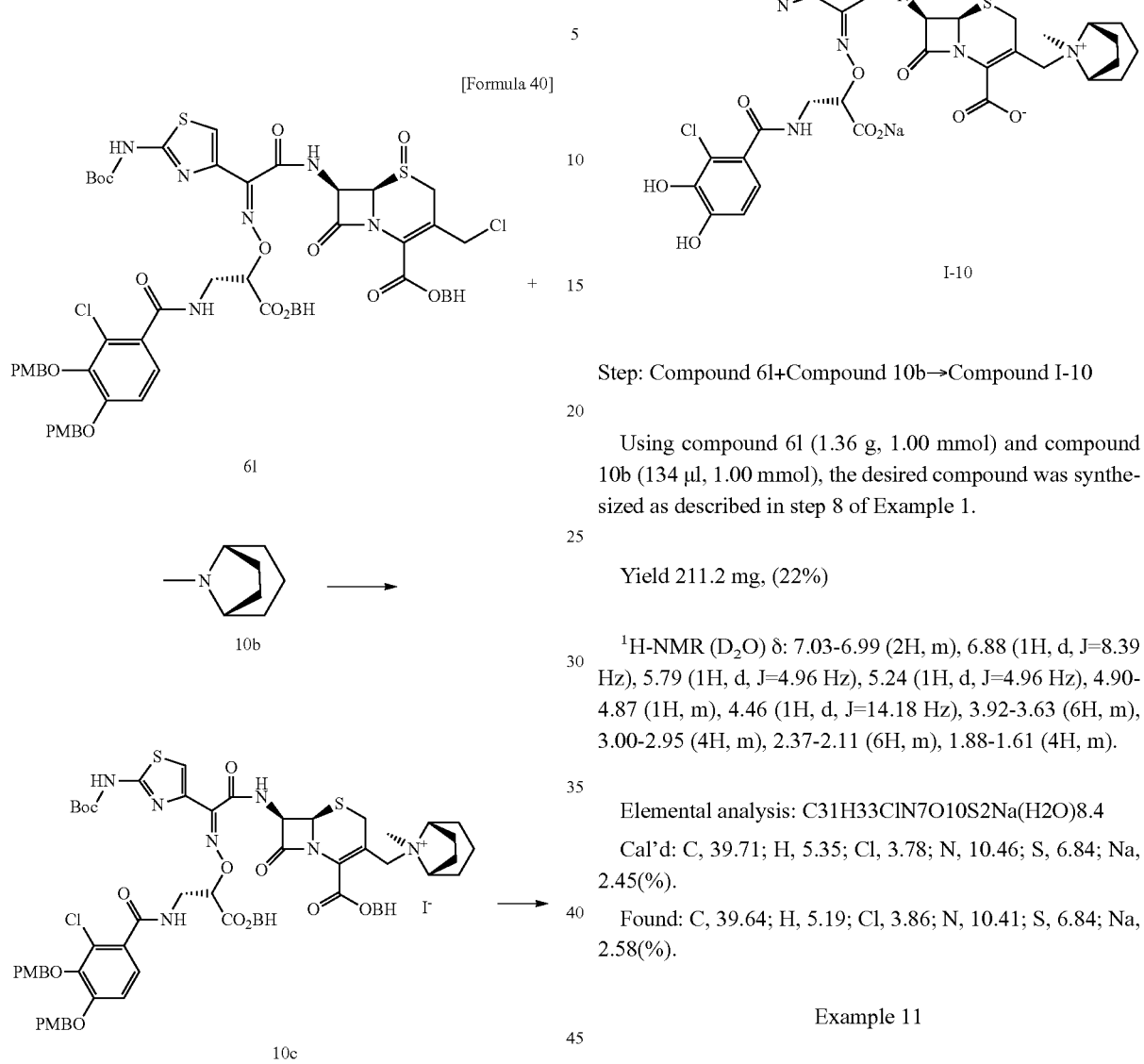
Step: Compound 6l+Compound 10b→Compound I-10
Using compound 6l (1.36 g, 1.00 mmol) and compound 10b (134 μl, 1.00 mmol), the desired compound was synthesized as described in step 8 of Example 1.
Yield 211.2 mg, (22%)
$^1$H-NMR (D$_2$O) δ: 7.03-6.99 (2H, m), 6.88 (1H, d, J=8.39 Hz), 5.79 (1H, d, J=4.96 Hz), 5.24 (1H, d, J=4.96 Hz), 4.90-4.87 (1H, m), 4.46 (1H, d, J=14.18 Hz), 3.92-3.63 (6H, m), 3.00-2.95 (4H, m), 2.37-2.11 (6H, m), 1.88-1.61 (4H, m).
Elemental analysis: C31H33ClN7O10S2Na(H2O)8.4
Cal'd: C, 39.71; H, 5.35; Cl, 3.78; N, 10.46; S, 6.84; Na, 2.45(%).
Found: C, 39.64; H, 5.19; Cl, 3.86; N, 10.41; S, 6.84; Na, 2.58(%).
Example 11
Synthesis of Compound I-11
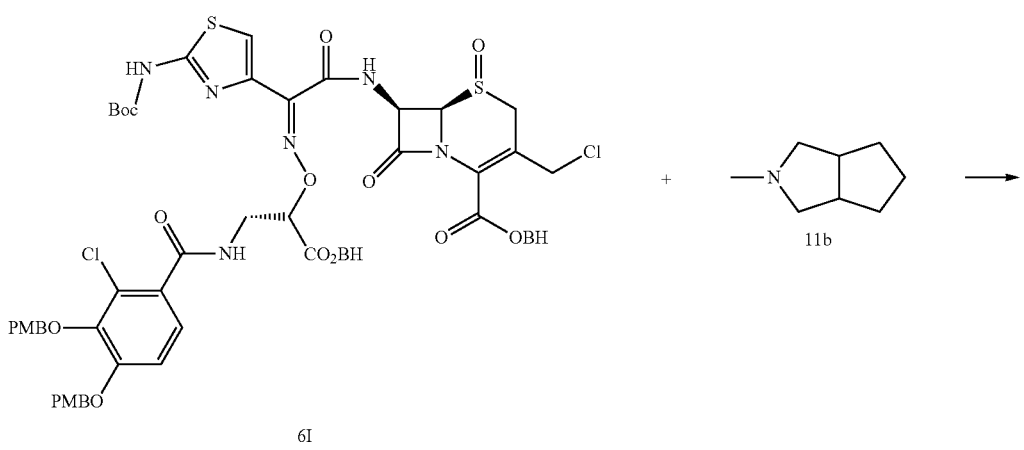

-continued

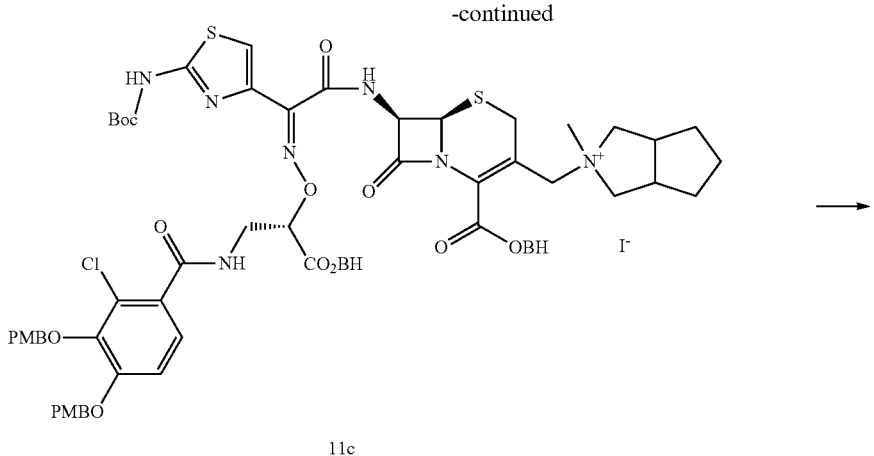

11c

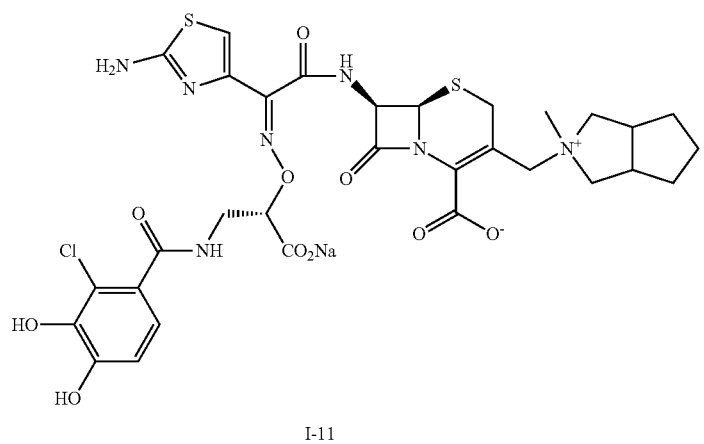

I-11

Step: Compound 6l+Compound 11b→Compound I-11

Using compound 6l (1.36 g, 1.00 mmol), and compound 11b (138 mg, 1.10 mmol) which was synthesized referring to J. Org. Chem. 1959, 24, 7-11, the desired compound was synthesized as described in step 8 of Example 1.

Yield 215.7 mg, (21%)

$^1$H-NMR (D$_2$O) δ: 7.04-6.99 (2H, m), 6.89 (1H, d, J=8.39 Hz), 5.79 (1H, d, J=4.87 Hz), 5.26 (1H, d, J=4.87 Hz), 4.90-4.87 (1H, m), 4.64 (1H, d, J=13.93 Hz), 3.88-3.71 (5H, m), 3.60 (1H, d, J=13.93 Hz), 3.05-2.88 (8H, m), 1.78-1.57 (6H, m).

Elemental analysis: C31H33ClN7O10S2Na(H2O)8.1 (NaHCO3)0.04

Cal'd: C, 39.85; H, 5.31; Cl, 3.79; N, 10.48; S, 6.86; Na, 2.56(%).

Found: C, 39.82; H, 5.30; Cl, 3.88; N, 10.57; S, 6.84; Na, 2.55(%).

Example 12

Synthesis of Compound I-12

[Formula 42]

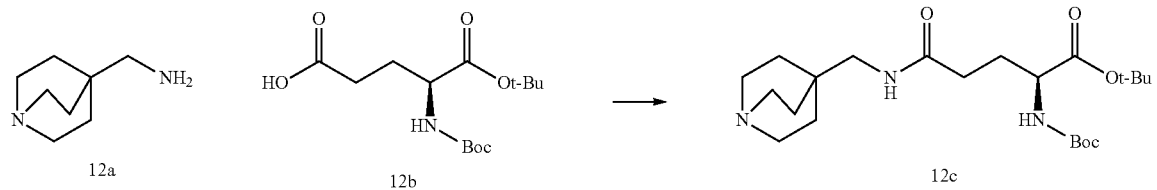

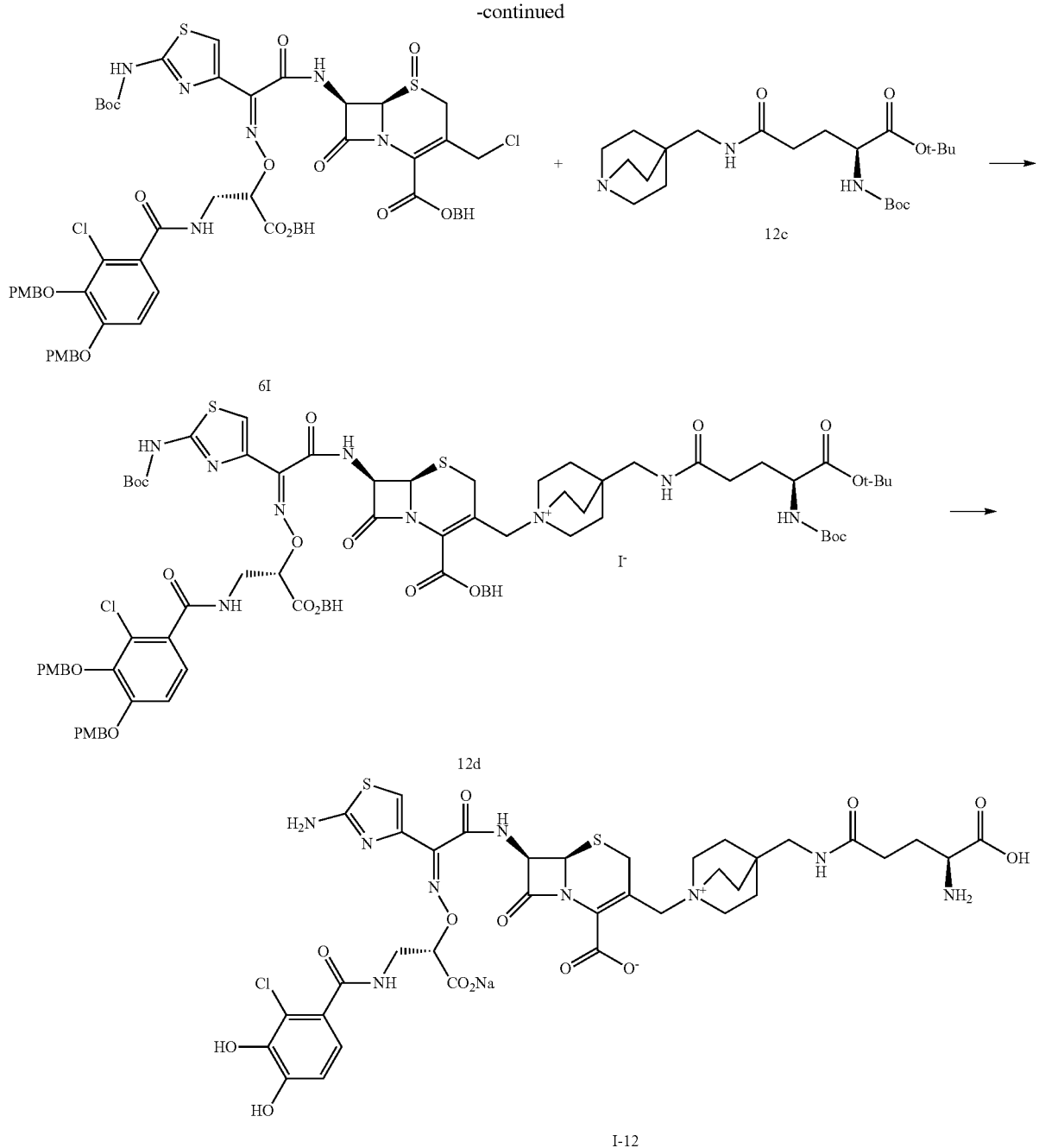

Step 1: Compound 12a+Compound 12b→Compound 12c

To a tetrahydrofuran (20 ml) solution of compound 12a (701 mg, 5.0 mmol) and compound 12b (1.67 g, 5.5 mmol) was added HATU (2.28 g, 6.0 mmol) under ice-cooling, and the mixture was stirred at room temperature overnight. The reaction solution was diluted with ethyl acetate, and the organic layer was washed with an aqueous sodium hydroxide solution, water and brine, and dried over magnesium sulfate. After magnesium sulfate was filtered, the filtrate was concentrated under reduced pressure to obtain compound 12c (1.57 g, 74%). Compound 12c was used in the next reaction without purification.

$^1$H-NMR (DMSO-$d_6$) δ: 7.68 (1H, t, J=6.04 Hz), 7.08 (1H, d, J=7.42 Hz), 3.80-3.72 (1H, m), 2.86-2.74 (8H, m), 2.17 (2H, t, J=7.55 Hz), 1.95-1.65 (2H, m), 1.42-1.26 (24H, m).

Step 2: Compound 6l+Compound 12c→Compound I-12

Using compound 6l (1.36 g, 1.00 mmol) and compound 12c (426 mg, 1.00 mmol), the desired compound was synthesized as described in step 8 of Example 1.

Yield 318.6 mg, (27%)

$^1$H-NMR (D$_2$O) δ: 7.03 (1H, s), 6.98 (1H, d, J=8.08 Hz), 6.87 (1H, d, J=8.08 Hz), 5.80 (1H, d, J=4.73 Hz), 5.23 (1H, d, J=4.73 Hz), 4.51 (1H, d, J=11.90 Hz), 3.89-3.62 (5H, m), 3.49-3.18 (9H, m), 3.01-2.93 (2H, m), 2.49-2.43 (1H, m), 2.17-2.10 (2H, m), 1.97-1.82 (6H, m).

Elemental analysis: C36H41ClN9O13S2Na(H2O)10.3

Cal'd: C, 38.75; H, 5.56; Cl, 3.18; N, 11.30; S, 5.75; Na, 2.06(%).

Found: C, 38.73; H, 5.41; Cl, 3.24; N, 11.30; S, 5.69; Na, 2.10(%).

Example 13
Synthesis of Compound I-13
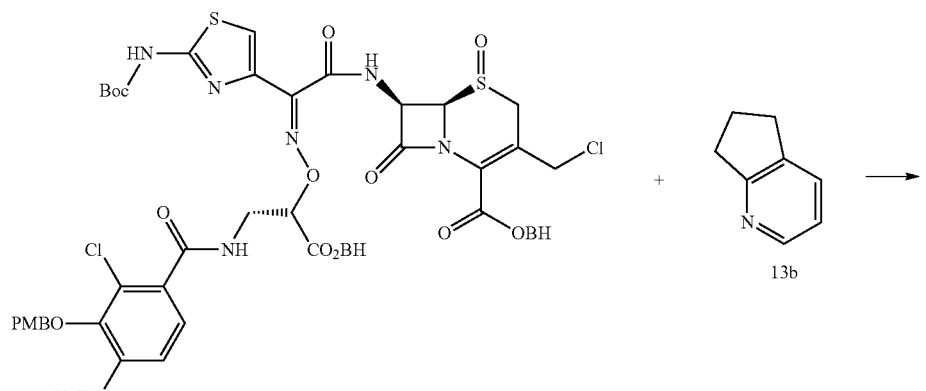
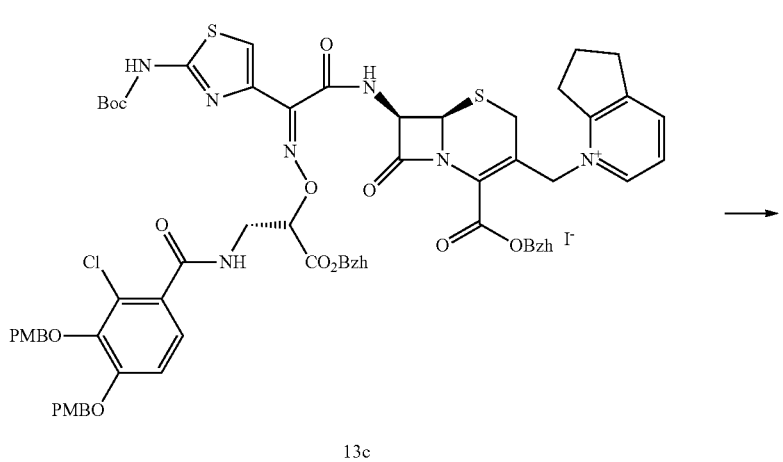
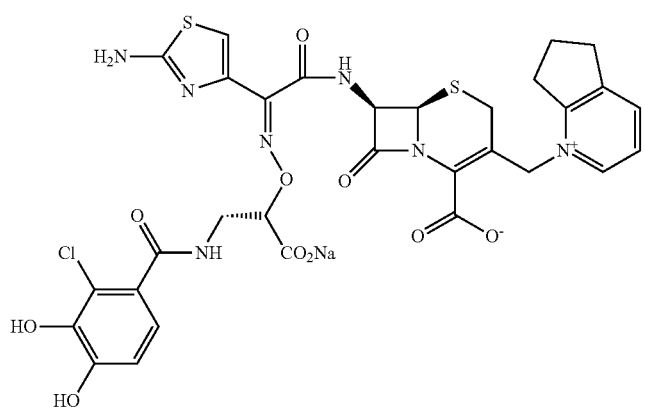
Step: Compound 6l+Compound 13b→Compound I-13
Using compound 6l (1.36 g, 1.00 mmol) and compound 13b (126 μl, 1.10 mmol), the desired compound was synthesized as described in step 8 of Example 1.
Yield 643.7 mg, (69%)
$^1$H-NMR (D$_2$O) δ: 8.45 (1H, d, J=6.10 Hz), 8.23 (1H, d, J=7.02 Hz), 7.63 (1H, t, J=6.79 Hz), 7.02 (1H, s), 6.93 (1H, d, J=7.93 Hz), 6.80 (1H, d, J=7.93 Hz), 5.79 (1H, d, J=4.88 Hz), 5.34 (1H, d, J=15.25 Hz), 5.22 (1H, d, J=15.25 Hz), 5.17 (1H, d, J=4.88 Hz), 3.82-3.79 (2H, m), 3.39-3.28 (3H, m), 3.18 (2H, t, J=7.47 Hz), 2.84 (1H, d, J=16.78 Hz), 2.36-2.26 (2H, m).
Elemental analysis: C31H27ClN7O10S2Na(H2O)7.7
Cal'd: C, 40.52; H, 4.65; Cl, 3.86; N, 10.67; S, 6.98; Na, 2.50(%).
[Formula 43]

Found: C, 40.46; H, 4.49; Cl, 3.82; N, 10.93; S, 6.91; Na, 2.52 (%).

Example 14

Synthesis of Compound I-14

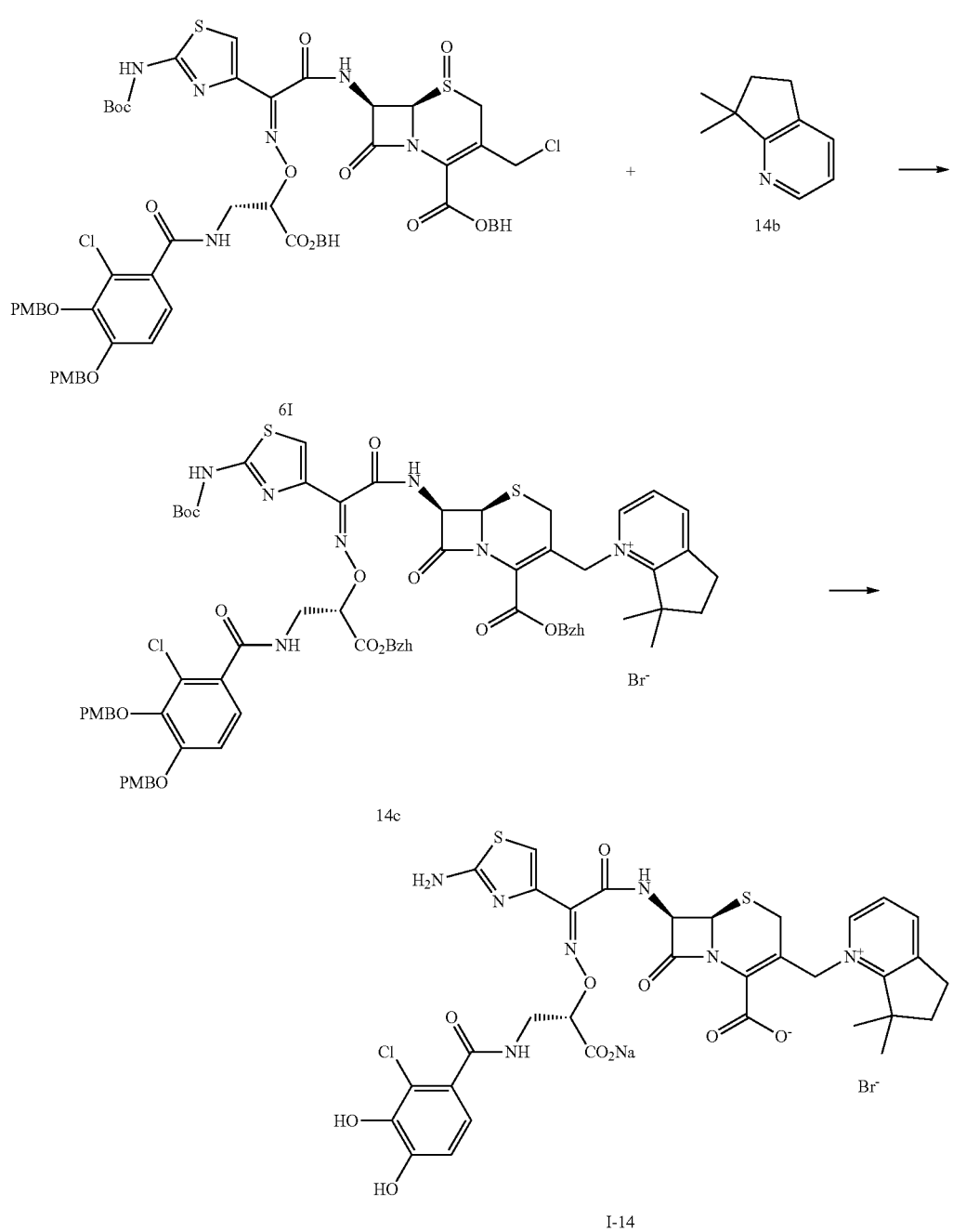

[Formula 44]

Step: Compound 6l+Compound 14b→Compound I-14

Using compound 6l (1.23 g, 0.900 mmol) and compound 14b (132 mg, 0.900 mmol), the desired compound was synthesized as Example 4.

Yield 225.1 mg, (24%)

$^1$H-NMR (D$_2$O) δ: 8.38 (1H, d, J=6.10 Hz), 8.22 (1H, d, J=7.78 Hz), 7.60 (1H, t, J=7.02 Hz), 7.02 (1H, s), 6.95 (1H, d, J=8.39 Hz), 6.79 (1H, d, J=8.39 Hz), 5.79 (1H, d, J=4.96 Hz), 5.40 (1H, d, J=14.87 Hz), 5.31 (1H, d, J=14.87 Hz), 5.24 (1H, d, J=4.96 Hz), 3.82-3.79 (2H, m), 3.51 (1H, d, J=17.84 Hz), 3.10 (2H, t, J=7.40 Hz), 2.75 (1H, d, J=17.84 Hz), 2.20 (2H, t, J=7.40 Hz), 1.54 (3H, s), 1.49 (3H, s).

Elemental analysis: C33H31ClN7O10S2Na(H2O)8.7 (NaHCO3)0.1

Cal'd: C, 40.84; H, 5.02; Cl, 3.64; N, 10.07; S, 6.59; Na, 2.60(%).

Found: C, 40.71; H, 4.83; Cl, 3.68; N, 10.19; S, 6.77; Na, 2.62(%).

Example 15
Synthesis of I-15
[Formul 45]
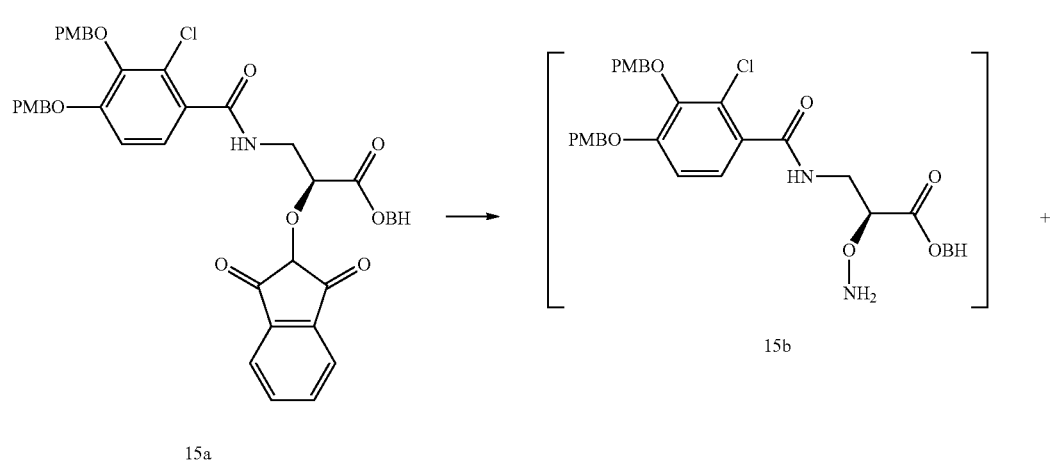
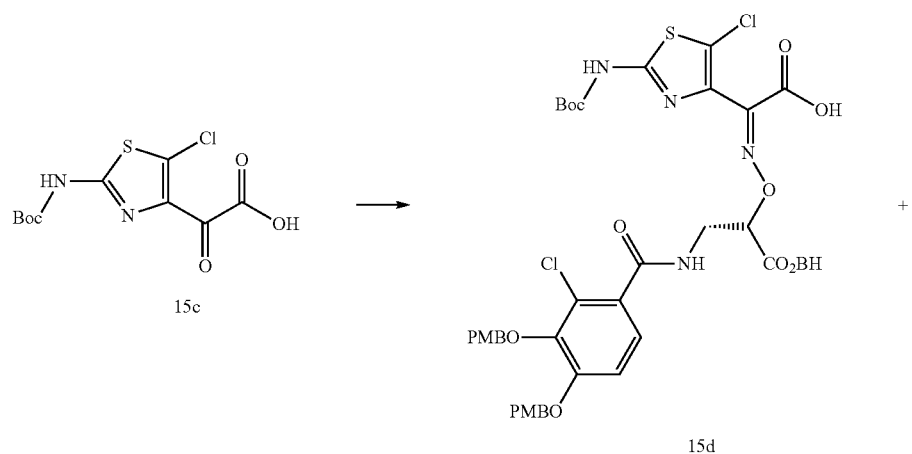
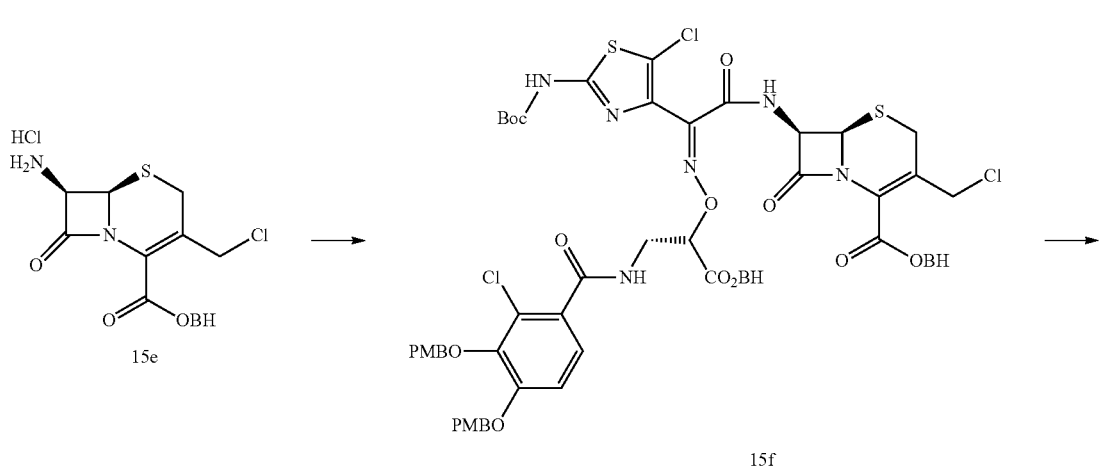

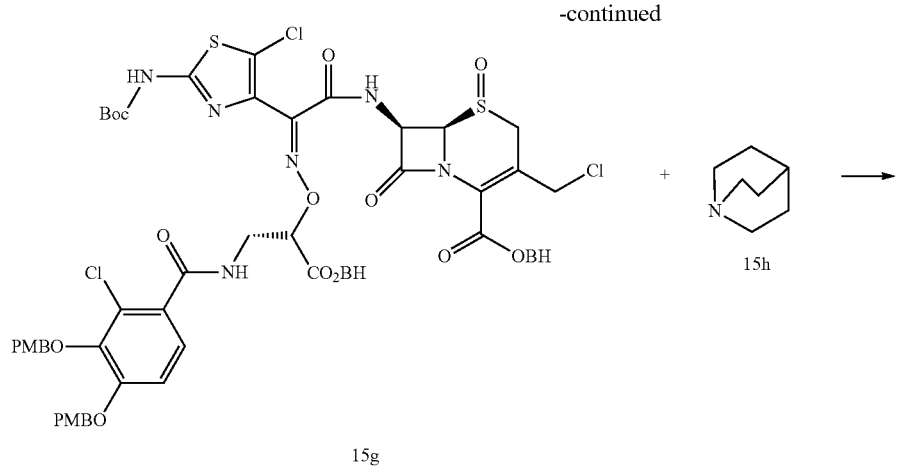

15g

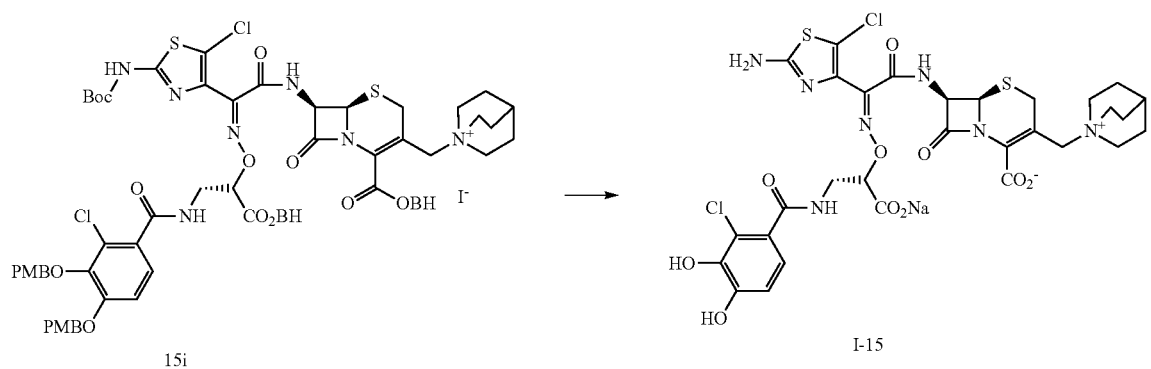

15i                             I-15

Step 1: Compound 15a→Compound 15b+Compound 15c→Compound 15d

Using compound 15a (30.0 g, 36.3 mmol), the desired compound was synthesized as described in step 5 of Example 6 to obtain compound 15d (38.41 g). Compound 15d was used in the next reaction without purification.

Step 2: Compound 15d+Compound 15e→Compound 15f

Using an the total amount (corresponding to 36.3 mmol) of the resulting compound 15d, the desired compound was synthesized as described in step 6 of Example 1.

Yield 45.45 g, (91%)

$^1$H-NMR (CDCl$_3$) δ: 8.12 (1H, s), 7.81 (1H, d, J=10.07 Hz), 7.41-7.17 (26H, m), 6.93-6.77 (7H, m), 6.08 (1H, dd, J=9.99, 4.80 Hz), 5.20 (1H, dd, J=6.25, 3.66 Hz), 4.98-4.79 (5H, m), 4.45 (1H, d, J=3.36 Hz), 4.18-4.00 (2H, m), 3.81-3.76 (7H, m), 3.52 (1H, d, J=18.45 Hz), 3.16 (1H, d, J=18.45 Hz), 1.51 (9H, s).

Step 3: Compound 15f→Compound 15g

Using compound 15f (45.5 g, 32.9 mmol), the desired compound was synthesized as described in step 7 of Example 1.

Yield 35.0 g, (76%)

$^1$H-NMR (CDCl$_3$) δ: 8.12 (1H, s), 7.81 (1H, d, J=10.07 Hz), 7.41-7.17 (26H, m), 6.93-6.77 (7H, m), 6.08 (1H, dd, J=9.99, 4.80 Hz), 5.20 (1H, dd, J=6.25, 3.66 Hz), 4.98-4.79 (5H, m), 4.45 (1H, d, J=3.36 Hz), 4.18-4.00 (2H, m), 3.81-3.76 (7H, m), 3.52 (1H, d, J=18.45 Hz), 3.16 (1H, d, J=18.45 Hz), 1.51 (9H, s).

Step 4: Compound 15g+Compound 15h→Compound I-15

Using compound 15g (1.40 g, 1.00 mmol) and compound 15h (111 mg, 1.00 mmol), the desired compound was synthesized as described in step 8 of Example 1.

Yield 424.3 mg, (43%)

$^1$H-NMR (D$_2$O) δ: 6.99 (1H, d, J=8.31 Hz), 6.88 (1H, d, J=8.31 Hz), 5.81 (1H, d, J=4.95 Hz), 5.24 (1H, d, J=4.95 Hz), 4.92-4.88 (1H, m), 4.49 (1H, d, J=14.10 Hz), 3.93 (1H, dd, J=14.48, 3.02 Hz), 3.80 (1H, dd, J=14.48, 8.81 Hz), 3.66 (1H, d, J=17.12 Hz), 3.59 (1H, d, J=13.93 Hz), 3.45-3.26 (6H, m), 2.94 (1H, d, J=16.79 Hz), 2.19-2.16 (1H, m), 2.01-1.94 (6H, m).

Elemental analysis: C30H30Cl2N7O10S2Na(H2O)7.9

Cal'd: C, 37.97; H, 4.86; Cl, 7.47; N, 10.33; S, 6.76; Na, 2.42(%).

Found: C, 37.94; H, 4.79; Cl, 7.42; N, 10.36; S, 6.81; Na, 2.45(%).

Example 16
Synthesis of Compound I-16
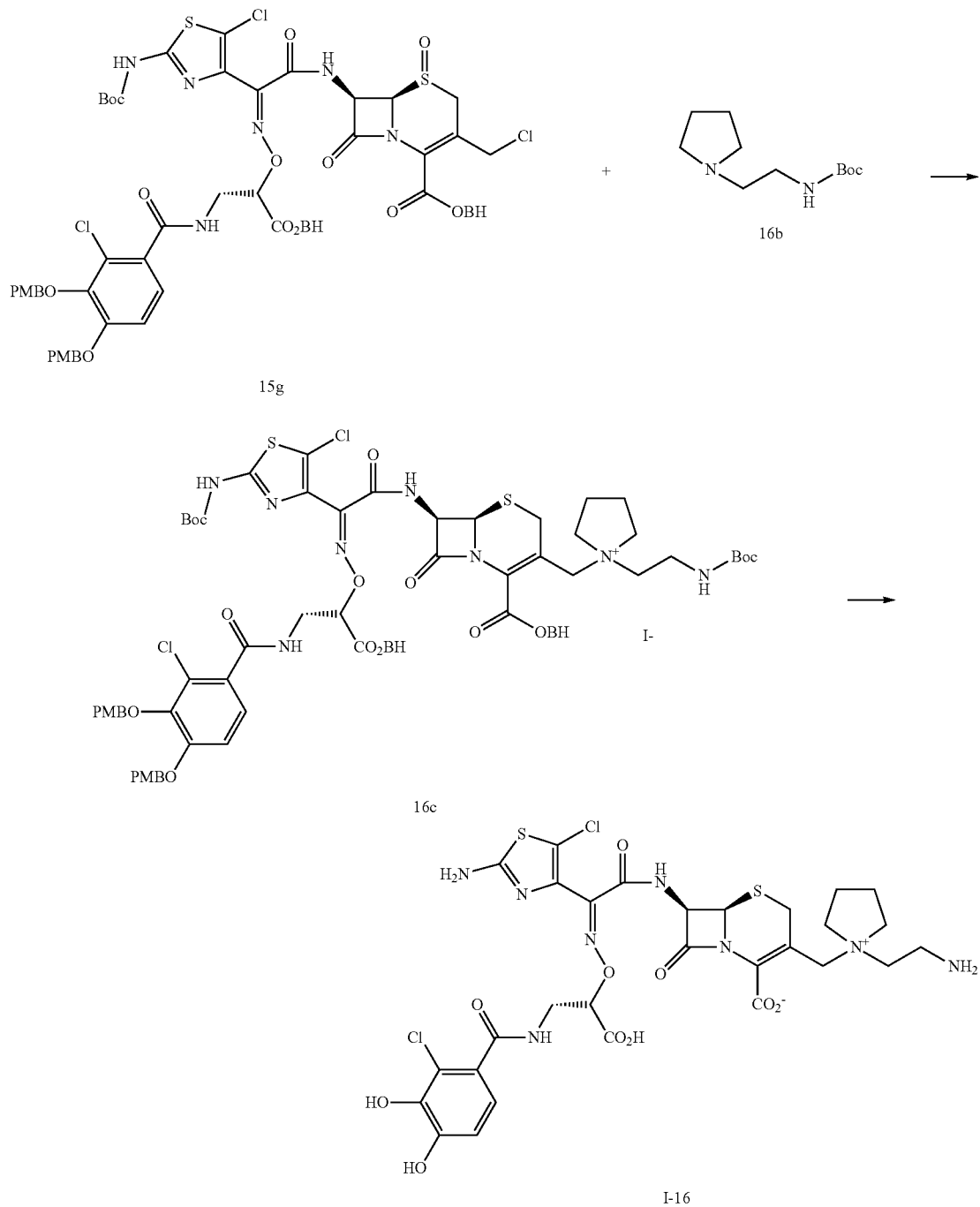
[Formula 46]
Step: Compound 15g+Compound 16b→Compound I-16
Using compound 15g (1.40 g, 1.00 mmol) and compound 16b (236 mg, 1.10 mmol), the desired compound was synthesized as described in step 8 of Example 1.
Yield 327.8 mg, (36%)
$^1$H-NMR (D$_2$O) δ: 6.99 (1H, d, J=8.39 Hz), 6.88 (1H, d, J=8.39 Hz), 5.80 (1H, d, J=4.95 Hz), 5.26 (1H, d, J=4.95 Hz), 4.93-4.88 (1H, m), 3.95-3.80 (3H, m), 3.72 (1H, d, J=16.79 Hz), 3.62-3.41 (8H, m), 3.12 (1H, d, J=16.79 Hz), 2.22 (4H, br s).
Elemental analysis: C29H32Cl2N8O10S2(H2O)6.5
Cal'd: C, 38.50; H, 5.01; Cl, 7.84; N, 12.39; S, 7.09(%).
Found: C, 38.42; H, 4.88; Cl, 7.90; N, 12.34; S, 7.12(%).

Example 17
Synthesis of Compound I-17
[Formula 47]
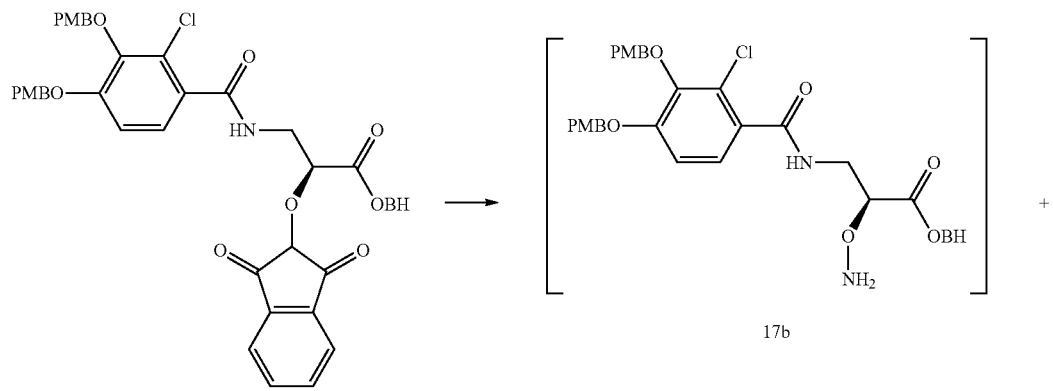
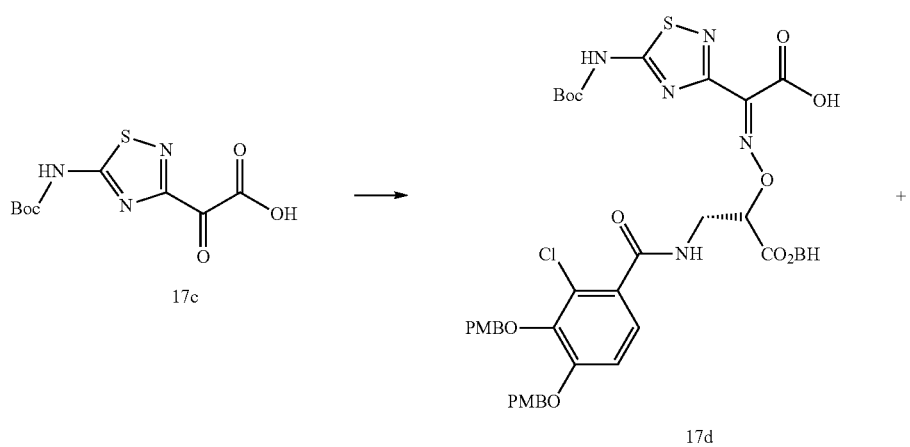
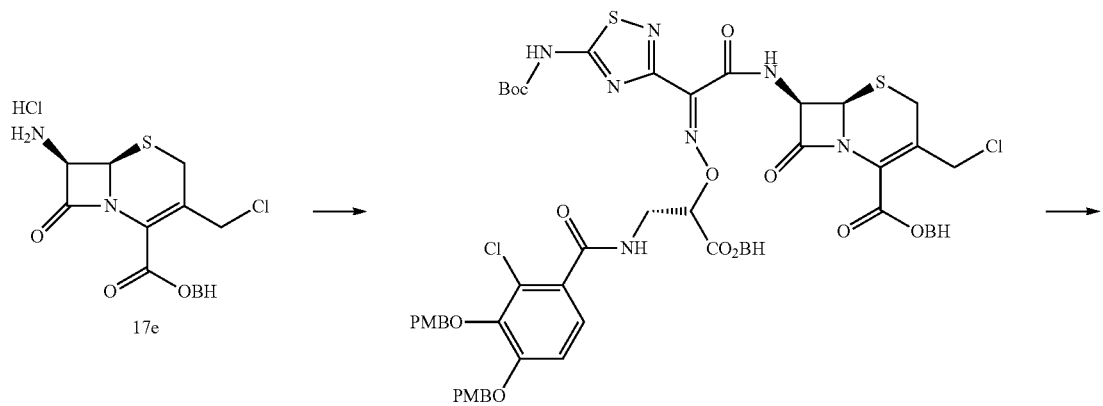

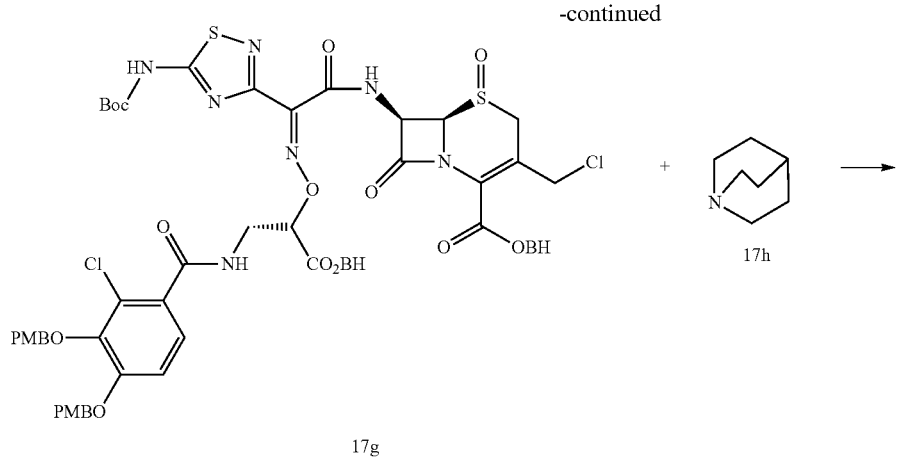

17g

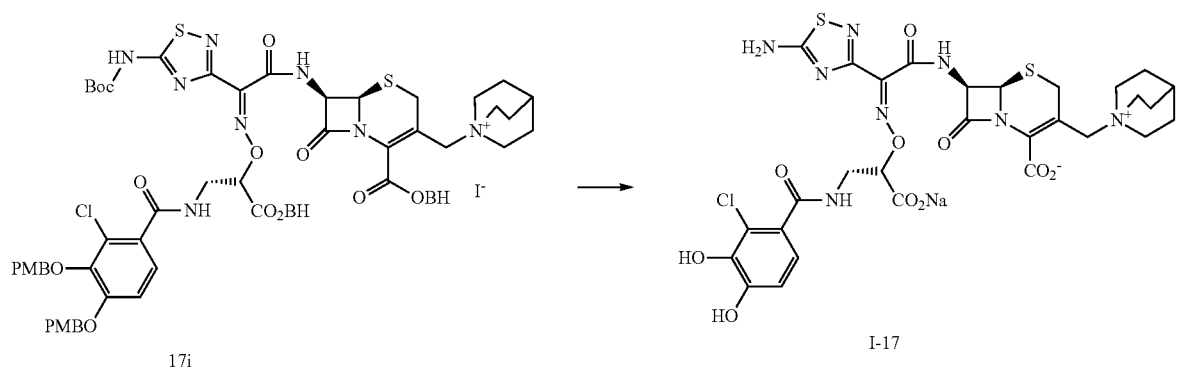

17i                          I-17

Step 1: Compound 17a→Compound 17b+Compound 17c→Compound 17d

Using compound 17a (11.2 g, 13.5 mmol), the desired compound was synthesized as described in step 5 of Example 6 to obtain compound 17d (14.5 g). Compound 17d was used in the next reaction without purification.

Step 2: Compound 17d+Compound 17e→Compound 17f

Using the total amount (corresponding to 13.5 mmol) of the resulting compound 17d, the desired compound was synthesized as described in step 6 of Example 1 to obtain compound 17f (13.26 g, 66%) as a crude product. Compound 17f was used in the next reaction without further purification.

Step 3: Compound 17f→Compound 17g

Using compound 17f (13.3 g, 9.8 mmol), the desired compound was synthesized as described in step 7 of Example 1.

Yield 5.76 g, (43%)

$^1$H-NMR (CDCl$_3$) δ: 8.65 (1H, br s), 7.69 (1H, d, J=9.46 Hz), 7.39-7.12 (26H, m), 6.92-6.75 (7H, m), 6.13 (1H, dd, J=9.46, 4.73 Hz), 5.33 (1H, dd, J=6.25, 3.36 Hz), 4.96-4.81 (5H, m), 4.47 (1H, d, J=3.66 Hz), 4.14-4.05 (2H, m), 3.81-3.77 (7H, m), 3.51 (1H, d, J=18.53 Hz), 3.17 (1H, d, J=18.53 Hz), 1.54 (9H, s).

Step 4: Compound 17g+Compound 17h→Compound I-17

Using compound 17g (1.37 g, 1.00 mmol) and compound 17h (111 mg, 1.00 mmol), the desired compound was synthesized as described in step 8 of Example 1.

Yield 568.1 mg, (60%)

$^1$H-NMR (D$_2$O) δ: 6.98 (1H, d, J=8.31 Hz), 6.87 (1H, d, J=8.31 Hz), 5.83 (1H, d, J=4.87 Hz), 5.25 (1H, d, J=4.87 Hz), 5.00-4.96 (1H, m), 4.49 (1H, d, J=14.44 Hz), 3.95 (1H, dd, J=14.60, 3.11 Hz), 3.83 (1H, dd, J=14.60, 8.48 Hz), 3.66 (1H, d, J=16.62 Hz), 3.56 (1H, d, J=13.76 Hz), 3.44-3.26 (6H, m), 2.91 (1H, d, J=16.95 Hz), 2.20-2.15 (1H, m), 2.00-1.95 (6H, m).

Elemental analysis: C29H30ClN8O10S2Na(H2O)8 (NaHCO3)0.09

Cal'd: C, 37.78; H, 5.02; Cl, 3.83; N, 12.12; S, 6.93; Na, 2.71(%).

Found: C, 37.80; H, 4.96; Cl, 3.93; N, 12.18; S, 6.81; Na, 2.72(%).

Example 18
Synthesis of Compound I-18
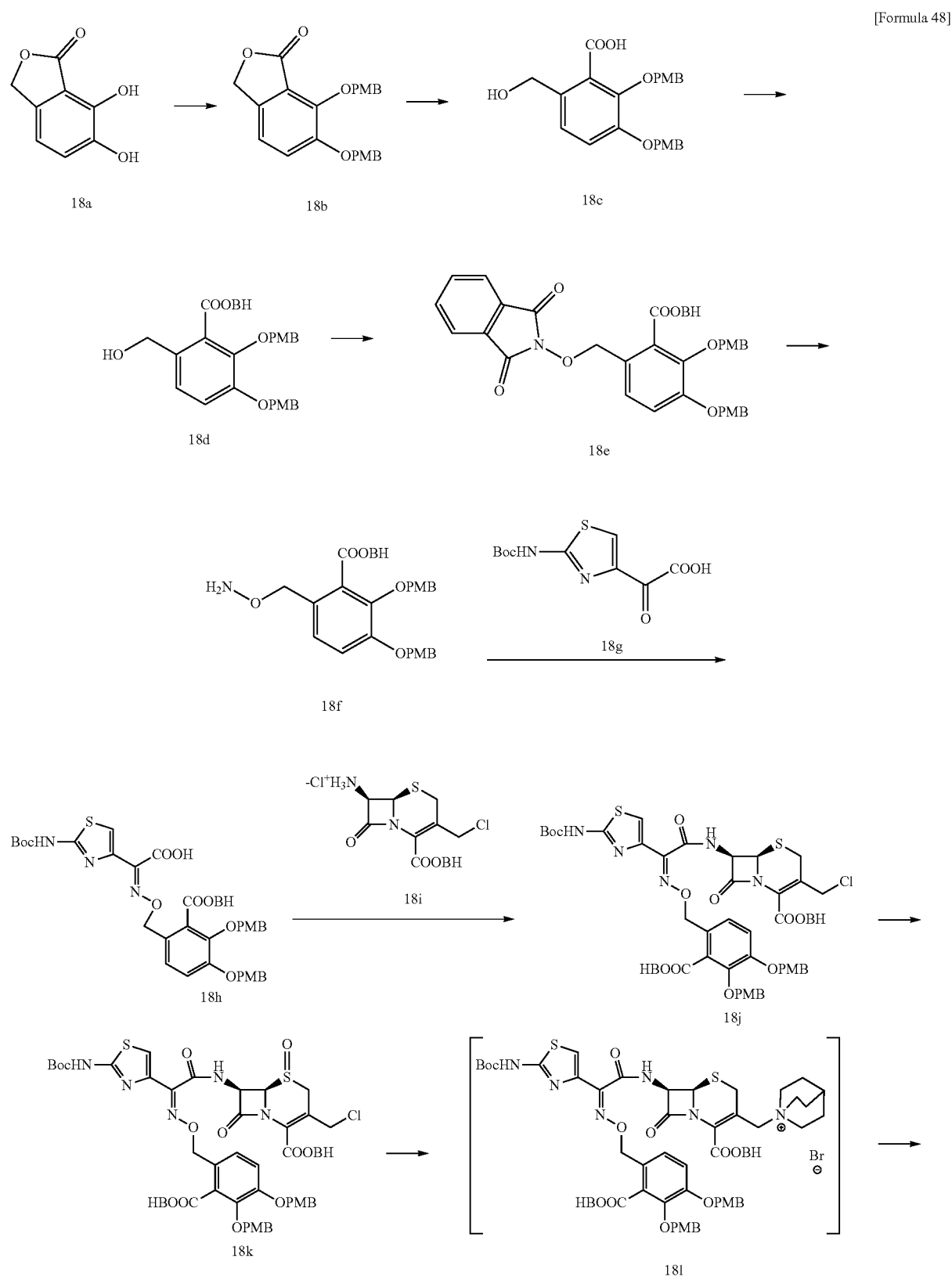

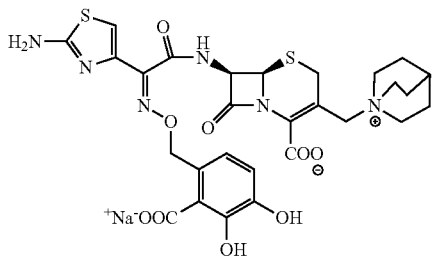

I-18

Step 1: Synthesis of Compound 18b

To a DMF (120 mL) solution of compound 18a (12.6 g, 76 mmol) were added potassium carbonate (23.0 g. 166 mmol), paramethoxybenzyl chloride (22.7 mL, 166 mmol) and sodium iodide (5.67 g, 38 mmol), and the mixture was stirred at 70° C. for 1.5 hours. The solvent was distilled off under reduced pressure, water was added to the resulting residue, and this was extracted with ethyl acetate. The organic layer was washed sequentially with water and brine, and dried over anhydrous magnesium sulfate. The inorganic substances were removed by filtration, and the filtrate was concentrated under reduced pressure. To the residue was added diisopropyl ether, and the generated solid was filtered to obtain compound 18b (22.7 g, yield 74%) as a yellow solid.

$^1$H-NMR (CDCl$_3$) δ: 3.79 (3H, s), 3.82 (3H, s), 5.05 (2H, s), 5.17 (2H, s), 5.26 (2H, s), 6.82 (2H, d, J=8.5 Hz), 6.89 (2H, d, J=8.5 Hz), 7.00 (1H, d, J=8.2 Hz), 7.22 (1H, d, J=8.2 Hz), 7.30 (2H, d, J=8.2 Hz), 7.42 (2H, d, J=8.4 Hz).

Step 2: Synthesis of Compound 18c

Compound 18b (22.4 g, 55 mmol) was dissolved in methanol (55 mL) and tetrahydrofuran (55 mL), a 2 mmol/L aqueous sodium hydroxide solution (83 mL, 165 mmol) was added, and the mixture was stirred at 70° C. for 1.5 hours. After the reaction mixture was cooled to room temperature, diethyl ether was added, and the aqueous layer was separated. The aqueous layer was adjusted to pH=3.0 with 2 mol/L hydrochloric acid, and extracted with dichloromethane. The organic layer was sequentially washed with water, and brine, and dried over anhydrous sodium sulfate. The inorganic substances were removed by filtration, and the filtrate was concentrated under reduced pressure, and dried under reduced pressure to obtain compound 18c (20.5 g, yield 88%) as a pink solid.

$^1$H-NMR (CDCl$_3$) δ: 3.80 (3H, s), 3.84 (3H, s), 4.67 (2H, s), 5.11 (2H, s), 5.12 (2H, s), 6.82 (2H, d, J=8.7 Hz), 6.95 (2H, d, J=8.7 Hz), 7.19-7.24 (4H, m), 7.39 (2H, d, J=8.7 Hz).

Step 3: Synthesis of Compound 18d

To a tetrahydrofuran (50 mL) solution of compound 18c (10.2 g, 24 mmol) was added dropwise a tetrahydrofuran (50 mL) solution of diphenyldiazomethane (5.6 g, 28.8 mmol) over 1 hour, and the mixture was stirred at room temperature overnight. The solvent was distilled off under reduced pressure, and dried under reduced pressure to obtain compound 18d as a red oil.

$^1$H-NMR (CDCl$_3$) δ: 3.77 (3H, s), 3.82 (3H, s), 4.37 (2H, s), 4.90 (2H, s), 5.06 (2H, s), 6.65 (2H, d, J=8.2 Hz), 6.90 (2H, d, J=8.4 Hz), 6.94 (2H, d, J=8.4 Hz), 7.02 (1H, d, J=8.2 Hz), 7.07 (1H, d, J=8.2 Hz), 7.10 (1H, s), 7.26-7.40 (13H, m).

Step 4: Synthesis of Compound 18e

To a tetrahydrofuran (60 mL) solution of compound 18d (5.91 g, 10 mmol) were added N-hydroxyphthalimide (1.96 g, 12 mmol) and triphenylphosphine (3.15 g, 12 mmol). After ice-cooling, DIAD (2.33 mL, 12 mmol) was added over 5 minutes, and the mixture was stirred at room temperature for 4.5 hours. The solvent was distilled off under reduced pressure, methanol was added to the resulting residue, and the generated solid was filtered to obtain compound 18e (5.88 g, yield 80%) as a brown solid.

$^1$H-NMR (CDCl$_3$) δ: 3.76 (3H, s), 3.82 (3H, s), 4.85 (2H, s), 5.04 (2H, s), 5.06 (2H, s), 6.64 (2H, d, J=8.4 Hz), 6.90 (2H, d, J=8.4 Hz), 6.94 (2H, d, J=8.5 Hz), 7.06 (1H, d, J=8.4 Hz), 7.14-7.24 (7H, m), 7.33-7.40 (7H, m), 7.69-7.79 (4H, m).

Step 5: Synthesis of Compound 18j

After a dichloromethane (60 mL) solution of compound 18e (6.25 g, 8.5 mmol) was ice-cooled, methylhydrazine (475 µL, 8.9 mmol) was added at once, and the mixture was stirred at room temperature for 30 minutes. After insolubles were removed by filtration, the solvent was distilled off under reduced pressure, and dried under reduced pressure to obtain compound 18f as an orange oil. The resulting compound 18f was used in the next reaction. The total amount of the resulting compound 18f was dissolved in methanol (25 ml), compound 18g (2.55 g, 9.35 mmol) was added, and the mixture was stirred at room temperature for 1.5 hours. The solvent was distilled off under reduced pressure, water was added to the resulting residue, and this was extracted with ethyl acetate. The organic layer was sequentially washed with water and brine, and dried over anhydrous magnesium sulfate. The inorganic substances were removed by filtration, and the filtrate was concentrated under reduced pressure, and dried under reduced pressure to obtain compound 18h as an orange foam. The resulting compound 18h was used in the next reaction.

The total amount of the resulting compound 18h was dissolved in ethyl acetate (25 ml), the solution was cooled to −40° C., thereafter, compound 18i (4.22 g, 9.35 mmol), and phenyl dichlorophosphate (1.91 mL, 12.8 mmol) were added, N-methylmorpholine (3.74 mL, 34 mmol) was added dropwise over 5 minutes, and the mixture was stirred at −40° C. for 1 hour. To the resulting reaction mixture was added 0.2 mol/L hydrochloric acid, and this was extracted with ethyl acetate. The organic layer was sequentially washed with water, a 5% aqueous sodium bicarbonate solution, and brine, and dried over anhydrous magnesium sulfate. The inorganic substances were removed by filtration, and the filtrate was concentrated under reduced pressure. The resulting crude product was purified by silica gel column chromatography (hexane-ethyl acetate) to obtain compound 18j (7.81 g, yield 73%) as a yellow foam. $^1$H-NMR (CDCl$_3$) δ: 1.59 (10H, s), 3.12 (1H, d, J=17.9 Hz), 3.39 (1H, d, J=17.9 Hz), 3.75 (3H, s), 3.82 (3H, s), 3.97 (1H, d, J=12.0 Hz), 4.45 (1H, d, J=12.0 Hz), 4.79 (2H, d, J=2.4 Hz), 4.91 (1H, d, J=5.0 Hz), 5.03 (2H, s), 5.12 (2H, s), 5.87 (1H, dd, J=8.8, 5.0 Hz), 6.60 (2H, d, J=8.5 Hz), 6.87-6.91 (5H, m), 6.99-7.39 (31H, m), 7.56 (1H, d, J=8.8 Hz), 8.09 (1H, s).

Step 6: Synthesis of Compound 18k

According to the similar manner as described in step 7 of Example 1, compound 18k (6.91 g, yield 87%) was obtained as a white solid, from compound 18j (7.81 g, 6.2 mmol).

$^1$H-NMR (CDCl$_3$) δ: 1.62 (9H, s), 2.90 (1H, d, J=18.9 Hz), 3.35 (1H, d, J=18.9 Hz), 3.75 (3H, s), 3.81 (3H, s), 4.08 (1H, d, J=12.7 Hz), 4.32 (1H, d, J=3.8 Hz), 4.79-4.93 (3H, m), 5.06-5.22 (4H, m), 6.19 (1H, dd, J=10.1, 5.0 Hz), 6.66 (2H, d, J=8.7 Hz), 6.89-7.45 (34H, m), 8.25 (1H, s).

Step 7: Synthesis of Compound I-18

After a DMA (1.5 mL) solution of quinuclidine (89 mg, 0.80 mmol) was cooled to 15° C., compound 18k (1.02 g, 0.80 mmol) was added, and the mixture was degassed under reduced pressure. Sodium bromide (165 mg, 1.6 mmol) was added, and, the mixture was stirred at 15° C. for 3 hours. After DMF (3.0 mL) was added, the mixture was cooled to −40° C., phosphorus tribromide (151 µL, 1.6 mmol) was added, and the mixture was stirred at −40° C. for 30 minutes. The reaction mixture was slowly added to an ice-cooled 5% aqueous sodium chloride solution. The precipitated solid was filtered, washed with water, suspended in water, and lyophilized to obtain compound 18l as a brown solid. The resulting compound 18l was used in the next reaction without purification.

The total amount of the resulting compound 18l was dissolved in dichloromethane (10 ml), the solution was cooled to −40° C., thereafter, anisole (874 µL, 8.0 mmol) and a 2 mol/L-aluminum chloride/nitromethane solution (4.0 mL, 8.0 mmol) were sequentially added, and the mixture was stirred at 0° C. for 30 minutes. To the reaction solution was added diisopropyl ether, and a small amount of water, the mixture was stirred to generate the precipitate, and the supernatant was removed by decantation. To insolubles which has been left in a container were added dilute hydrochloric acid and acetonitrile, the mixture was stirred to completely dissolve the materials, diisopropyl ether was added, and the aqueous layer was separated. After the organic layer was extracted again with water, all aqueous layers were combined, the HP20-SS resin was added, and acetonitrile was distilled off under reduced pressure. The resulting mixed solution was purified by ODS column chromatography (water-acetonitrile). To the fractions containing the desired compound was added a 0.2 mol/L aqueous sodium hydroxide solution, pH was adjusted to 6.0 and, thereafter, a small amount of dry ice was added. The resulting solution was concentrated under reduced pressure, and lyophilized to obtain compound I-18 (257 mg, yield 47%) as a white powder.

$^1$H-NMR (D$_2$O) δ: 1.95 (6H, br s), 2.15 (1H, br s), 3.12 (1H, d, J=17.0 Hz), 3.30-3.39 (6H, br m), 3.69 (1H, d, J=17.0 Hz), 3.76 (1H, d, J=14.1 Hz), 4.51 (1H, d, J=14.1 Hz), 5.19 (1H, d, J=4.6 Hz), 5.48 (1H, d, J=11.8 Hz), 5.69 (1H, d, J=11.8 Hz), 5.77 (1H, d, J=4.6 Hz), 6.87 (1H, d, J=8.2 Hz), 6.94-6.97 (2H, m).

MS (m+1)=659.45

Elemental analysis: $C_{28}H_{29}N_6O_9S_2Na \cdot 5.8H_2O$

Cal'd: C, 42.83; H, 5.21; N, 10.70; S, 8.17; Na, 2.93(%).

Found: C, 42.87; H, 5.07; N, 10.71; S, 8.09; Na, 3.06(%).

Example 19

Synthesis of Compound I-19

[Formula 49]

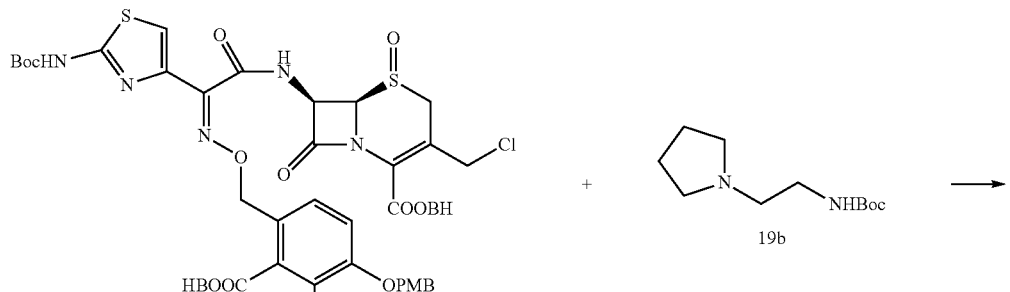

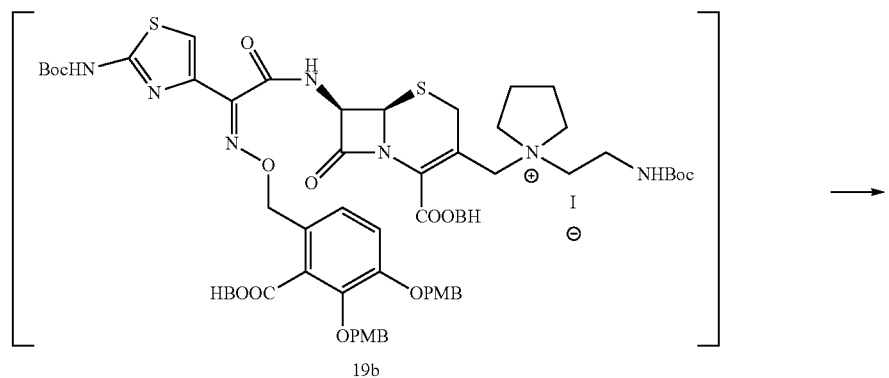

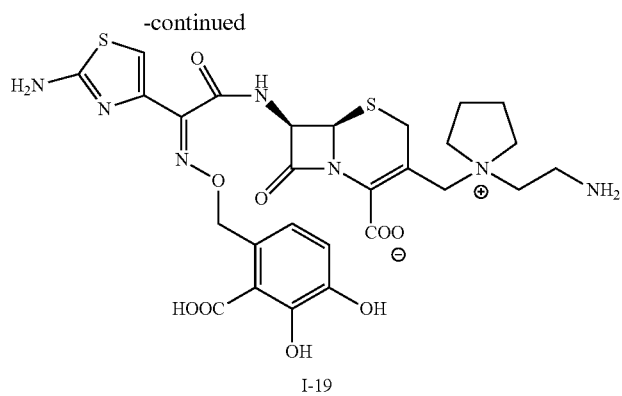

I-19

Step: Synthesis of Compound I-19

According to the similar manner as described in step 7 of Example 18, compound I-19 (135 mg, yield 26%) was obtained as a white powder, from compound 18k (1.02 g, 0.80 mmol) and compound 19a (171 mg, 0.80 mmol).

$^1$H-NMR (DMSO-$d_6$) δ: 1.99 (4H, br s), 2.86-3.86 (11H, m), 4.85 (1H, d, J=13.5 Hz), 5.11 (1H, d, J=4.8 Hz), 5.42 (2H, d, J=2.4 Hz), 5.70 (1H, dd, J=8.2, 5.1 Hz), 6.50 (1H, d, J=8.1 Hz), 6.56 (1H, d, J=8.1 Hz), 6.63 (1H, s), 7.12 (2H, s), 9.58 (1H, d, J=8.2 Hz)

MS (m+1)=662.45

Elemental analysis: $C_{27}H_{31}N_7O_9S_2 \cdot 5.8H_2O$

Cal'd: C, 42.32; H, 5.60; N, 12.80; S, 8.37(%).

Found: C, 42.36; H, 5.41; N, 12.66; S, 8.26(%).

Example 20

Synthesis of Compound I-20

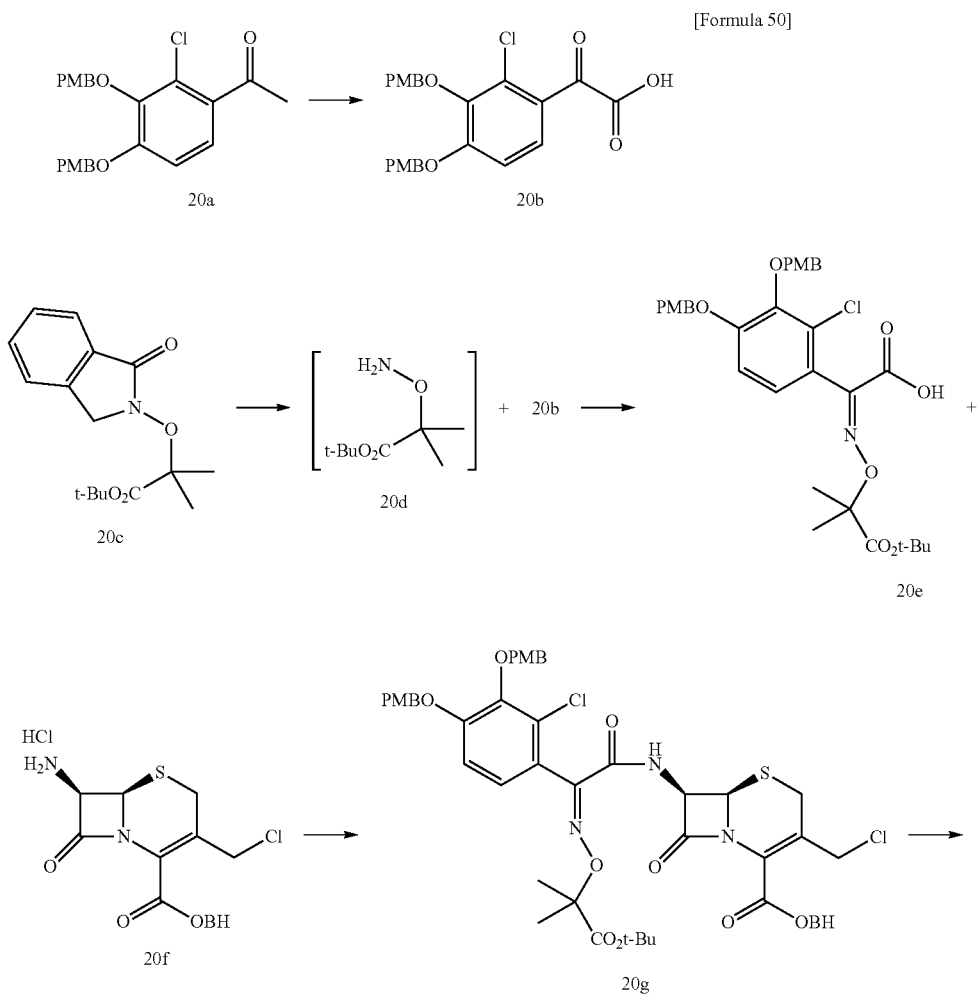

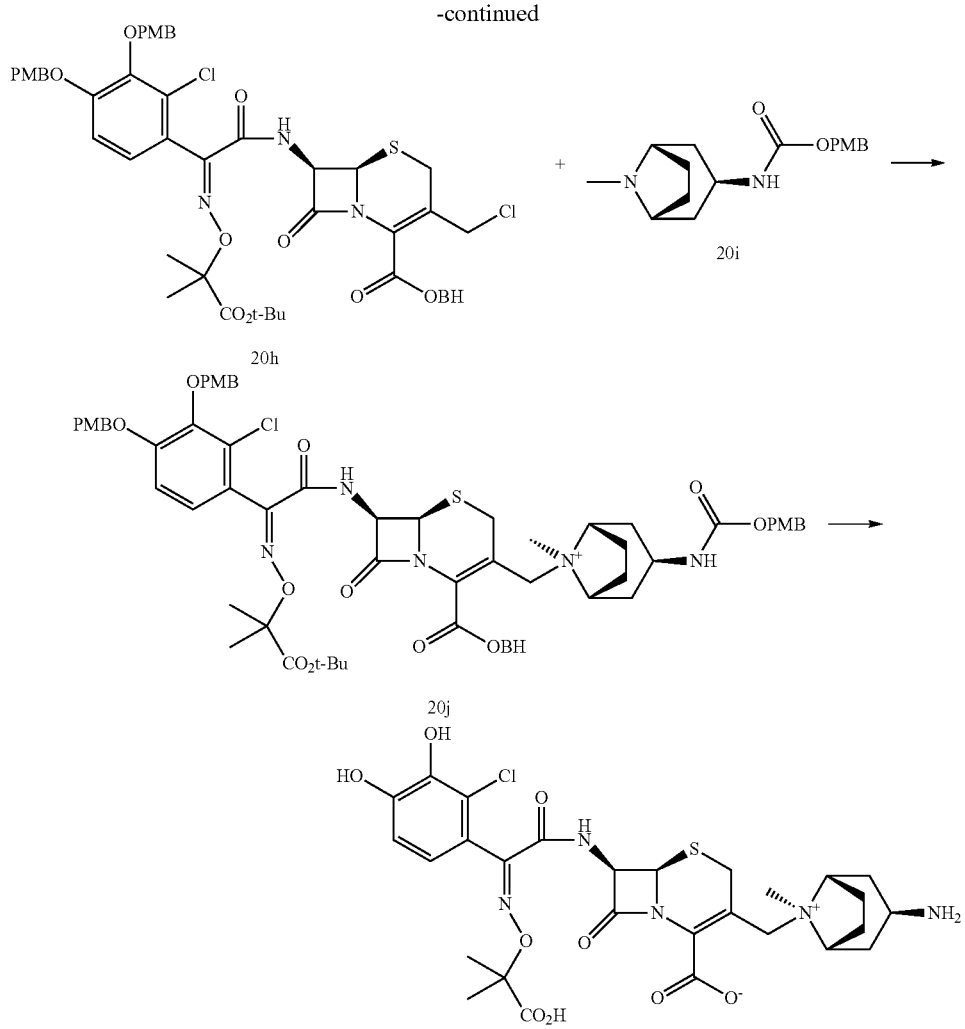

Step 1: Compound 20a→Compound 20b

To a pyridine (40 ml) solution of compound 20a (4.00 g, 9.4 mmol) was added selenium dioxide (2.60 g, 23.4 mmol), and the mixture was stirred at 80° C. overnight. The reaction solution was Celite-filtered, and concentrated under reduced pressure. The residue was diluted with ethyl acetate, and the organic layer was washed with hydrochloric acid, water and brine, and dried over magnesium sulfate. After magnesium sulfate was filtered, the filtrate was concentrated under reduced pressure and triturated with diisopropyl ether, and the precipitated solid was filtered to obtain compound 20b (3.65 g, 85%).

$^1$H-NMR (DMSO-$d_6$) δ: 7.59 (1H, d, J=8.85 Hz), 7.46 (2H, d, J=8.54 Hz), 7.36 (1H, d, J=8.85 Hz), 7.27 (2H, d, J=8.39 Hz), 6.99 (2H, d, J=8.39 Hz), 6.84 (2H, d, J=8.54 Hz), 5.23 (2H, s), 4.91 (2H, s), 3.78 (3H, s), 3.74 (3H, s).

Step 2: Compound 20c→Compound 20d+Compound 20b→Compound 20e

Using compound 20c (2.44, 8.0 mmol), the desired compound was synthesized as described in step 5 of Example 6. Compound 20e was used in the next reaction without purification.

Yield: 4.85 g, (99%)

Step 3: Compound 20e+Compound 20f→Compound 20g

Using the total amount (corresponding to 7.9 mmol) of the resulting compound 20e, the desired compound was synthesized as described in step 6 of Example 1 to obtain compound 20g (5.48 g, 69%) as a crude product. Compound 20g was used in the next reaction without further purification.

Step 4: Compound 20g→Compound 20h

Using the total amount (corresponding to 5.4 mmol) of the resulting compound 20g, the desired compound was synthesized as described in step 7 of Example 2.

Yield: 2.26 g, (41%)

$^1$H-NMR (CDCl$_3$) δ: 8.24 (1H, d, J=9.80 Hz), 7.48-7.44 (2H, m), 7.40-7.28 (12H, m), 7.11 (1H, d, J=8.54 Hz), 6.95-6.89 (4H, m), 6.85-6.81 (2H, m), 6.23 (1H, dd, J=9.80, 4.88 Hz), 5.05 (2H, s), 5.00 (1H, d, J=12.12 Hz), 4.95 (2H, s), 4.60 (1H, dd, J=4.88, 1.45 Hz), 4.17 (1H, d, J=12.12 Hz), 3.83-3.77 (7H, m), 3.42 (1H, d, J=18.15 Hz), 1.61 (3H, s), 1.60 (3H, s), 1.43 (9H, s).

Step 5: Compound 20h+Compound 20i→Compound I-20

Using compound 20h (1.03 g, 1.00 mmol) and compound 20i (335 mg, 1.10 mmol), the desired compound was synthesized as described in step 8 of Example 1.

Yield: 218.2 mg, (28%)

$^1$H-NMR (D$_2$O) δ: 7.02 (1H, d, J=8.31 Hz), 6.91 (1H, d, J=8.31 Hz), 5.87 (1H, d, J=5.19 Hz), 5.34 (1H, d, J=5.19 Hz), 4.08-3.80 (5H, m), 3.46 (1H, d, J=15.86 Hz), 3.05-2.80 (5H, m), 2.68-2.57 (2H, m), 2.29-2.09 (4H, m), 1.54 (6H, d, J=5.64 Hz).

Elemental analysis: C28H34ClN5O9S(H2O)7.3
Cal'd: C, 42.92; H, 6.25; Cl, 4.52; N, 8.94; S, 4.09(%).
Found: C, 42.92; H, 5.98; Cl, 4.66; N, 8.76; S, 4.01(%).

Example 21

Synthesis of Compound I-21

Step: Compound 20h+Compound 21b→Compound I-21

Using compound 20h (1.03 g, 1.00 mmol) and compound 21b (236 mg, 1.10 mmol), the desired compound was synthesized as described in step 8 of Example 1.

Yield 291.5 mg, (41%)

$^1$H-NMR (D$_2$O) δ: 7.00 (1H, d, J=8.39 Hz), 6.90 (1H, d, J=8.39 Hz), 5.76 (1H, d, J=5.19 Hz), 5.33 (1H, d, J=5.19 Hz), 4.10 (1H, d, J=13.57 Hz), 3.75 (1H, d, J=16.32 Hz), 3.64-3.38 (10H, m), 2.17 (4H, br s), 1.56 (3H, s), 1.54 (3H, s).

Elemental analysis: C26H32ClN5O9S(H2O)4.8
Cal'd: C, 43.83; H, 5.88; Cl, 4.98; N, 9.83; S, 4.50(%).
Found: C, 43.78; H, 5.75; Cl, 5.00; N, 9.83; S, 4.44(%).

[Formula 51]

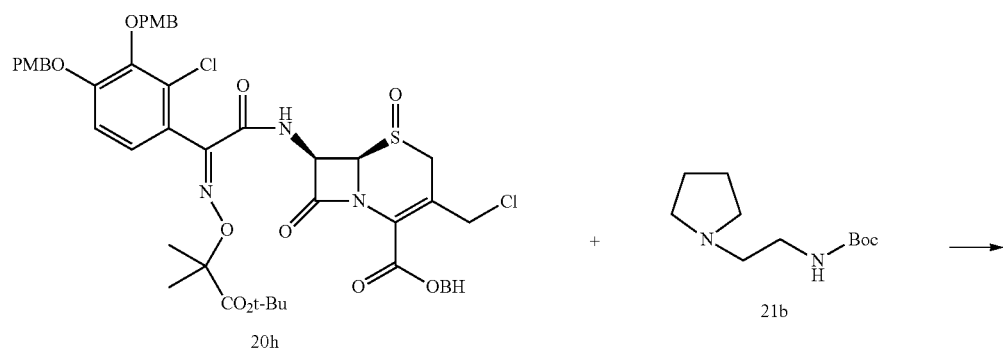

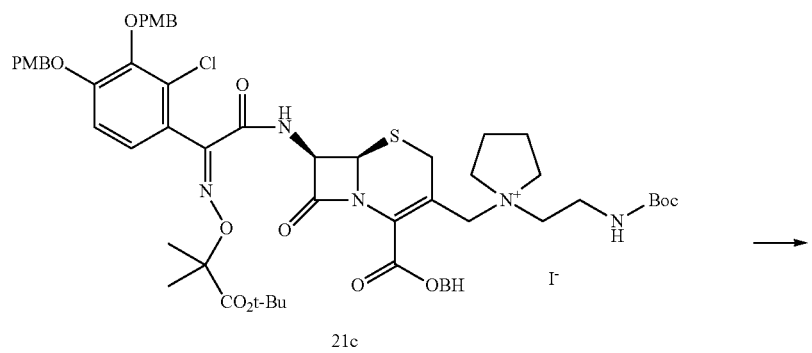

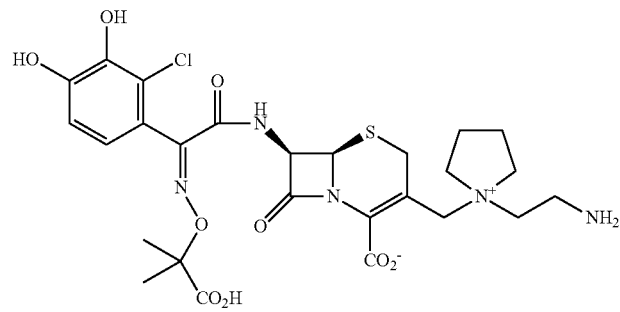

Example 22
Synthesis of Compound I-22
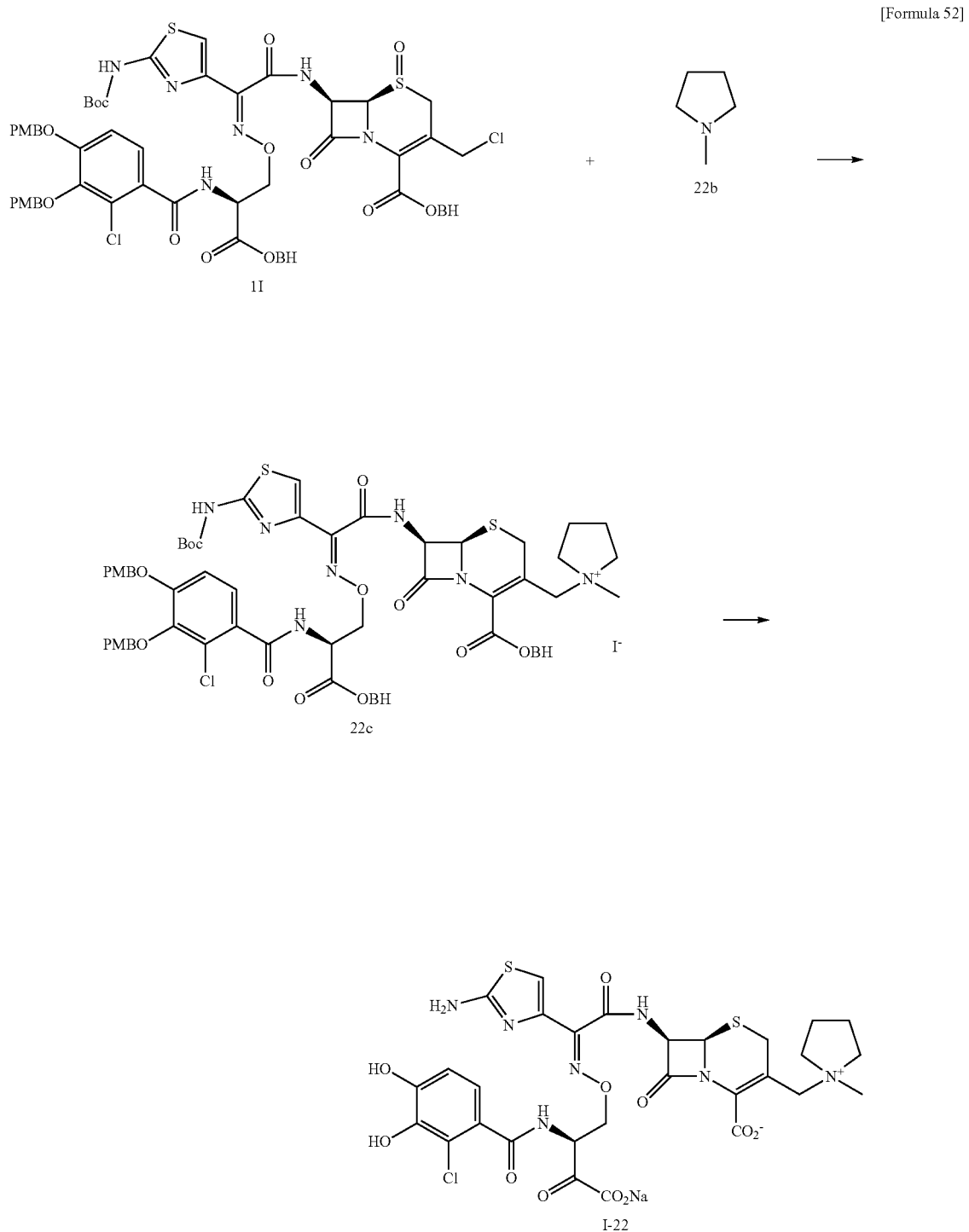
[Formula 52]
Step: Compound 1l+Compound 22b→Compound I-22
Using compound 1l (0.50 g, 0.379 mmol), the desired compound was synthesized as described in step 8 of Example 1.
Yield: 35%
MS: 724.38 (M+H)
$^1$H-NMR (D$_2$O) δ: 7.10 (1H, d, J=8.4 Hz), 7.00 (1H, s), 6.89 (1H, d, J=8.4 Hz), 5.83 (1H, d, J=4.9 Hz), 5.17 (1H, d, J=4.9 Hz), 4.67-4.66 (4H, m), 3.73 (1H, d, J=13.8 Hz), 3.55-3.44 (5H, m), 2.97 (1H, d, J=17.0 Hz), 2.92 (3H, s), 2.24-2.20 (4H, m).

Example 23
Synthesis of Compound I-23
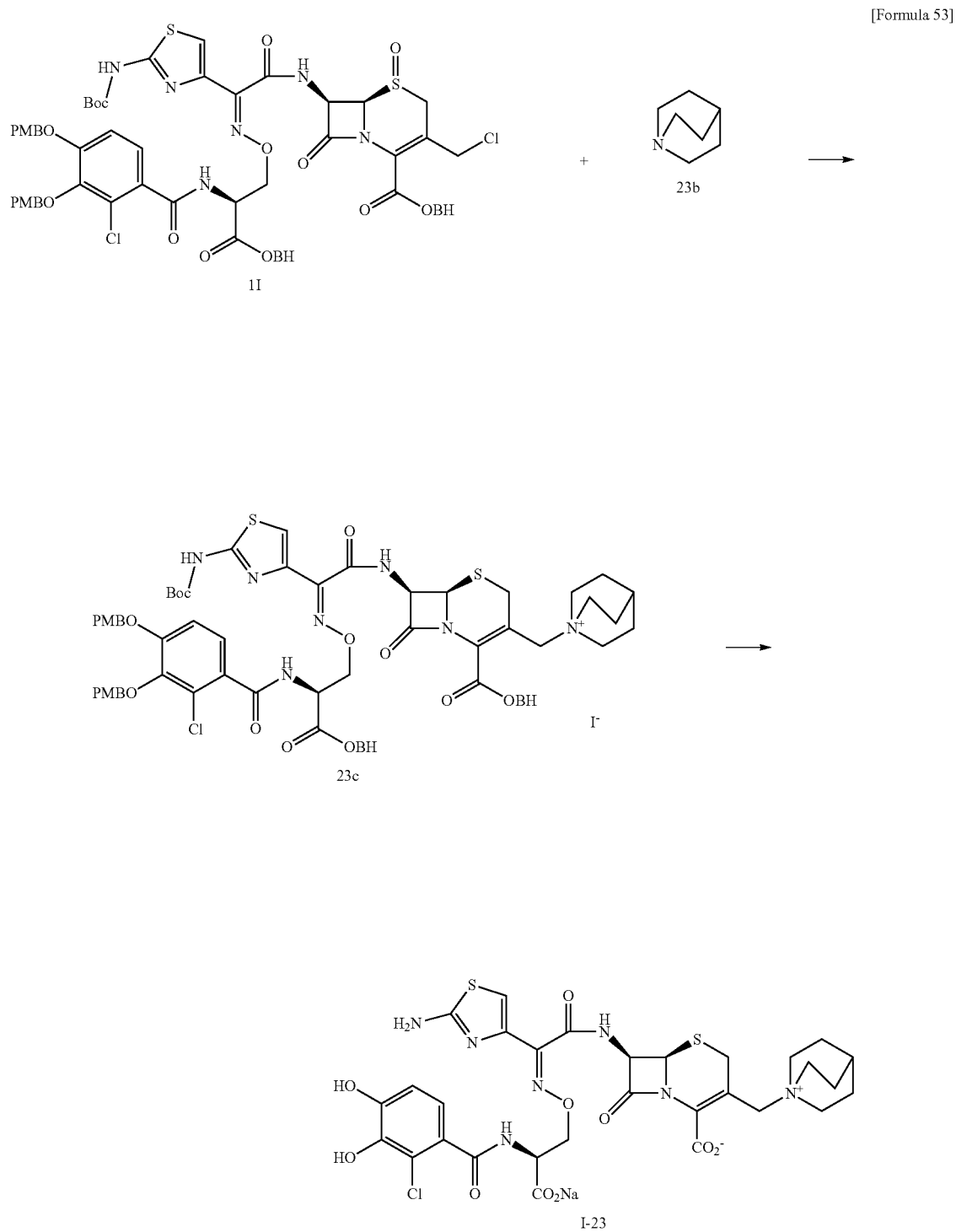
Step: Compound 11+Compound 23b→Compound I-23
Using compound 11 (0.58 g, 0.442 mmol), the desired compound was synthesized as described in step 8 of Example 1.
Yield: 53%
MS: 750.45 (M+H)
$^1$H-NMR (D$_2$O) δ: 7.09 (1H, d, J=8.3 Hz), 6.99 (1H, s), 6.89 (1H, d, J=8.3 Hz), 5.82 (1H, d, J=5.0 Hz), 5.15 (1H, d, J=5.0 Hz), 4.67-4.45 (4H, m), 3.56-3.22 (8H, m), 2.87 (1H, d, J=16.9 Hz), 2.18-2.15 (1H, m), 2.00-1.94 (6H, m).

Example 24
Synthesis of Compound I-24
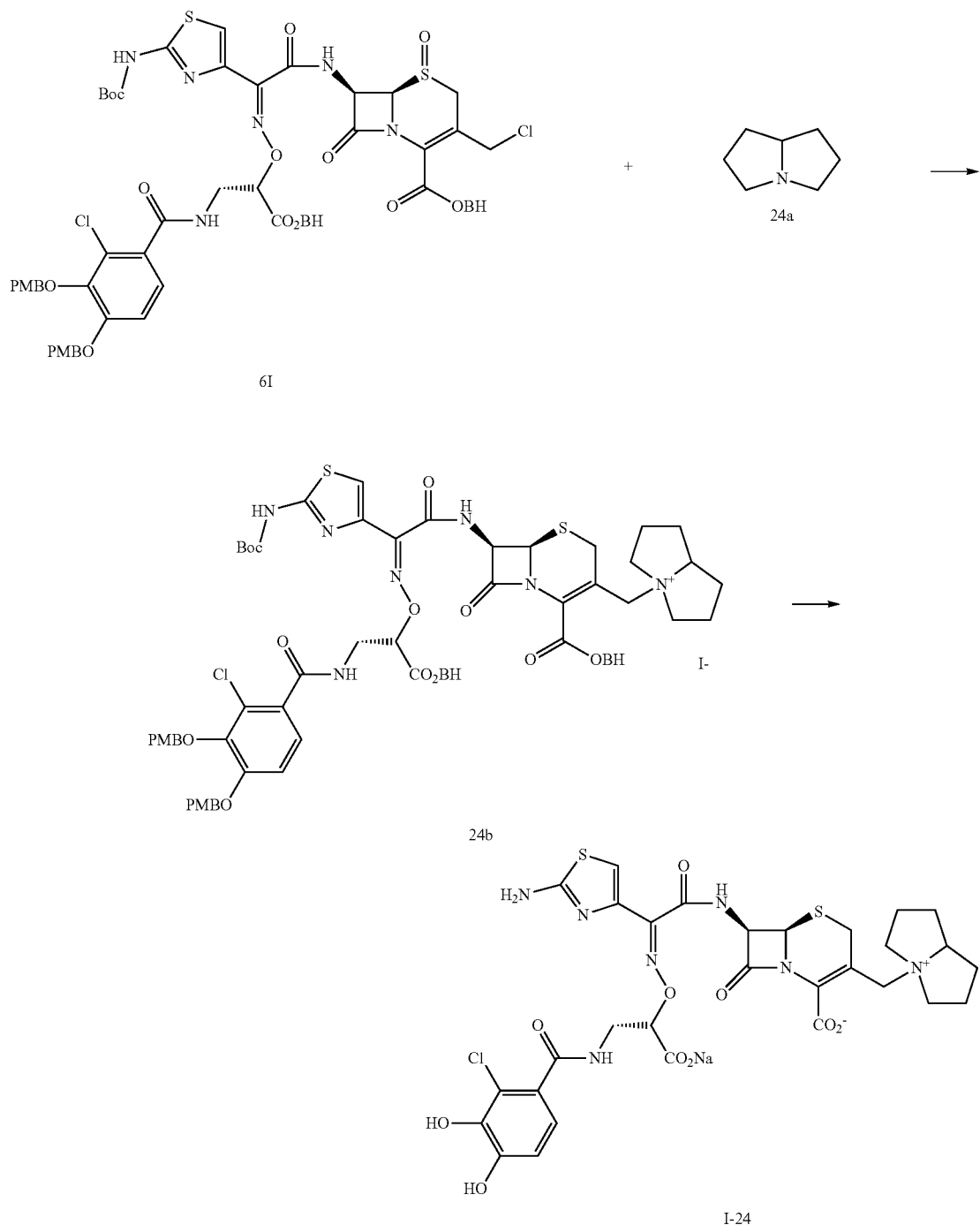
Step: Compound 6l+Compound 24a→Compound I-24
Using compound 6l (1.36 g, 1.00 mmol) and compound 24a (122 mg, 1.10 mmol), compound I-24 was synthesized as described in step 8 of Example 1.
Yield: 319.7 mg, (34%)
$^1$H-NMR (D$_2$O) δ: 7.03 (1H, s), 6.98 (1H, d, J=8.5 Hz), 6.87 (1H, d, J=8.5 Hz), 5.80 (1H, d, J=5.2 Hz), 5.23 (1H, d, J=5.2 Hz), 4.18-4.17 (1H, m), 3.93-3.42 (8H, m), 3.00 (1H, d, J=16.3 Hz), 2.19-2.11 (4H, m), 1.94-1.82 (4H, m).
Elemental analysis: C30H31ClN7O1S2Na(H2O)7 (NaHCO3)0.1
Cal'd: C, 39.87; H, 5.01; Cl, 3.91; N, 10.81; S, 7.07; Na, 2.79(%).
Found: C, 39.85; H, 4.93; Cl, 4.06; N, 10.81; S, 6.96; Na, 2.72(%).

95
Example 25
Synthesis of Compound I-25
96
Step 1: Compound 25a+Compound 25b→Compound 25c
After compound 25a (571 mg, 5.0 mmol) and compound 25b (1.67 g, 5.5 mmol) were suspended with tetrahydrofuran
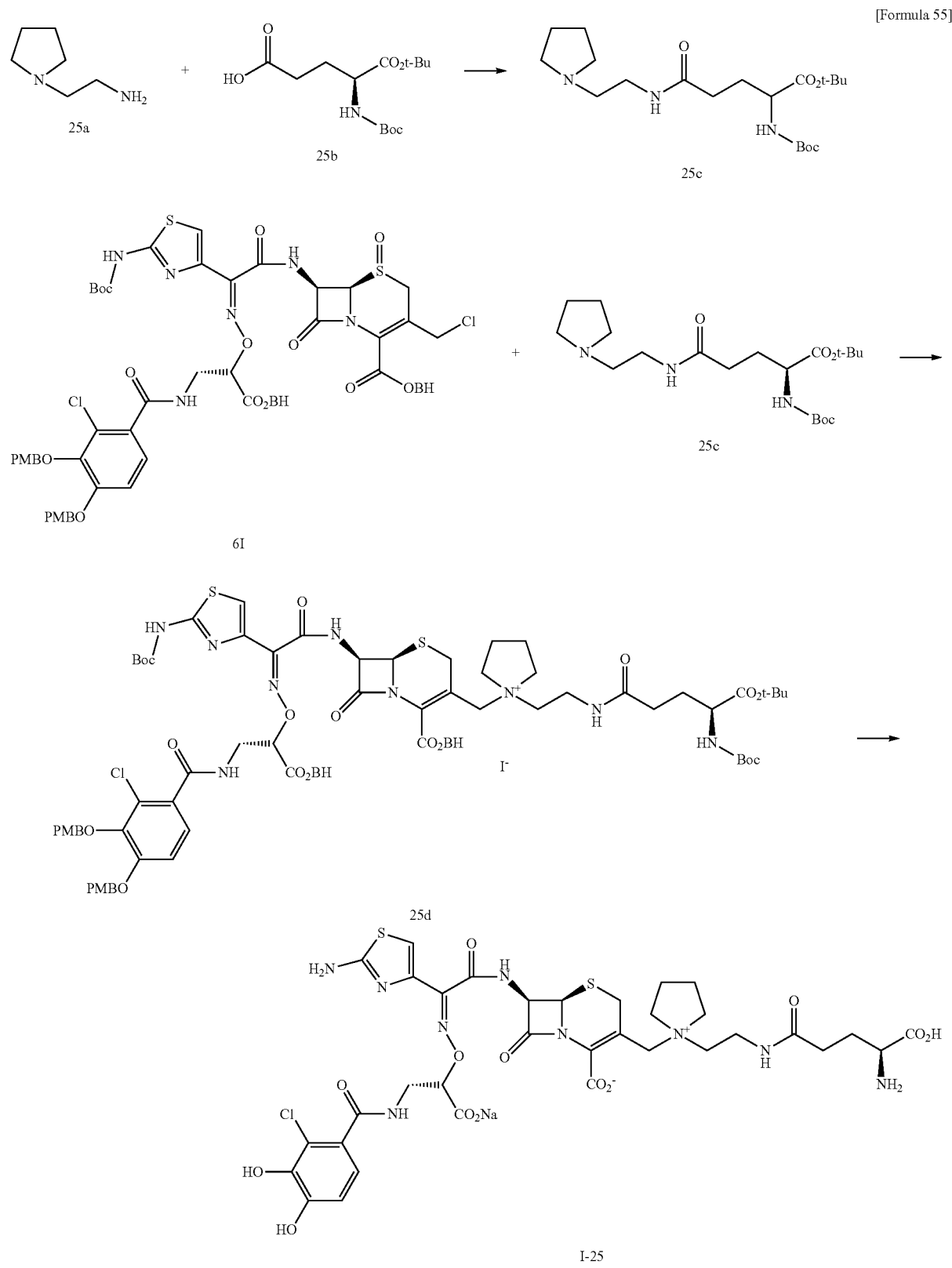

(20 ml) and added HATU (2.28 g, 6.0 mmol) under ice-cooling, the mixture was stirred overnight at room temperature. The reaction solution was diluted with ethyl acetate, and the organic layer was washed with an aqueous sodium hydroxide solution, water and brine, and dried over sodium sulfate. After sodium sulfate was filtered out, compound 25c (1.96 g, 98%) was obtained by concentrating the filtrate under reduced pressure.

$^1$H-NMR (DMSO-D$_6$) δ: 7.75 (1H, s), 7.09 (1H, d, J=7.6 Hz), 3.79-3.75 (1H, m), 3.14 (2H, q, J=6.4 Hz), 2.46-2.42 (6H, m), 2.13 (2H, t, J=7.4 Hz), 1.86-1.71 (6H, m), 1.39 (9H, s), 1.38 (9H, s).

Step 2: Compound 6l+Compound 25c→Compound I-25

Using compound 6l (1.36 g, 1.00 mmol) and compound 25c (439 mg, 1.10 mmol), compound I-25 was synthesized as described in step 8 of Example 1.

Yield: 277.1 mg, (27%)

$^1$H-NMR (D$_2$O) δ: 7.03-6.98 (2H, m), 6.88 (1H, d, J=8.4 Hz), 5.80 (1H, d, J=4.9 Hz), 5.25 (1H, d, J=4.9 Hz), 3.93-3.34 (13H, m), 3.07 (1H, d, J=16.9 Hz), 2.48-2.43 (2H, m), 2.23-2.10 (6H, m).

Elemental analysis: C34H39ClN9O13S2Na(H2O)6.9

Cal'd: C, 39.70; H, 5.17; Cl, 3.45; N, 12.26; S, 6.23; Na, 2.24(%).

Found: C, 39.60; H, 5.21; Cl, 3.77; N, 12.30; S, 6.22; Na, 2.26(%).

Example 26

Synthesis of Compound I-26

[Formula 56]

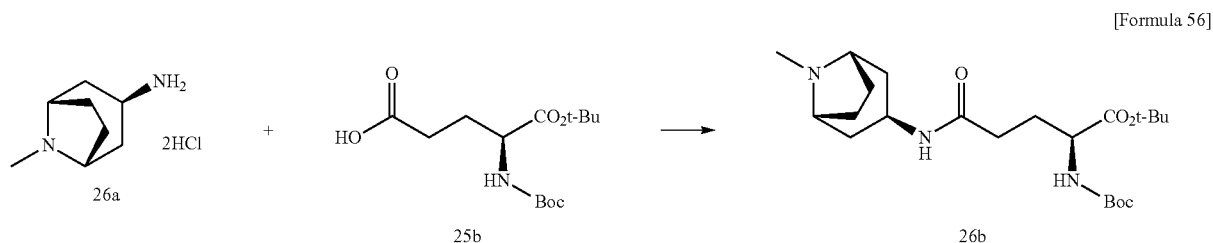

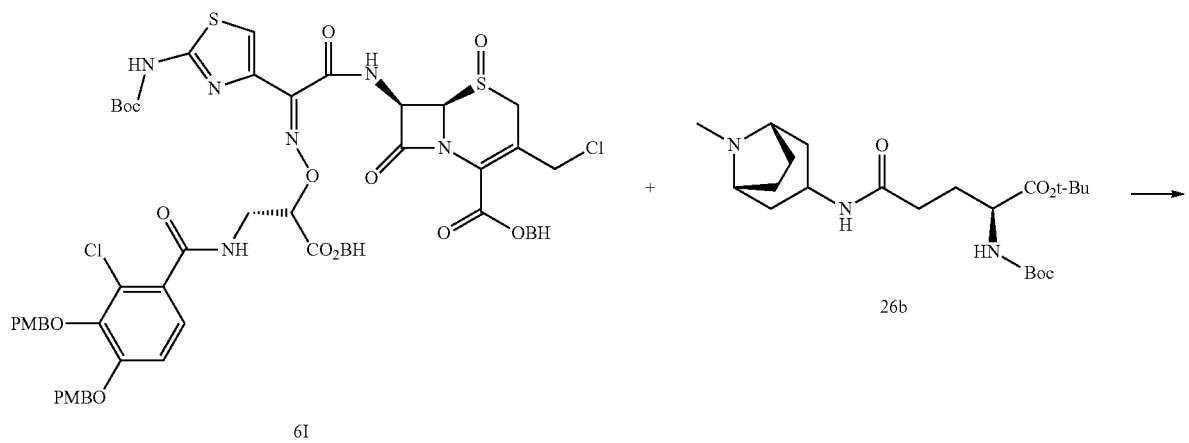

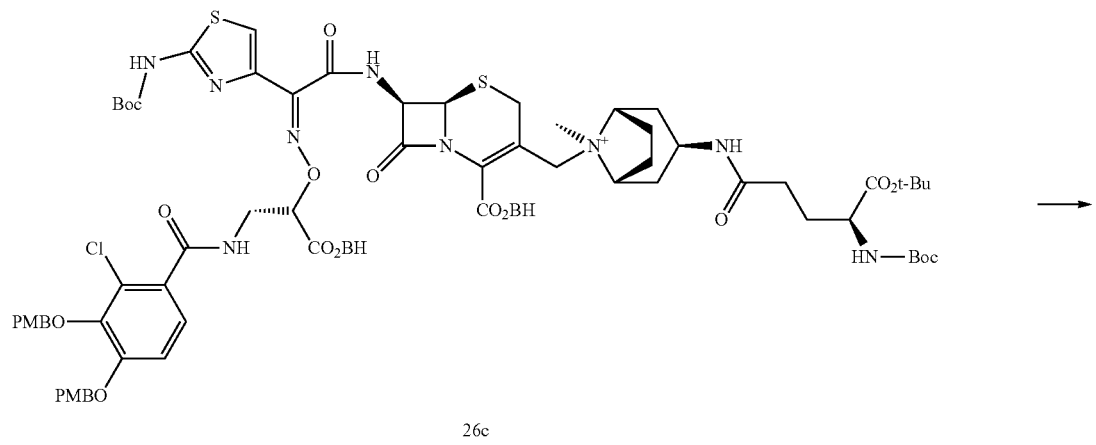

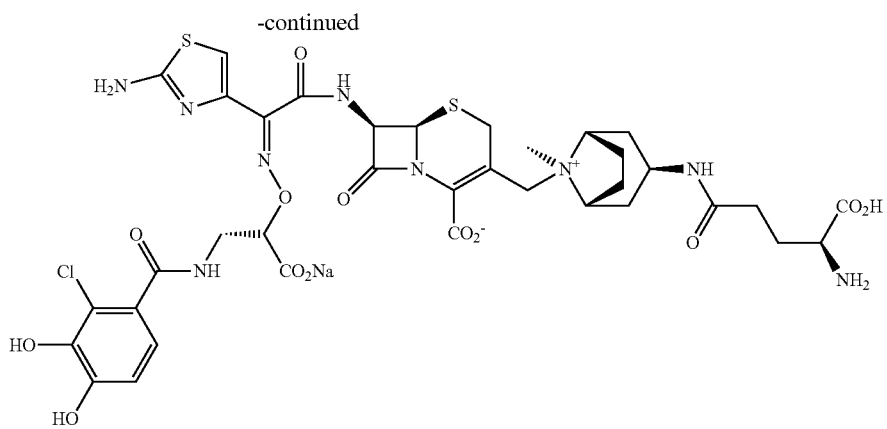

I-26

Step 1: Compound 26a+Compound 25b→Compound 26b

Using compound 26a (1.07 g, 5.0 mmol), triethylamine (1.53 ml, 11.0 mmol) and compound 25b (1.67 g, 5.5 mmol), compound 26b (2.21 g, 104%) was obtained according to the similar manner as described in Example 25.

$^1$H-NMR (DMSO-D$_6$) δ: 7.44 (1H, d, J=5.0 Hz), 7.05 (1H, d, J=7.6 Hz), 3.79-3.64 (2H, m), 2.98 (2H, br s), 2.17-2.14 (5H, m), 1.99-1.83 (8H, m), 1.54 (2H, d, J=14.0 Hz), 1.39 (9H, s), 1.38 (9H, s).

Step 2: Compound 6l+Compound 26b→Compound I-26

Using compound 6l (1.36 g, 1.00 mmol) and compound 26b (468 mg, 1.10 mmol), compound I-26 was synthesized as described in step 8 of Example 1.

Yield: 375.6 mg, (35%)

$^1$H-NMR (D$_2$O) δ: 7.02-6.99 (2H, m), 6.89 (1H, d, J=8.4 Hz), 5.79 (1H, d, J=5.0 Hz), 5.24 (1H, d, J=5.0 Hz), 4.06-3.68 (8H, m), 3.05-1.99 (16H, m).

Elemental analysis: C36H41ClN9O13S2Na(H2O)7.5

Cal'd: C, 40.58; H, 5.30; Cl, 3.33; N, 11.83; S, 6.02; Na, 2.16(%).

Found: C, 40.49; H, 5.22; Cl, 3.57; N, 11.93; S, 6.02; Na, 2.13(%).

Example 27

Synthesis of Compound I-27

[Formula 57]

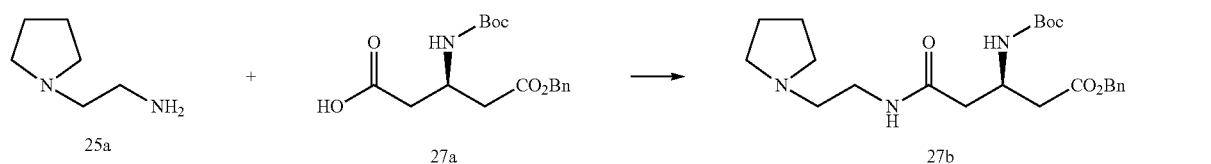

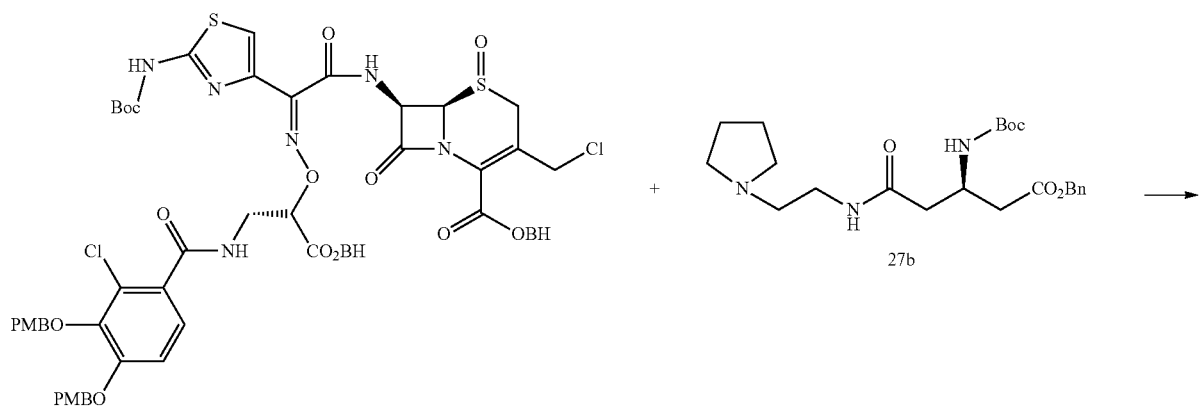

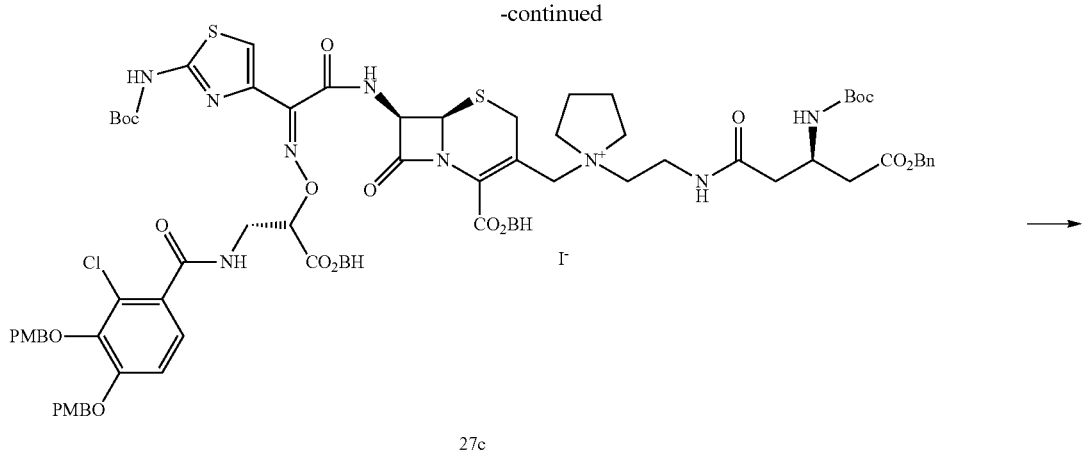

27c

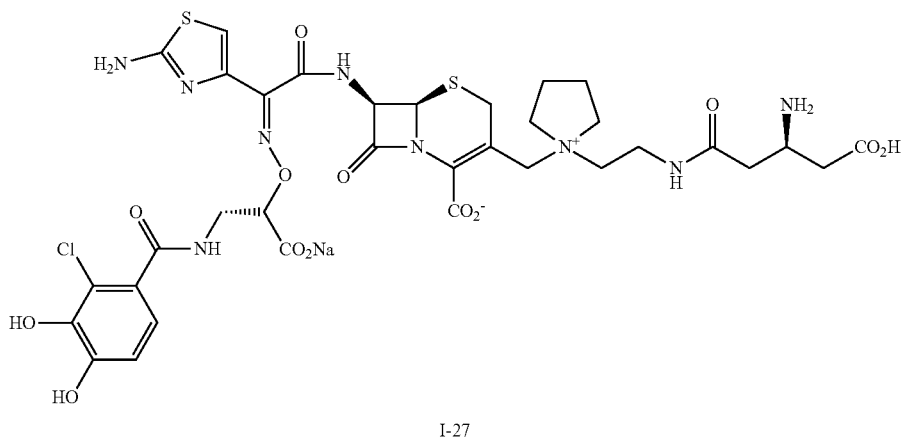

I-27

Step 1: Compound 25a+Compound 27a→Compound 27b

Using compound 25a (343 mg, 3.0 mmol) and compound 27a (1.06 g, 3.15 mmol), compound 27b (0.61 g, 47%) was obtained according to the similar manner as described in Example 25.

$^1$H-NMR (DMSO-$d_6$) δ: 7.80 (1H, t, J=5.8 Hz), 7.37-7.33 (5H, m), 6.77 (1H, d, J=8.8 Hz), 5.05 (2H, s), 4.14-4.11 (1H, m), 3.19-3.05 (2H, m), 2.46-2.38 (6H, m), 2.31-2.21 (2H, m), 1.67-1.63 (4H, m), 1.35 (9H, s).

Step 2: Compound 6l+Compound 27b→Compound I-27

Using compound 6l (955 mg, 0.70 mmol) and compound 27b (303 mg, 0.70 mmol), compound I-27 was synthesized according to the similar manner as described in step 8 of Example 1.

Yield: 219.9 mg, (29%)

Elemental analysis: C34H39ClN9O13S2Na(H2O)9.4 (NaHCO3)0.1

Cal'd: C, 37.85; H, 5.39; Cl, 3.28; N, 11.65; S, 5.93; Na, 2.34(%).

Found: C, 37.78; H, 5.26; Cl, 3.36; N, 11.67; S, 5.93; Na, 2.29(%).

Example 28

Synthesis of Compound I-28

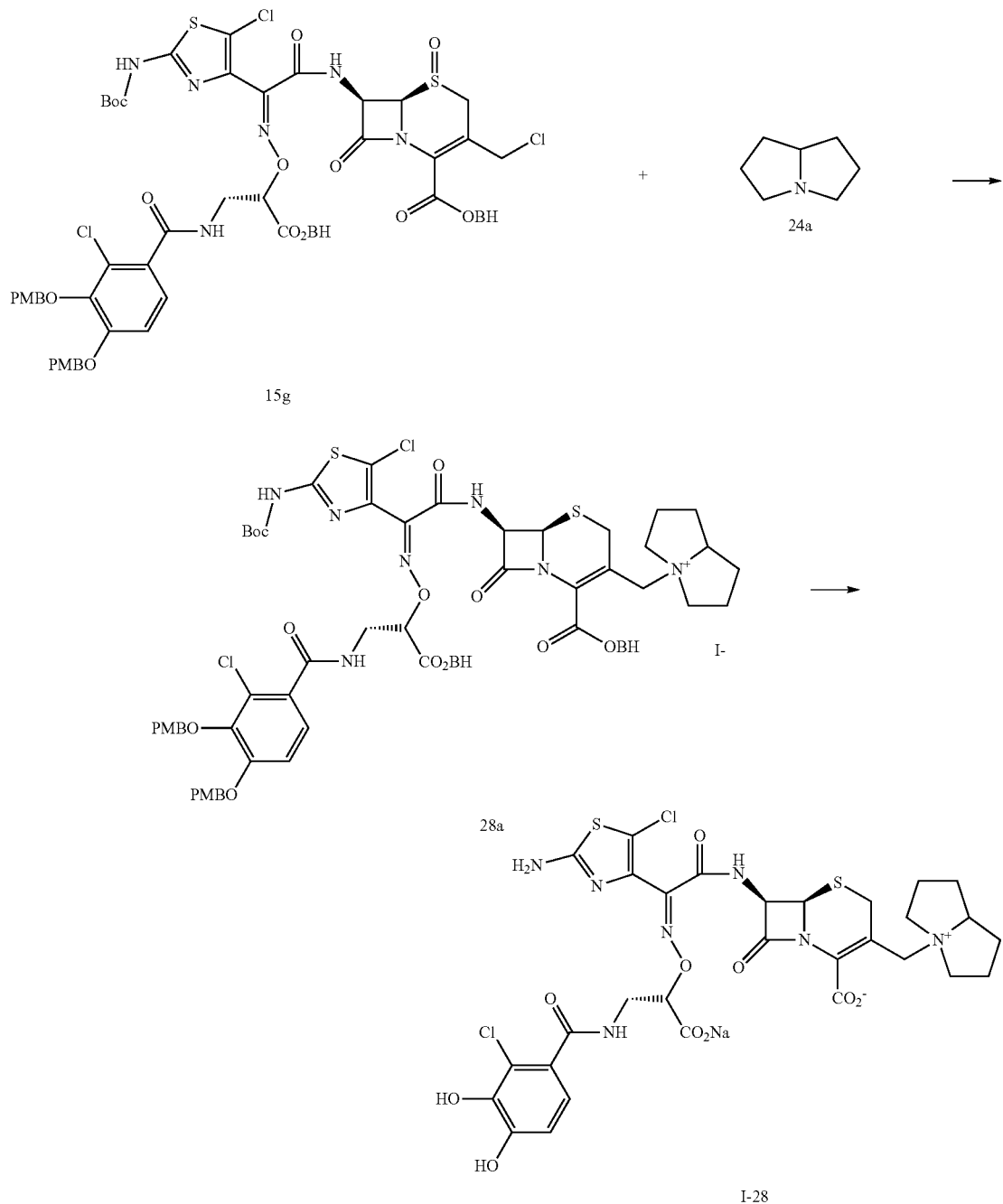

[Formula 58]

Step: Compound 15g+Compound 24a→Compound I-28

Using compound 15g (1.40 g, 1.00 mmol) and compound 24a (122 mg, 1.10 mmol), compound I-28 was synthesized according to the similar manner as described in step 8 of Example 1.

Yield: 418.1 mg, (45%)

$^1$H-NMR (D$_2$O) δ: 7.00 (1H, d, J=8.4 Hz), 6.88 (1H, d, J=8.4 Hz), 5.79 (1H, d, J=5.2 Hz), 5.23 (1H, d, J=5.2 Hz), 4.92-4.88 (1H, m), 4.60 (1H, d, J=14.0 Hz), 4.19-4.16 (1H, m), 3.95-3.17 (8H, m), 3.03 (1H, d, J=16.8 Hz), 2.40-1.82 (8H, m).

Elemental analysis: C30H30Cl2N7O10S2Na(H2O)6.5

Cal'd: C, 39.01; H, 4.69; Cl, 7.68; N, 10.61; S, 6.94; Na, 2.49(%).

Found: C, 38.97; H, 4.55; Cl, 7.64; N, 10.66; S, 6.84; Na, 2.58(%).

Example 29
Synthesis of Compound I-29
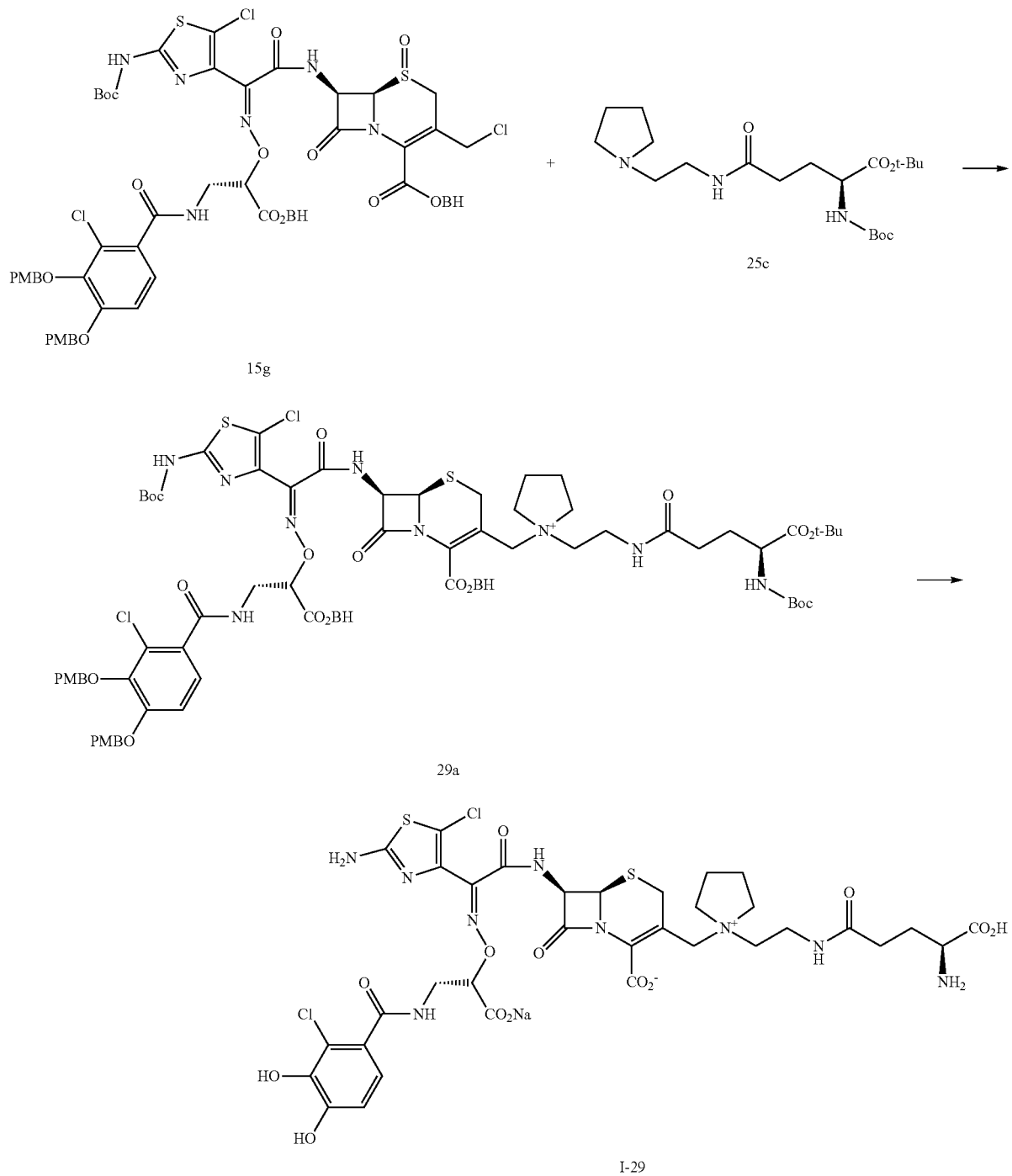
[Formula 59]
Step: Compound 15g+Compound 25c→Compound I-29
Using compound 15g (1.40 g, 1.00 mmol) and compound 25c (439 mg, 1.10 mmol), compound I-29 was synthesized according to the similar manner as described in step 8 of Example 1.
Yield: 359.0 mg, (32%)
$^1$H-NMR (D$_2$O) δ: 6.99 (1H, d, J=8.2 Hz), 6.88 (1H, d, J=8.2 Hz), 5.80 (1H, d, J=5.2 Hz), 5.24 (1H, d, J=5.2 Hz), 3.94-3.31 (13H, m), 3.07 (1H, d, J=16.3 Hz), 2.48-2.42 (2H, m), 2.23-2.10 (6H, m).
Elemental analysis: C34H38Cl2N9O13S2Na(H2O)9.1 (NaHCO3)0.1

Cal'd: C, 36.86; H, 5.11; Cl, 6.38; N, 11.35; S, 5.77; Na, 2.28(%).
Found: C, 36.96; H, 4.96; Cl, 5.96; N, 11.38; S, 5.37; Na, 2.21(%).
Example 30
Synthesis of Compound I-30
Step: Compound 15g+Compound 27b→Compound I-30
Using compound 15g (979 mg, 0.70 mmol) and compound 27b (303 mg, 0.70 mmol), compound I-30 was synthesized according to the similar manner as described in step 8 of Example 1.
Yield: 253.8 mg, (33%)
Elemental analysis: C34H38Cl2N9O13S2Na(H2O)9.3
[Formula 60]
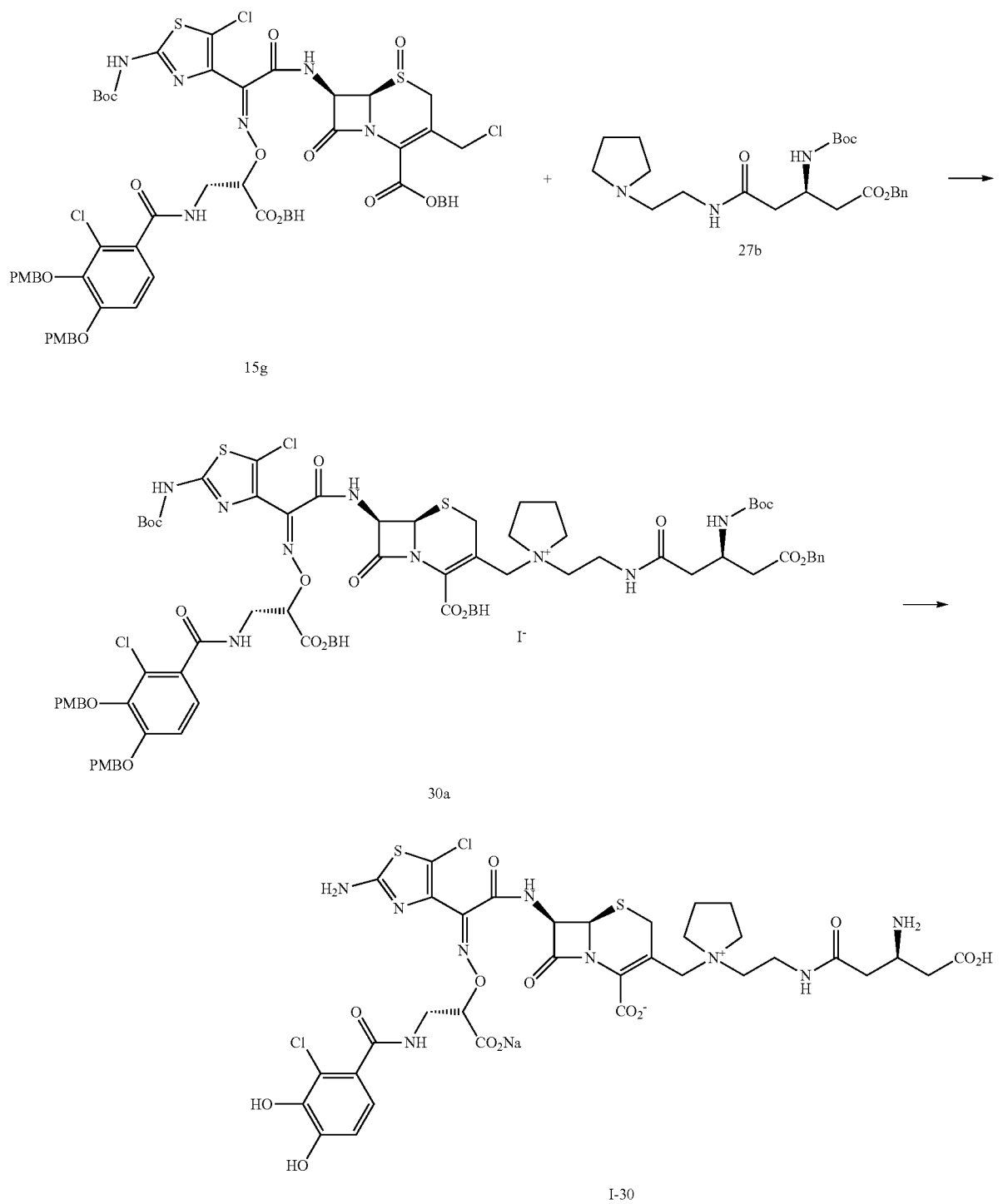

Cal'd: C, 36.91; H, 5.16; Cl, 6.41; N, 11.39; S, 5.80; Na, 2.08(%).
Found: C, 36.90; H, 5.09; Cl, 6.59; N, 11.40; S, 5.73; Na, 2.05(%).
Example 31
Synthesis of Compound I-31
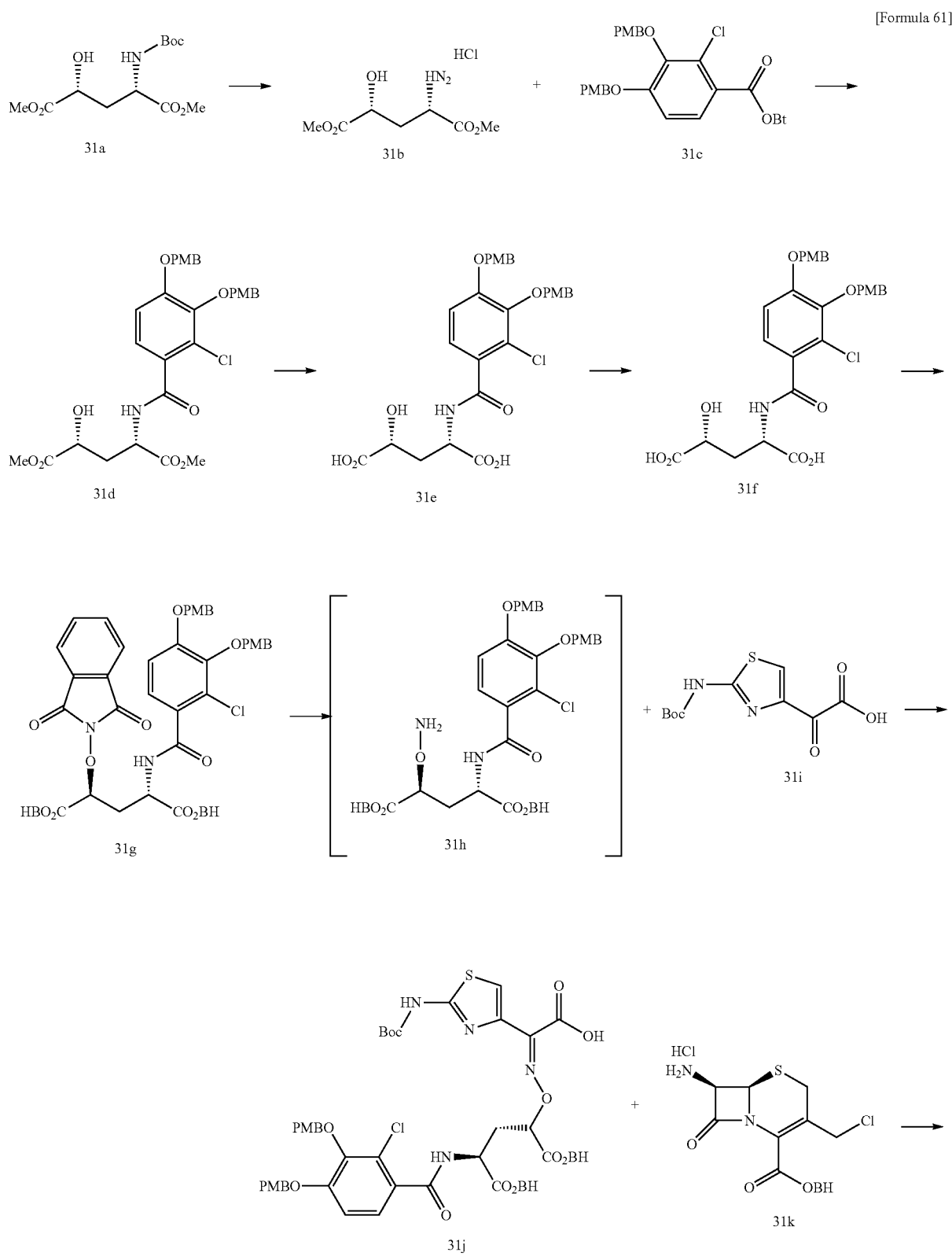
[Formula 61]

-continued

[Formula 62]

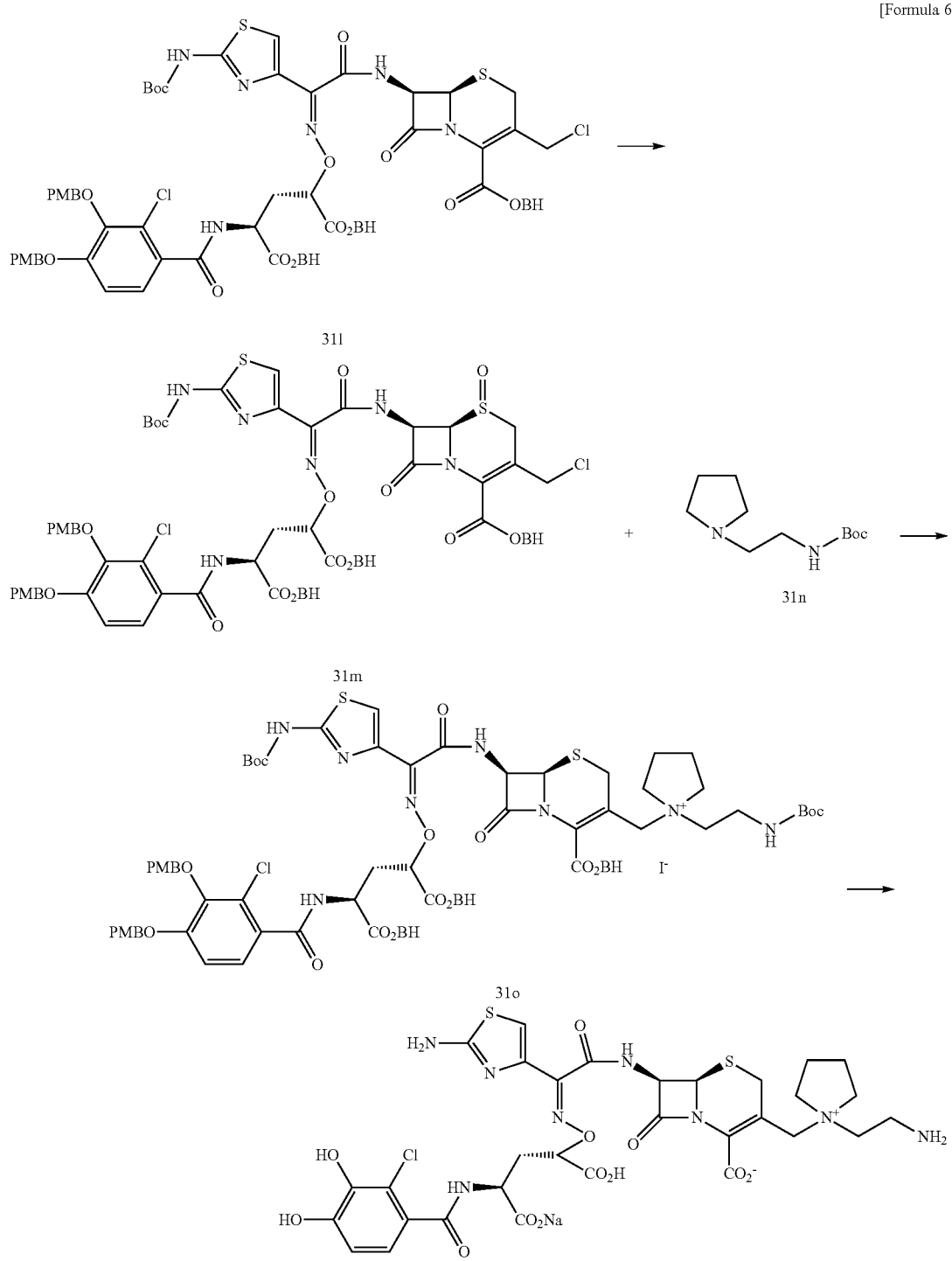

Step 1: Compound 31a→Compound 31b

A ethyl acetate (13 ml) solution of compound 31a (4.87 g, 16.7 mmol) synthesized according to Tetrahedron, 2009, 65, 6083-6089 was added a 4M hydrochloric acid ethyl acetate solution under ice-cooling, and the mixture was stirred for 2 hours at room temperature. Compound 31b was obtained by concentrating under reduced pressure. Compound 31b was used in the next reaction without further purification.

Step 2: Compound 31b+Compound 31c→Compound 31d

After the total amount of the resulting compound 31b (corresponding to 16.7 mmol) was suspended with dichloromethane (70 ml), the suspension was added sequentially with triethylamine (6.95 ml, 50.2 mmol) and compound 31c (10.04 g, 18.4 mmol) under ice-cooling, and the mixture was stirred for 1 hour at room temperature. The reaction solution was diluted with dichloromethane, and the organic layer was washed with hydrodrochloric acid, water and brine and dried over magnesium sulfate.

Step 3: Compound 31d→Compound 31e

A tetrahydrofuran (100 ml)/methanol (50 ml) solution of the total amount of the resulting compound 31d (corresponding to 16.7 mmol) was added a 2 mol/l aqueous sodium hydroxide solution (25 ml, 50 mmol) and stirred for 2 hours at room temperature. The mixture was added sequentially with water (50 ml) and 2 mol/l hydrochloric acid (30 ml) under ice-cooling and removed tetrahydrofuran under reduced pressure, after that, the precipitated solid was filtered to obtain compound 31e (6.74 g, 70%). Compound 31e was used in the next reaction without further purification.

$^1$H-NMR (DMSO-D$_6$) δ: 8.55 (1H, d, J=7.6 Hz), 7.43 (2H, d, J=8.5 Hz), 7.31 (2H, d, J=8.5 Hz), 7.26-7.15 (2H, m), 6.97 (2H, d, J=8.2 Hz), 6.87 (2H, d, J=8.2 Hz), 5.15 (2H, s), 4.87 (2H, s), 4.54-4.44 (1H, m), 4.11 (1H, dd, J=8.0, 5.1 Hz), 3.77 (3H, s), 3.74 (3H, s), 2.24-1.83 (2H, m).

Step 4: Compound 31e→Compound 31f

After a tetrahydrofuran (100 ml) solution of compound 31e (9.60 g, 16.7 mmol) was added with a tetrahydrofuran (10 ml) solution of diphenyldiazomethane (7.79 g, 40.1 mmol), the mixture was stirred overnight at room temperature. The reaction solution was concentrated under reduced pressure, subjected to silica gel column chromatography, and eluted with hexane/ethyl acetate. The fractions containing the desired compound were concentrated under reduced pressure to obtain compound 31f (11.51 g, 76%).

$^1$H-NMR (CDCl$_3$) δ: 7.49-7.27 (19H, m), 7.23-7.20 (5H, m), 6.96-6.81 (8H, m), 5.20-5.11 (1H, m), 5.09-5.08 (2H, m), 4.93-4.92 (2H, m), 4.50-4.43 (1H, m), 3.82 (3H, s), 3.79 (3H, s), 3.26 (1H, d, J=7.5 Hz), 2.75-2.67 (1H, m), 2.34-2.24 (2H, m).

Step 5: Compound 31f→Compound 31g

A tetrahydrofuran (100 ml) solution of compound 31f (10.51 g, 11.6 mmol) and N-hydroxyphthalimide (2.46 g, 15.1 mmol) was added a 2.7 M dimethylazodicarboxylic acid/toluene solution (5.15 ml, 13.9 mmol) and triphenylphosphine (3.65 g, 13.9 mmol) under ice-cooling. After the mixture was stirred for 1 hour under ice-cooling, the reaction solution was concentrated under reduced pressure, subjected to silica gel column chromatography, and eluted with hexane/ethyl acetate. The fractions containing the desired compound were concentrated under reduced pressure to obtain compound 31g (11.46 g, 94%).

Step 6: Compound 31g+Compound 31i→Compound 31j

After a dichloromethane (100 mL) solution of compound 31g (11.46 g, 10.9 mmol) was cooled to −40° C., the solution was added methylhydrazine (0.61 mL, 11.44 mmol) and stirred for 1 hour under ice-cooling. After the reaction mixture was filtered, the filtrate was added methanol (50 mL) and compound 31i (2.97 g, 10.9 mmol), and stirred for 1 hour at room temperature. The reaction solution was diluted with dichloromethane, and the organic layer was washed with water and brine, and dried over magnesium sulfate. After magnesium sulfate was filtered out, compound 31j (13.75 g, 107%) was obtained by concentrating the filtrate. Compound 31j was used in the next reaction without further purification.

Step 7: Compound 31j+Compound 31k→Compound 31l

The total amount of the resulting compound 31j (corresponding to 10.9 mmol) and compound 31k (4.92 g, 10.9 mmol) were suspended and cooled to −40° C., then added dichlorophenyl phosphate (2.44 ml, 16.4 mmol). After that N-methylmorpholine (5.39 ml, 49.1 mmol) was added dropwise at −40° C., and stirred for 1 hour at −40° C. to −30° C. The reaction solution was diluted with dichloromethane, and washed with 0.2 mol/l hydrochloric acid, an aqueous saturated sodium hydro carbonate solution, and brine, and dried over magnesium sulfate. After magnesium sulfate was filtered out, the filtrate was concentrated under reduced pressure, subjected to silica gel column chromatography and eluted with hexane/ethyl acetate. The fractions containing the desired compound were concentrated under reduced pressure, compound 31l (13.59 g, 79%) was obtained as a crude product. Compound 31l was used in the next reaction without further purification.

Step 8: Compound 31l→Compound 31m

After a dichloromethane (140 mL) solution of the total amount of the resulting compound 31l (13.59 g, corresponding to 8.64 mmol) was cooled to −50° C., the solution was added a dichloromethane (25 mL) solution of mCPBA (2.29 g, 8.64 mmol), and stirred for 1 hour at −50° C. to −40° C. The reaction solution was diluted with dichloromethane, and washed with a 5% aqueous sodium hydrosulfite solution, an aqueous saturated sodium hydrocarbonate solution, and brine, and dried over magnesium sulfate. After magnesium sulfate was filtered out, the filtrate was concentrated under reduced pressure, subjected to silica gel column chromatography and eluted with hexane/ethyl acetate. The fractions containing the desired compound were concentrated under reduced pressure to obtain compound 31m (8.85 g, 65%).

$^1$H-NMR (CDCl$_3$) δ: 9.33 (1H, t, J=6.0 Hz), 8.61 (1H, s), 8.27 (1H, d, J=9.2 Hz), 7.44 (2H, d, J=7.5 Hz), 7.35-7.26 (18H, m), 7.24-7.16 (14H, m), 6.95-6.72 (10H, m), 5.44 (1H, dd, J=9.2, 4.9 Hz), 5.34-5.30 (1H, m), 4.81 (6H, br s), 4.36 (1H, d, J=4.9 Hz), 3.81-3.76 (7H, m), 3.37 (1H, d, J=18.5 Hz), 2.78-2.69 (2H, m), 2.52-2.42 (1H, m), 1.53 (9H, s).

Step 9: Compound 31m+Compound 31n→Compound I-31

Using compound 31m (1.59 g, 1.00 mmol) and compound 31n (236 mg, 1.10 mmol), compound I-31 was synthesized according to the similar manner as described in step 8 of Example 1.

Yield: 226.3 mg, (18%)

$^1$H-NMR (D$_2$O) δ: 7.08 (1H, d, J=8.1 Hz), 6.99 (1H, s), 6.90 (1H, d, J=8.1 Hz), 5.69 (1H, d, J=5.0 Hz), 5.28 (1H, d, J=5.0 Hz), 4.20 (1H, d, J=13.6 Hz), 3.81 (1H, d, J=16.9 Hz), 3.73-3.36 (10H, m), 2.30-2.13 (6H, m).

Elemental analysis: C31H34ClN8O12S2Na(H2O)7.7

Cal'd: C, 38.31; H, 5.12; Cl, 3.65; N, 11.53; S, 6.60; Na, 2.37(%).

Found: C, 38.31; H, 5.31; Cl, 3.84; N, 11.70; S, 6.51; Na, 2.70(%).

Example 32

Synthesis of Compound I-32

[Formula 63]

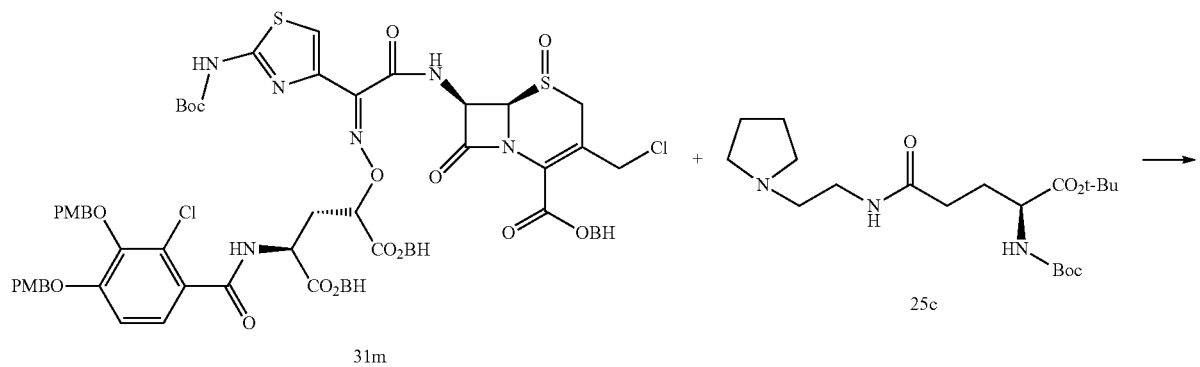

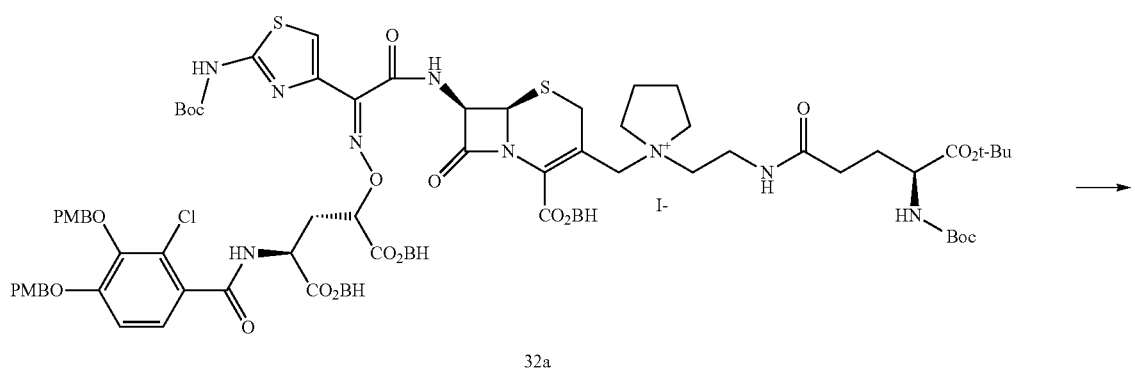

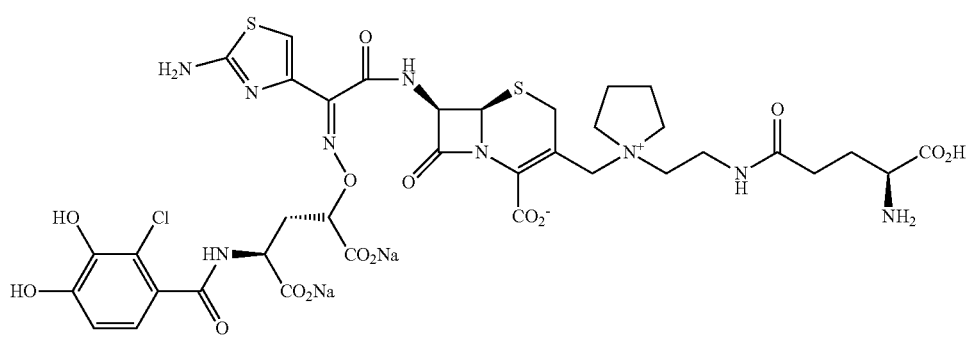

Step: Compound 31m+Compound 25c→Compound I-32

Using compound 31m (1.59 g, 1.00 mmol) and compound 25c (439 mg, 1.10 mmol), compound I-32 was synthesized according to the similar manner as described in step 8 of Example 1.

Yield: 446.0 mg, (38%)

$^1$H-NMR (D$_2$O) δ: 7.09 (1H, d, J=8.4 Hz), 6.99 (1H, s), 6.91 (1H, d, J=8.4 Hz), 5.63 (1H, d, J=4.7 Hz), 5.23 (1H, d, J=4.7 Hz), 4.74-4.67 (2H, m), 4.05 (1H, d, J=15.4 Hz), 3.84-3.36 (10H, m), 2.50-2.12 (10H, m).

Elemental analysis: C36H40ClN9O15S2Na2(H2O)8.8

Cal'd: C, 37.83; H, 5.08; Cl, 3.10; N, 11.03; S, 5.61; Na, 4.02(%).

Found: C, 37.83; H, 5.08; Cl, 3.13; N, 11.15; S, 5.54; Na, 3.82(%).

Compounds shown in the following Reference Examples also have wide antimicrobial spectrum against various Gram negative bacteria and/or Gram positive bacteria, and exhibits strong antimicrobial activity against beta-lactamase producing Gram negative bacteria.

117
Reference Example 1
Synthesis of Compound II-1
[Formula 64]
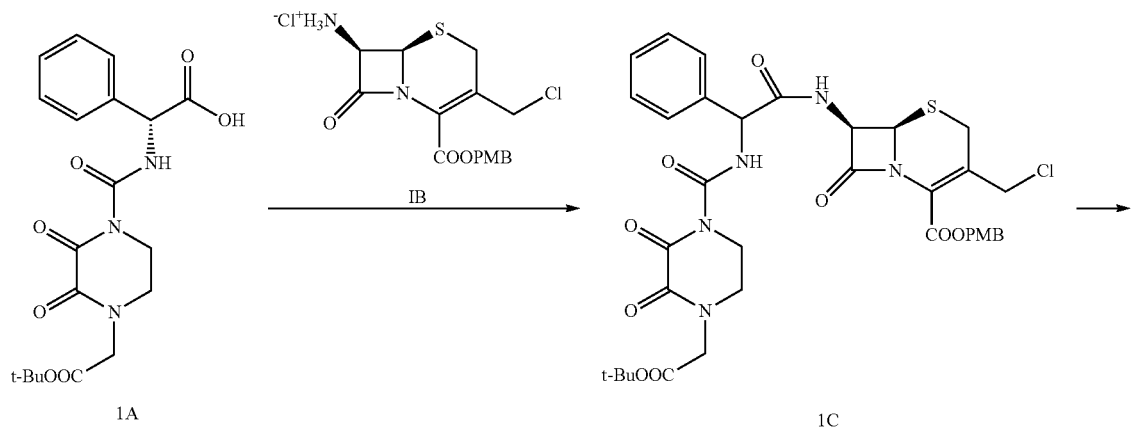
1A + IB → 1C
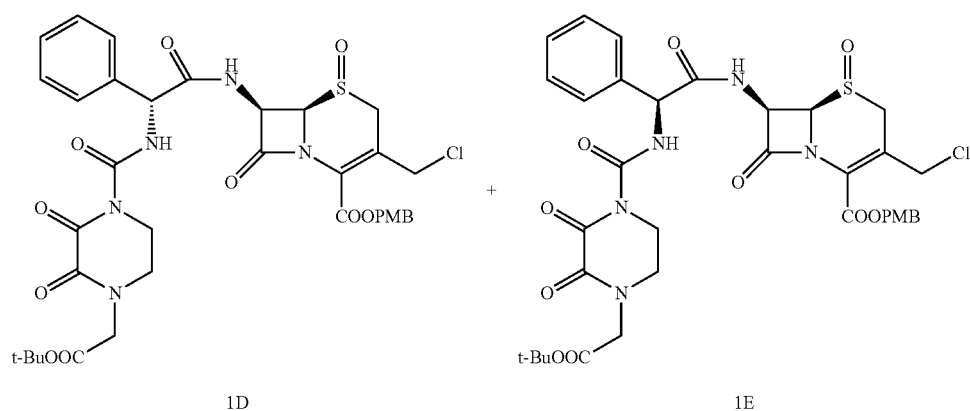
1D + 1E
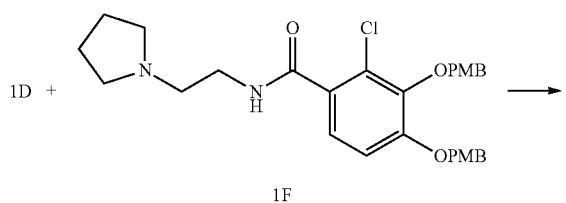
1D + 1F →
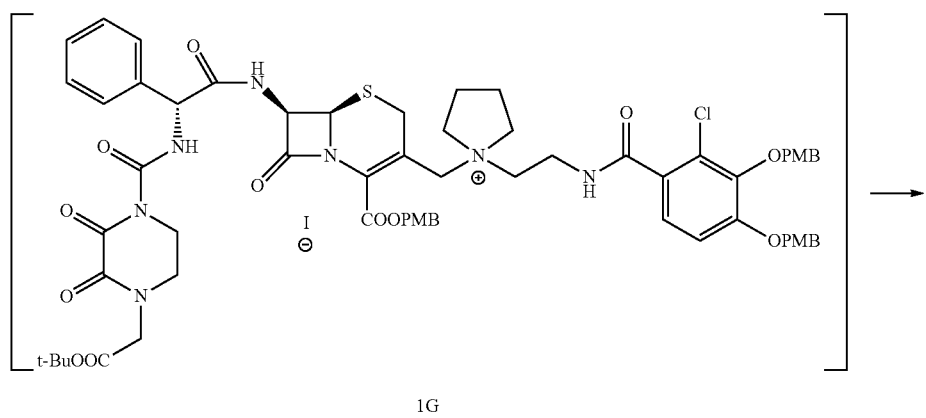
1G

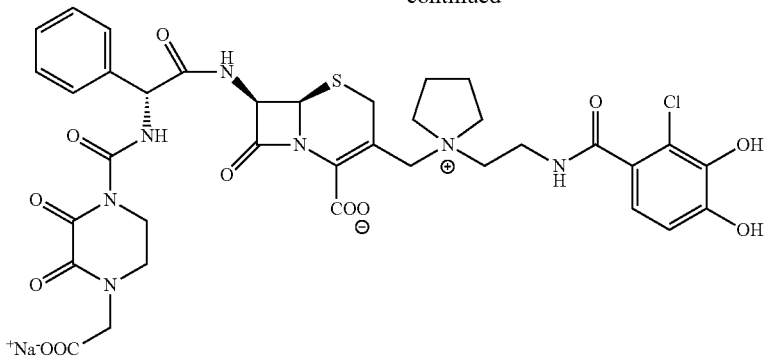

II-1

Step 1: Synthesis of Compound 1C

After a dichloromethane (10 mL) solution of compound 1A (2.16 g, 5.0 mmol) was ice-cooled, oxalyl chloride (613 μL, 7.0 mmol) and DMF (1 droplet) were added, and the mixture was stirred at room temperature for 4 hours. The solvent was distilled off under reduced pressure, to the resulting residue was added toluene, and this was distilled off again under reduced pressure, and dried under reduced pressure.

The resulting residue was dissolved in dichloromethane (20 mL), the solution was cooled to −40° C., thereafter, compound 1B (2.13 g, 5.25 mmol) and pyridine (613 μL, 7.0 mmol) were added, and the mixture was stirred at −40° C. for 2 hours. To the resulting reaction mixture was added 0.2 mol/L hydrochloric acid, dichloromethane was distilled off under reduced pressure, and this was extracted with ethyl acetate. The organic layer was sequentially washed with water, a 5% aqueous sodium bicarbonate solution and brine, and dried over anhydrous magnesium sulfate. The inorganic substances were removed by filtration, and the filtrate was concentrated under reduced pressure. The resulting crude product was purified by silica gel column chromatography (hexane-ethyl acetate) to obtain compound 1C (2.56 g, yield 68%) as an orange foam.

$^1$H-NMR (CDCl$_3$) δ: 1.47 (9H, s), 3.32-3.68 (4H, m), 3.80 (3H, d, J=2.7 Hz), 4.03-4.25 (4H, m), 4.40 (1H, d, J=4.9 Hz), 4.45 (1H, d, J=12.4 Hz), 4.91 (1H, dd, J=26.1, 4.9 Hz), 5.17-5.23 (2H, m), 5.57 (1H, t, J=6.8 Hz), 5.79 (1H, dq, J=17.7, 4.7 Hz), 6.86-6.89 (3H, m), 7.29-7.41 (7H, m), 9.99 (1H, dd, J=27.5, 6.8 Hz).

Step 2: Synthesis of Compound 1D and Compound 1E

After a dichloromethane (18 ml) solution of compound 1C (2.56 g, 3.39 mmol) was cooled to −40° C., a dichloromethane (12 ml) solution of mCPBA (989 mg, 3.72 mmol) was added dropwise over 5 minutes. After stirred at −40° C. for 30 minutes, a 15% aqueous sodium thiosulfate solution was added, dichloromethane was distilled off under reduced pressure, and this was extracted with ethyl acetate. The organic layer was sequentially washed with a 5% aqueous sodium bicarbonate solution and brine, and dried over anhydrous sodium sulfate. The inorganic substances were removed by filtration, and the filtrate was concentrated under reduced pressure. The resulting crude product was purified by silica gel column chromatography (hexane-ethyl acetate) to obtain compound 1D (1.09 g, yield 42%) as a white solid, and compound 1E (773 mg, yield 30%) as a white foam.

Compound 1D: $^1$H-NMR (CDCl$_3$) δ: 1.47 (9H, s), 3.36 (1H, d, J=18.4 Hz), 3.53-3.67 (2H, m), 3.72 (1H, d, J=18.4 Hz), 3.81 (3H, s), 4.03-4.27 (6H, m), 4.47 (1H, d, J=4.7 Hz), 4.85 (1H, d, J=12.4 Hz), 5.24 (2H, d, J=1.8 Hz), 5.46 (1H, d, J=5.9 Hz), 6.03 (1H, dd, J=10.0, 4.7 Hz), 6.89 (2H, d, J=8.4 Hz), 7.09 (1H, d, J=10.0 Hz), 7.32-7.41 (7H, m), 9.95 (1H, d, J=5.9 Hz).

Compound 1E: $^1$H-NMR (CDCl$_3$) δ: 1.47 (9H, s), 3.50-3.67 (3H, m), 3.79 (3H, s), 3.84 (1H, d, J=18.8 Hz), 3.99-4.20 (5H, m), 4.32 (1H, d, J=12.3 Hz), 4.65 (1H, d, J=4.6 Hz), 4.82 (1H, d, J=12.3 Hz), 5.21 (2H, d, J=5.6 Hz), 5.49 (1H, d, J=6.5 Hz), 5.98 (1H, dd, J=9.6, 4.9 Hz), 6.87 (2H, d, J=8.5 Hz), 7.23 (1H, d, J=9.6 Hz), 7.29-7.42 (7H, m), 9.94 (1H, d, J=6.5 Hz).

Step 3: Synthesis of Compound II-1

After a DMA (1 mL) solution of compound 1F (263 mg, 0.50 mmol) was cooled to 15° C., compound 1D (386 mg, 0.50 mmol) was added, and the mixture was degassed under reduced pressure. Sodium iodide (150 mg, 1.0 mmol) was added, and the mixture was stirred at 15° C. for 6 hours. After DMF (3.0 mL) was added, this was cooled to −40° C., phosphorus tribromide (94 μL, 1.0 mmol) was added, and the mixture was stirred at −40° C. for 30 minutes. The reaction mixture was slowly added to an ice-cooled 5% aqueous sodium chloride solution. The precipitated solid was filtered, washed with water, suspended in water, and lyophilized to obtain compound 1G as a brown solid. The resulting compound 1G was used in the next reaction without purification.

The total amount of the resulting compound 1G was dissolved in dichloromethane (6 ml), the solution was cooled to −40° C., thereafter, anisole (546 μL, 5.0 mmol) and a 2 mol/L-aluminum chloride/nitromethane solution (2.5 mL, 5.0 mmol) were sequentially added, and the mixture was stirred at 0° C. for 30 minutes. To the reaction solution were added diisopropyl ether, and a small amount of water, the mixture was stirred to generate the precipitate, and the supernatant was removed by decantation. To insolubles which had been left in a container were added dilute hydrochloric acid and acetonitrile, the mixture was stirred to completely dissolve the materials, diisopropyl ether was added, and the aqueous layer was separated. After the organic layer was extracted with water again, all aqueous layers were combined, the HP20-SS resin was added, and acetonitrile was distilled off under reduced pressure. The resulting mixed solution was purified by ODS column chromatography (water-acetonitrile). To the fractions containing the desired compound was added a 0.2 mol/L aqueous sodium hydroxide solution, pH was adjusted to 6.0, and a small amount of dry ice was added. The resulting solution was concentrated under reduced pressure, and lyophilized to obtain compound II-1 (185 mg, yield 44%) as a white powder.

$^1$H-NMR (D$_2$O) δ: 2.21 (4H, br s), 3.41-3.83 (12H, m), 3.96-4.15 (6H, m), 5.03 (1H, d, J=4.8 Hz), 5.37 (1H, s), 5.67 (1H, d, J=4.8 Hz), 6.83 (1H, d, J=8.5 Hz), 6.92 (1H, d, J=8.5 Hz), 7.34-7.47 (5H, m).

MS (m+1)=828.38

Elemental analysis: C$_{36}$H$_{37}$ClN$_7$O$_{12}$SNa.6.6H$_2$O

Cal'd: C, 44.62; H, 5.22; Cl, 3.66; N, 10.12; S, 3.31(%).

Found: C, 44.58; H, 4.99; Cl, 3.84; N, 10.12; S, 3.29(%).

Reference Example 2

Synthesis of Compound II-2 was obtained as a white powder, from compound 1D (386 mg, 0.50 mmol) and compound 2A (276 mg, 0.50 mmol).

$^1$H-NMR (D$_2$O) δ: 2.15 (2H, d, J=17.1 Hz), 2.45 (4H, br s), 2.68-2.80 (2H, br m), 3.05 (3H, s), 3.31 (1H, d, J=16.9 Hz), 3.72-4.13 (10H, m), 4.21 (1H, t, J=6.9 Hz), 4.57 (1H, d, J=11.7 Hz), 5.18 (1H, d, J=4.8 Hz), 5.47 (1H, s), 5.73 (1H, d, J=4.8 Hz), 6.87 (1H, d, J=8.3 Hz), 6.91 (1H, d, J=8.3 Hz), 7.45-7.51 (5H, m).

MS (m+1)=854.39

Elemental analysis: C$_3$H$_{39}$ClN$_7$O$_{12}$SNa.7.2H$_2$O.0.1NaHCO$_3$.0.2NaCl

[Formula 65]

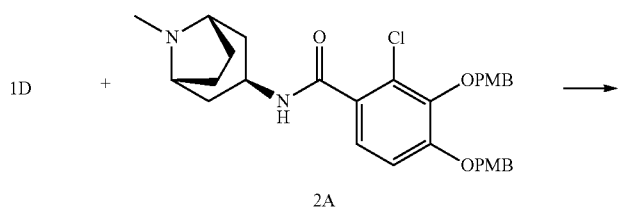

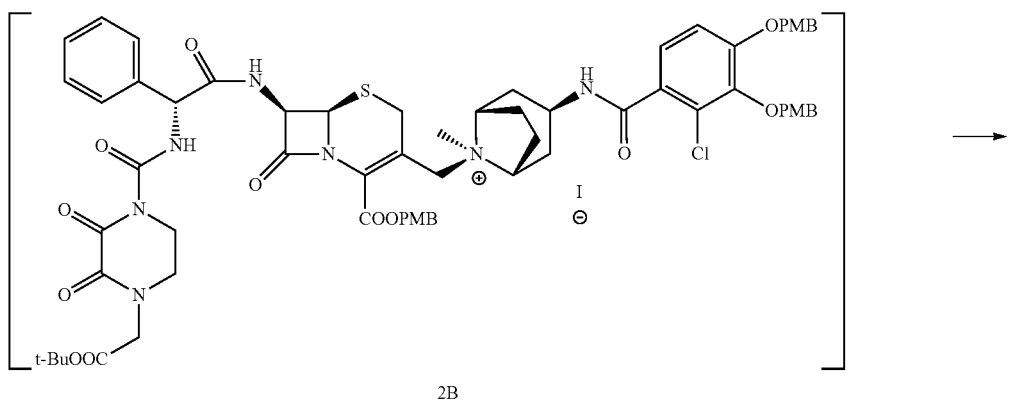

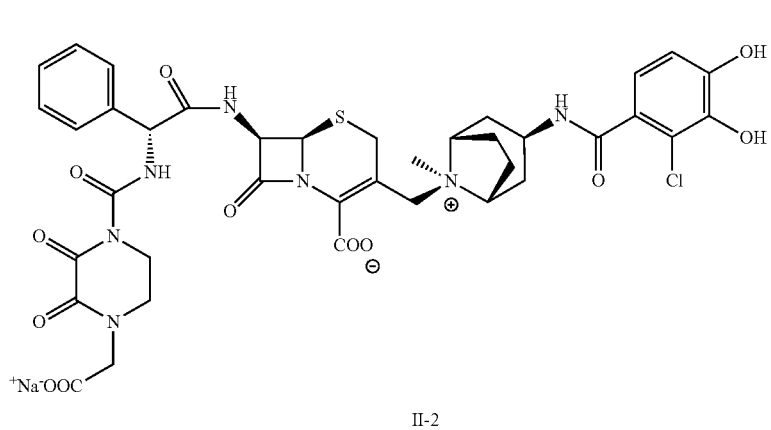

Step: Synthesis of Compound II-2

According to the similar manner as described in step 3 of Reference Example 1, compound II-2 (178 mg, yield 41%)

Cal'd: C, 44.60; H, 5.26; Cl, 4.15; N, 9.56; S, 3.13; Na, 2.91(%).

Found: C, 44.53; H, 5.18; Cl, 4.22; N, 9.63; S, 3.08; Na, 2.87(%).

Reference Example 3

Synthesis of Compound II-3

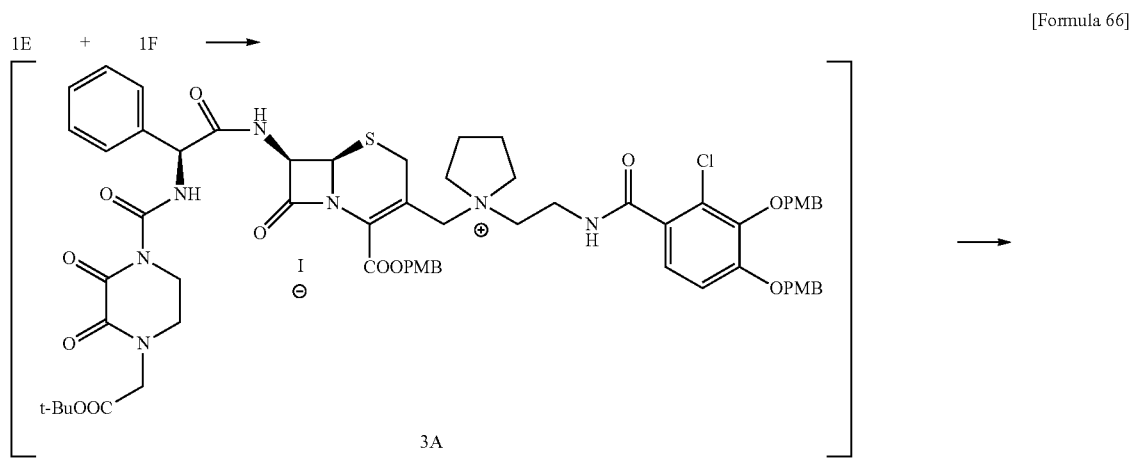

[Formula 66]

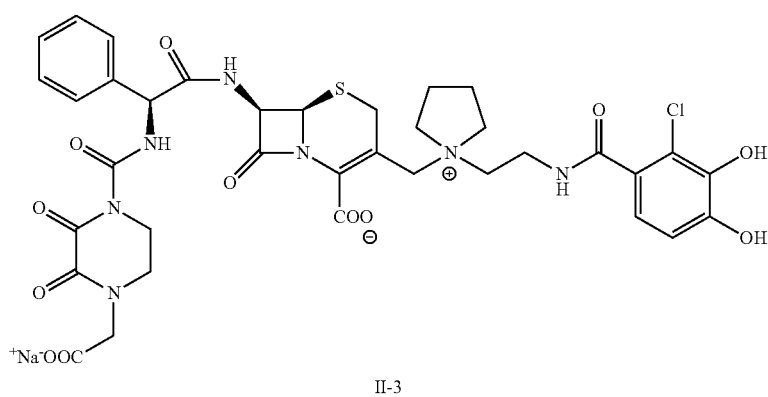

Step: Synthesis of Compound II-3

According to the similar manner as described in step 3 of Reference Example 1, compound II-3 (200 mg, yield 47%) was obtained as a white powder, from compound 1E (386 mg, 0.50 mmol) and compound 1F (263 mg, 0.50 mmol).

$^1$H-NMR (D$_2$O) δ: 2.23 (4H, s), 3.46-4.23 (18H, m), 5.22 (1H, d, J=4.9 Hz), 5.41 (1H, s), 5.48 (1H, d, J=4.9 Hz), 6.85 (1H, d, J=8.3 Hz), 6.95 (1H, d, J=8.3 Hz), 7.40-7.45 (5H, m).

MS (m+1)=828.38

Elemental analysis: C$_{36}$H$_{37}$ClN$_7$O$_{12}$SNa.5.3H$_2$O.0.1NaHCO$_3$

Cal'd: C, 45.44; H, 5.04; Cl, 3.72; N, 10.28; S, 3.36; Na, 2.65(%).

Found: C, 45.47; H, 5.07; Cl, 3.77; N, 10.29; S, 3.36; Na, 2.70(%).

Reference Example 4
Synthesis of Compound II-4
[Formula 67]
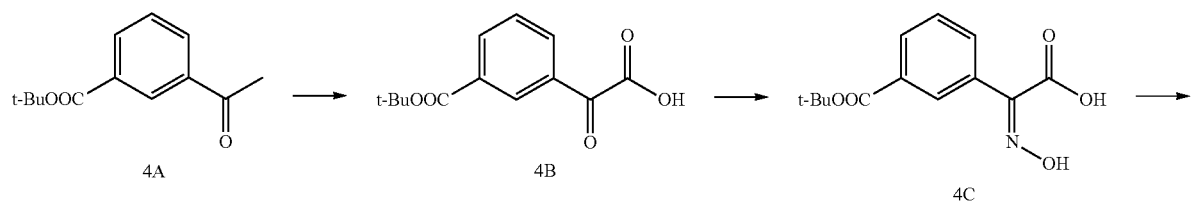
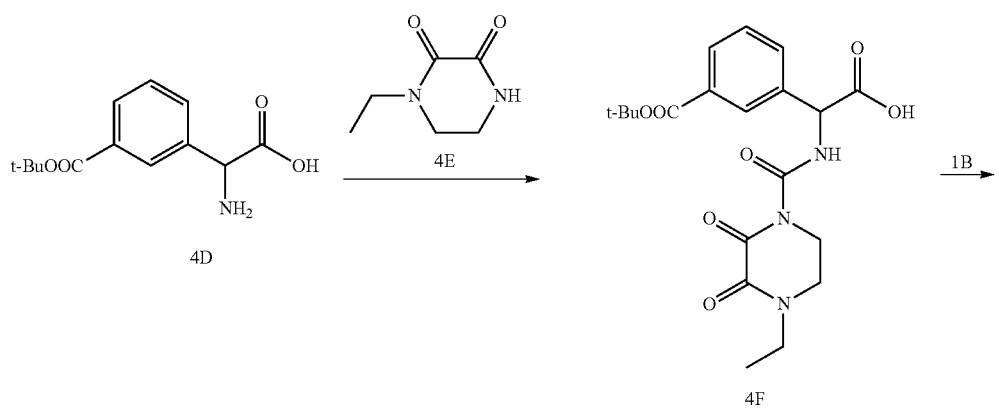
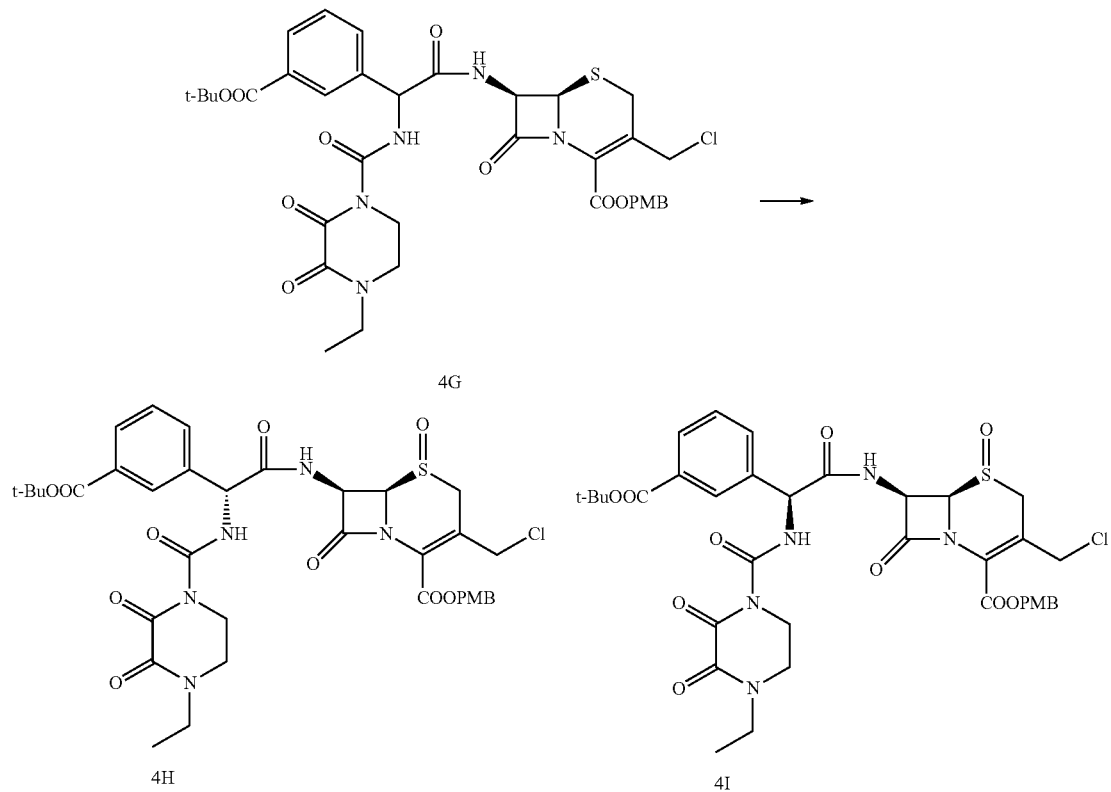

4H + 1F ⟶ 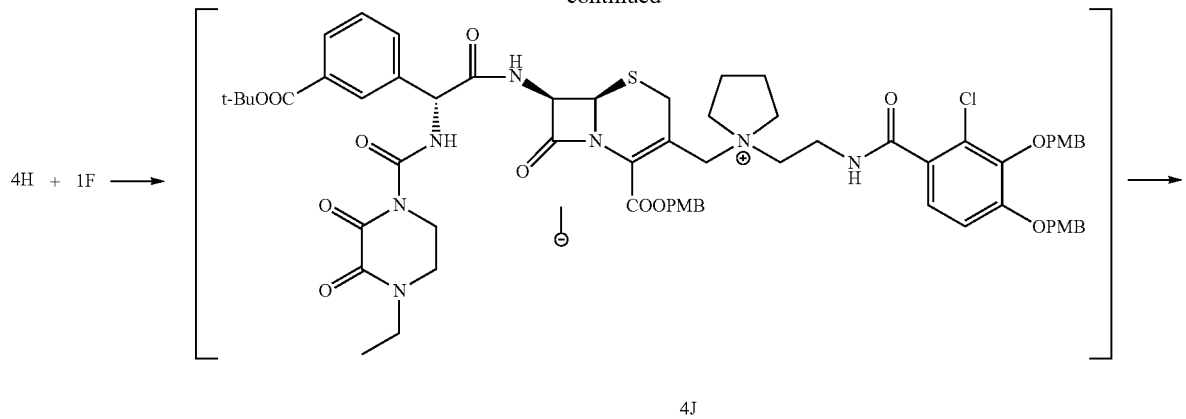

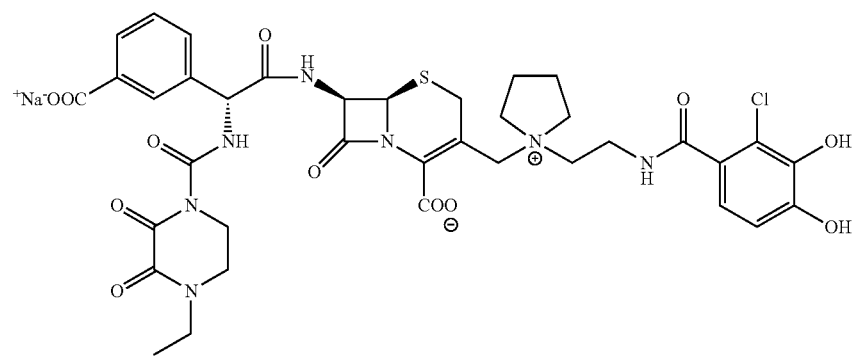

Step 1: Synthesis of Compound 4B

To a pyridine (120 mL) solution of the known compound 4A (12.06 g, 54.8 mmol) was added selenium dioxide (12.15 g, 110 mmol), and the mixture was stirred at 90° C. for 4 hours. Insolubles were removed by Celite-filtration, the solvent was distilled off under reduced pressure, 1 mol/L hydrochloric acid was added, and this was extracted with ethyl acetate. The organic layer was washed with brine, and dried over anhydrous magnesium sulfate. Inorganic substances were removed by filtration, the filtrate was concentrated under reduced pressure, and dried under reduced pressure to obtain compound 4B (14.45 g, yield 90%) as an orange oil.

$^1$H-NMR (CDCl$_3$) δ: 1.63 (9H, s), 7.61 (1H, t, J=7.8 Hz), 8.31 (1H, d, J=7.8 Hz), 8.52 (1H, d, J=7.8 Hz), 8.89 (1H, d, J=1.7 Hz).

Step 2: Synthesis of Compound 4D

To a methanol (60 mL) solution of compound 4B (5.89 g, 20 mmol) were added sodium acetate (1.81 g, 22 mmol) and hydroxylammonium chloride (1.53 g, 22 mmol), and the mixture was stirred at room temperature overnight. The solvent was distilled off under reduced pressure, water was added, and this was extracted with ethyl acetate. The organic layer was washed with brine, and dried over anhydrous sodium sulfate. The inorganic substances were removed by filtration, and the filtrate was concentrated under reduced pressure, and dried under reduced pressure to obtain compound 4C as a yellow syrup-like substance.

After the total amount of the resulting compound 4C was dissolved in methanol (50 mL), 10% palladium/carbon (50% water-containing product) (2.13 g, 1.0 mmol) was added, and the mixture was stirred at room temperature overnight under 1 atm hydrogen. After insolubles were removed by Celite-filtration, the solvent was distilled off under reduced pressure. To the residue was added diisopropyl ether, and the resulted solid was filtered to obtain compound 4D (3.78 g, yield 75%) as a white solid.

$^1$H-NMR (DMSO-d$_6$) δ: 1.56 (9H, s), 4.30 (1H, s), 7.45 (1H, t, J=7.8 Hz), 7.62 (1H, d, J=7.8 Hz), 7.81 (1H, d, J=7.8 Hz), 7.94 (1H, s).

Step 3: Synthesis of Compound 4F

After a dichloromethane (30 mL) solution of compound 4E (1.54 g, 10.8 mmol) was ice-cooled, triethylamine (2.07 mL, 14.9 mmol) and trimethylchlorosilane (1.52 mL, 11.9 mmol) were added, and the mixture was stirred at room temperature for 1 hour. After the reaction mixture was cooled to −30° C., triphosgene (1.22 g, 4.1 mmol) was added, and the mixture was stirred at −30° C. for 1 hour. After the solvent was distilled off under reduced pressure, this was dried under reduced pressure to obtain the residue A as a pale orange solid.

After a dichloromethane (30 mL) solution of compound 4D (2.72 g, 10.8 mmol) was ice-cooled, triethylamine (3.15 mL, 22.7 mmol) and trimethylchlorosilane (3.04 mL, 23.8 mmol) were added, and the mixture was stirred at room temperature for 2 hours. After the reaction mixture was cooled to −40° C., the residue A which had been obtained in the above-mentioned paragraph was dissolved in dichloromethane (30 mL), this solution was added, the mixture was stirred at −40° C. for 30 minutes and, thereafter, the mixture was further stirred for 1 hour under ice-cooling. To the reaction mixture was added water, dichloromethane was distilled off under reduced pressure, and ethyl acetate was added. After pH was adjusted to 8.0 with an aqueous saturated sodium bicarbonate solution, the aqueous layer was separated. After the separated aqueous layer was adjusted to pH=2.0 with 1 mol/L hydrochloric acid, this was extracted with ethyl acetate. The organic layer was sequentially washed with water and brine, and dried over anhydrous magnesium sulfate. The inorganic substances were removed by filtration, and the filtrate was concentrated under reduced pressure, and dried under reduced pressure to obtain compound 4F (3.92 g, yield 86%) as a white solid.

$^1$H-NMR (CDCl$_3$) δ: 1.22 (3H, t, J=7.2 Hz), 1.59 (9H, s), 3.56 (4H, dd, J=14.5, 7.1 Hz), 4.07 (2H, dd, J=6.8, 4.4 Hz), 5.56 (1H, d, J=6.4 Hz), 7.43 (1H, t, J=7.7 Hz), 7.61 (1H, d, J=7.7 Hz), 7.96 (1H, d, J=7.7 Hz), 8.05 (1H, s), 9.96 (1H, d, J=6.4 Hz).

Step 4: Synthesis of Compound 4G

According to the similar manner as described in step 1 of Reference Example 1, compound 4G (3.23 g, yield 84%) was obtained as a yellow foam, from compound 4F (2.10 g, 5.0 mmol) and compound 1B (2.43 g, 5.0 mmol).

$^1$H-NMR (CDCl$_3$) δ: 1.21 (3H, dd, J=13.1, 6.9 Hz), 1.54 (9H, d, J=9.1 Hz), 3.39-3.62 (6H, m), 3.79 (3H, d, J=3.9 Hz), 3.88-4.05 (2H, m), 4.26-4.50 (2H, m), 4.90 (1H, dd, J=30.6, 4.8 Hz), 5.19 (2H, dd, J=6.2, 4.2 Hz), 5.68-5.85 (2H, m), 6.85-6.89 (2H, m), 7.28-7.43 (4H, m), 7.57 (1H, t, J=7.9 Hz), 7.93 (1H, t, J=8.9 Hz), 8.02 (1H, s), 10.11 (1H, dd, J=51.5, 6.9 Hz).

Step 5: Synthesis of Compound 4H and Compound 4I

According to the similar manner as described in step 2 of Reference Example 1, compound 4H (1.46 g, yield 44%) as a yellow foam, and compound 4I (1.19 g, yield 36%) as a yellow foam were obtained, from compound 4G (3.23 g, 4.19 mmol).

Compound 4H: $^1$H-NMR (CDCl$_3$) δ: 1.20 (3H, t, J=7.1 Hz), 1.56 (9H, s), 3.36-3.53 (5H, m), 3.72 (1H, d, J=18.5 Hz), 3.80 (3H, s), 4.05 (2H, dd, J=10.8, 6.5 Hz), 4.30 (1H, d, J=12.3 Hz), 4.53 (1H, d, J=4.6 Hz), 4.75 (1H, d, J=12.3 Hz), 5.24 (2H, d, J=1.8 Hz), 5.66 (1H, d, J=6.0 Hz), 6.03 (1H, dd, J=9.8, 4.6 Hz), 6.89 (2H, d, J=8.2 Hz), 7.32-7.39 (4H, m), 7.56 (1H, d, J=7.6 Hz), 7.94 (1H, d, J=7.6 Hz), 8.02 (1H, s), 10.03 (1H, d, J=6.0 Hz).

Compound 4I: $^1$H-NMR (CDCl$_3$) δ: 1.20 (3H, t, J=7.2 Hz), 1.56 (9H, s), 3.45-3.58 (5H, m), 3.78 (3H, s), 3.85 (1H, d, J=18.3 Hz), 3.97-4.09 (2H, m), 4.33 (1H, d, J=12.3 Hz), 4.61 (1H, d, J=3.4 Hz), 4.84 (1H, d, J=12.3 Hz), 5.21 (2H, d, J=2.9 Hz), 5.56 (1H, d, J=6.6 Hz), 5.94 (1H, dd, J=9.5, 4.6 Hz), 6.86 (2H, d, J=8.6 Hz), 7.31 (2H, d, J=8.6 Hz), 7.36-7.41 (2H, m), 7.58 (1H, d, J=7.9 Hz), 7.92 (1H, d, J=7.9 Hz), 8.03 (1H, s), 9.96 (1H, d, J=6.6 Hz).

Step 6: Synthesis of Compound II-4

According to the similar manner as described in step 3 of Reference Example 1, compound II-4 (229 mg, yield 53%) was obtained as white powder, from compound 4H (393 mg, 0.50 mmol) and compound 1F (263 mg, 0.50 mmol).

$^1$H-NMR (D$_2$O) δ: 1.18 (3H, t, J=7.2 Hz), 2.20 (4H, s), 3.36-3.96 (17H, m), 4.10 (1H, d, J=13.9 Hz), 5.10 (1H, d, J=4.9 Hz), 5.48 (1H, s), 5.68 (1H, d, J=4.9 Hz), 6.82 (1H, d, J=8.5 Hz), 6.91 (1H, d, J=8.5 Hz), 7.45 (1H, t, J=7.4 Hz), 7.57 (1H, d, J=7.4 Hz), 7.85 (1H, d, J=7.4 Hz), 7.93 (1H, s).

MS (m+1)=842.50

Elemental analysis: C$_{37}$H$_{39}$ClN$_7$O$_{12}$SNa.7.8H$_2$O.0.1NaCl

Cal'd: C, 43.97; H, 5.45; Cl, 3.86; N, 9.70; S, 3.17; Na, 2.50(%).

Found: C, 43.93; H, 5.27; Cl, 3.94; N, 9.67; S, 3.12; Na, 2.57(%).

Reference Example 5

Synthesis of Compound II-5

[Formula 68]

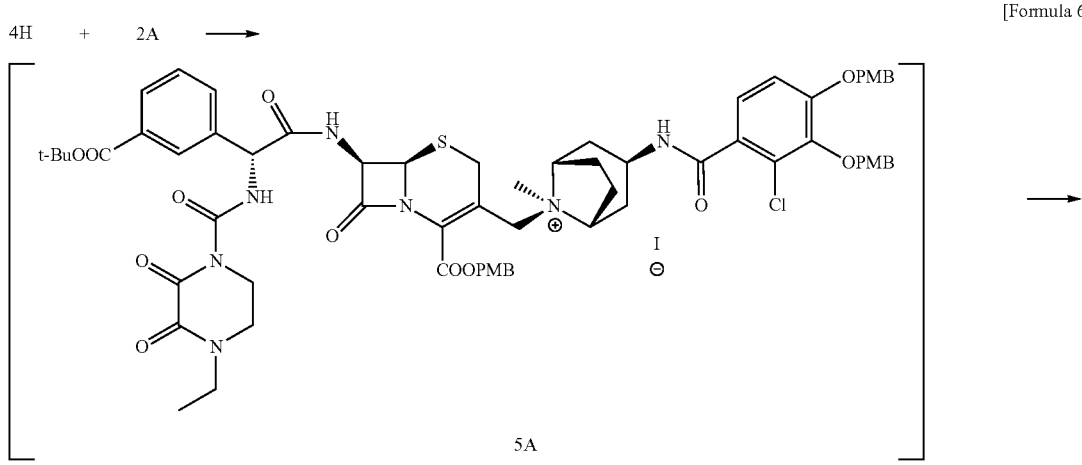

-continued

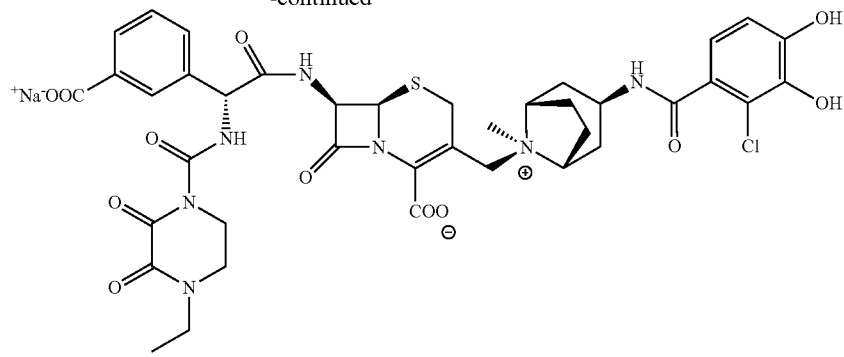

II-5

Step: Synthesis of Compound II-5

According to the similar manner as described in step 3 of Reference Example 1, compound II-5 (58 mg, yield 13%) was obtained as a white powder, from compound 4H (393 mg, 0.50 mmol) and compound 2A (276 mg, 0.50 mmol).

$^1$H-NMR (D$_2$O) δ: 1.19 (3H, t, J=7.1 Hz), 2.15 (2H, d, J=16.8 Hz), 2.36-2.47 (4H, m), 2.71-2.79 (2H, m), 3.04 (3H, s), 3.29 (1H, d, J=16.6 Hz), 3.51 (2H, q, J=7.1 Hz), 3.70-3.80 (3H, m), 3.89-4.05 (5H, m), 4.21 (1H, t, J=7.2 Hz), 4.56 (1H, d, J=14.1 Hz), 5.16 (1H, d, J=4.6 Hz), 5.55 (1H, s), 5.74 (1H, d, J=4.6 Hz), 6.86 (1H, d, J=8.4 Hz), 6.91 (1H, d, J=8.4 Hz), 7.52 (1H, t, J=7.6 Hz), 7.61 (1H, d, J=7.1 Hz), 7.89 (1H, d, J=7.6 Hz), 7.96 (1H, s).

MS (m+1)=868.47

Elemental analysis: C$_{39}$H$_{41}$ClN$_7$O$_{12}$SNa.8.3H$_2$O.0.4NaCl

Cal'd: C, 44.06; H, 5.46; Cl, 4.67; N, 9.22; S, 3.02; Na, 3.03(%).

Found: C, 44.10; H, 5.39; Cl, 4.38; N, 9.17; S, 2.98; Na, 3.06(%).

Reference Example 6

Synthesis of Compound II-6

[Formula 69]

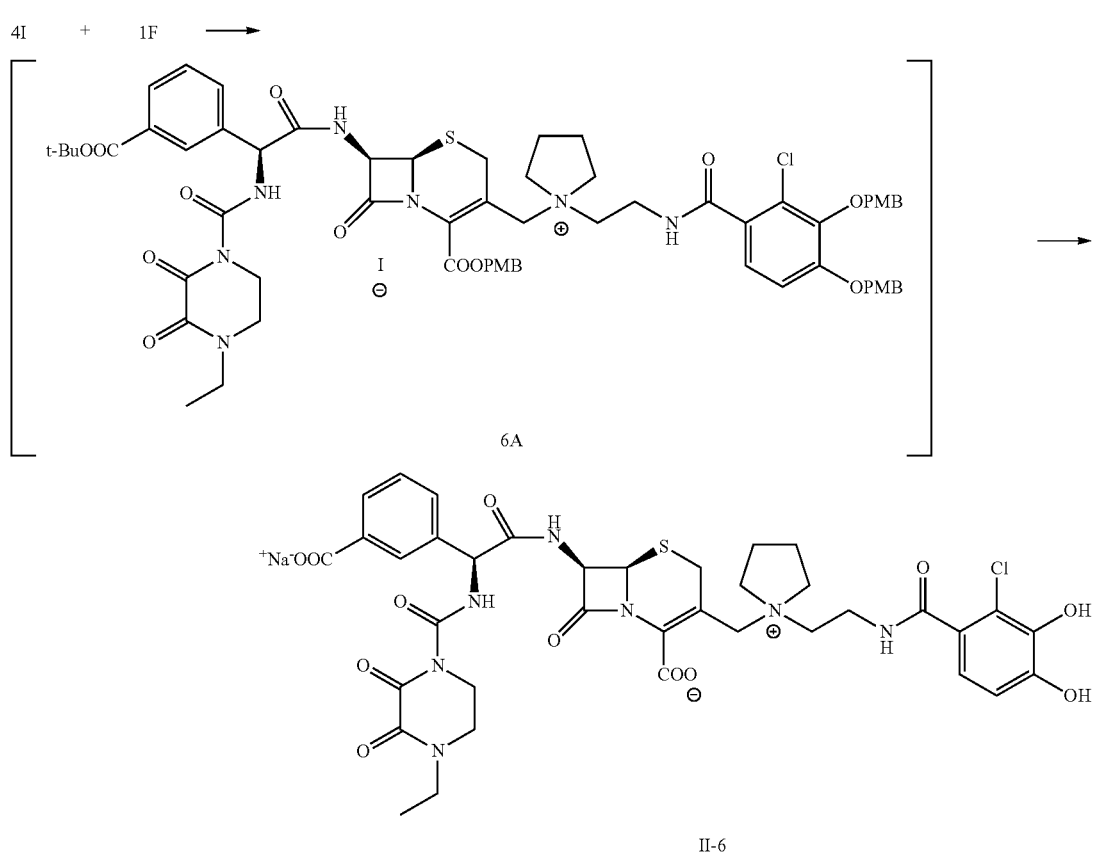

Step: Synthesis of Compound II-6

According to the similar manner as described in step 3 of Reference Example 1, compound II-6 (240 mg, yield 56%) was obtained as a white powder, from compound 4I (393 mg, 0.50 mmol) and compound 1F (263 mg, 0.50 mmol).

$^1$H-NMR (D$_2$O) δ: 1.17 (3H, t, J=7.2 Hz), 2.22 (4H, br s), 3.38-3.99 (17H, m), 4.17 (1H, d, J=13.9 Hz), 5.18 (1H, d, J=4.8 Hz), 5.44 (1H, d, J=4.8 Hz), 5.46 (1H, s), 6.83 (1H, d, J=8.4 Hz), 6.93 (1H, d, J=8.4 Hz), 7.45 (1H, t, J=7.7 Hz), 7.54 (1H, d, J=7.7 Hz), 7.85 (1H, d, J=7.7 Hz), 7.91 (1H, s).

MS (m+1)=842.49

Elemental analysis: C$_{37}$H$_{39}$ClN$_7$O$_{12}$SNa.7.8H$_2$O.0.2NaCl

Cal'd: C, 43.72; H, 5.41; N, 9.65; S, 3.15; Na, 2.71(%).
Found: C, 43.97; H, 5.38; N, 9.54; S, 2.85; Na, 2.70(%).

Reference Example 7

Synthesis of Compound II-7

Step: Synthesis of Compound II-7

According to the similar manner as described in step 3 of Reference Example 1, compound II-7 (32 mg, yield 11%) was obtained as a yellow powder, from compound 1D (300 mg, 0.39 mmol) and compound 7A (146 mg, 0.39 mmol).

$^1$H-NMR (D$_2$O) δ: 2.77 (3H, s), 2.90 (1H, d, J=17.2 Hz), 3.10 (1H, d, J=14.6 Hz), 3.69 (2H, br s), 4.00-4.13 (4H, m), 5.00 (1H, s), 5.15 (1H, d, J=18.6 Hz), 5.46-5.51 (2H, m), 5.68 (1H, d, J=3.7 Hz), 6.81 (1H, s), 7.35-7.47 (7H, m), 7.79 (1H, s).

MS (m+1)=719.37

Elemental analysis: C$_{33}$H$_{29}$N$_6$O$_{11}$SNa.5.9H$_2$O.0.8NaHCO$_3$

Cal'd: C, 44.41; H, 4.59; N, 9.19; S, 3.51; Na, 4.53(%).
Found: C, 44.39; H, 4.77; N, 9.26; S, 3.52; Na, 4.77(%).

[Formula 70]

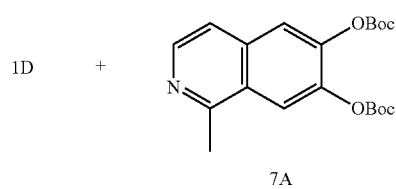

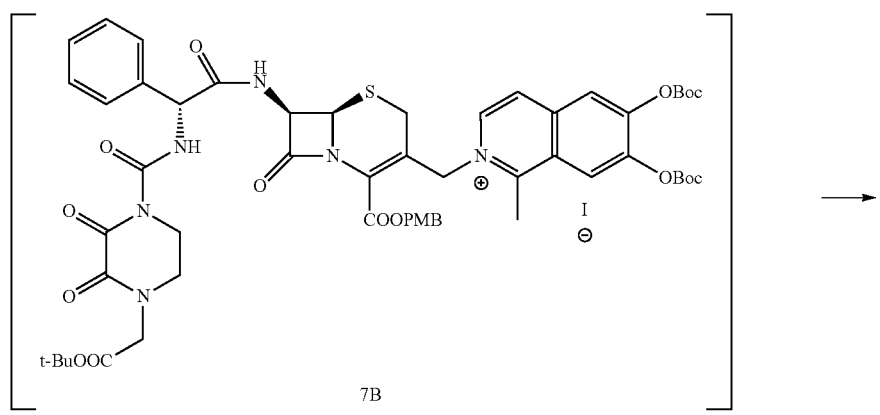

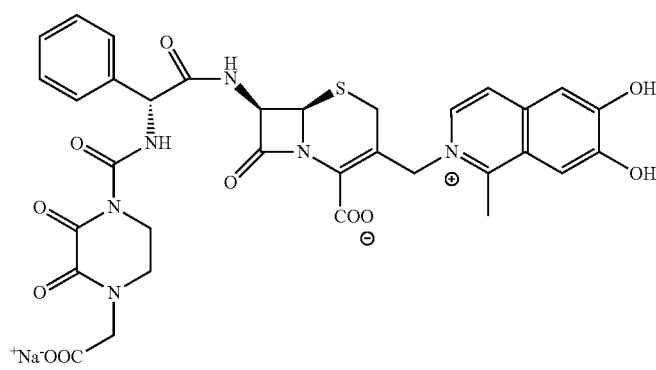

Reference Example 8
Synthesis of Compound II-8
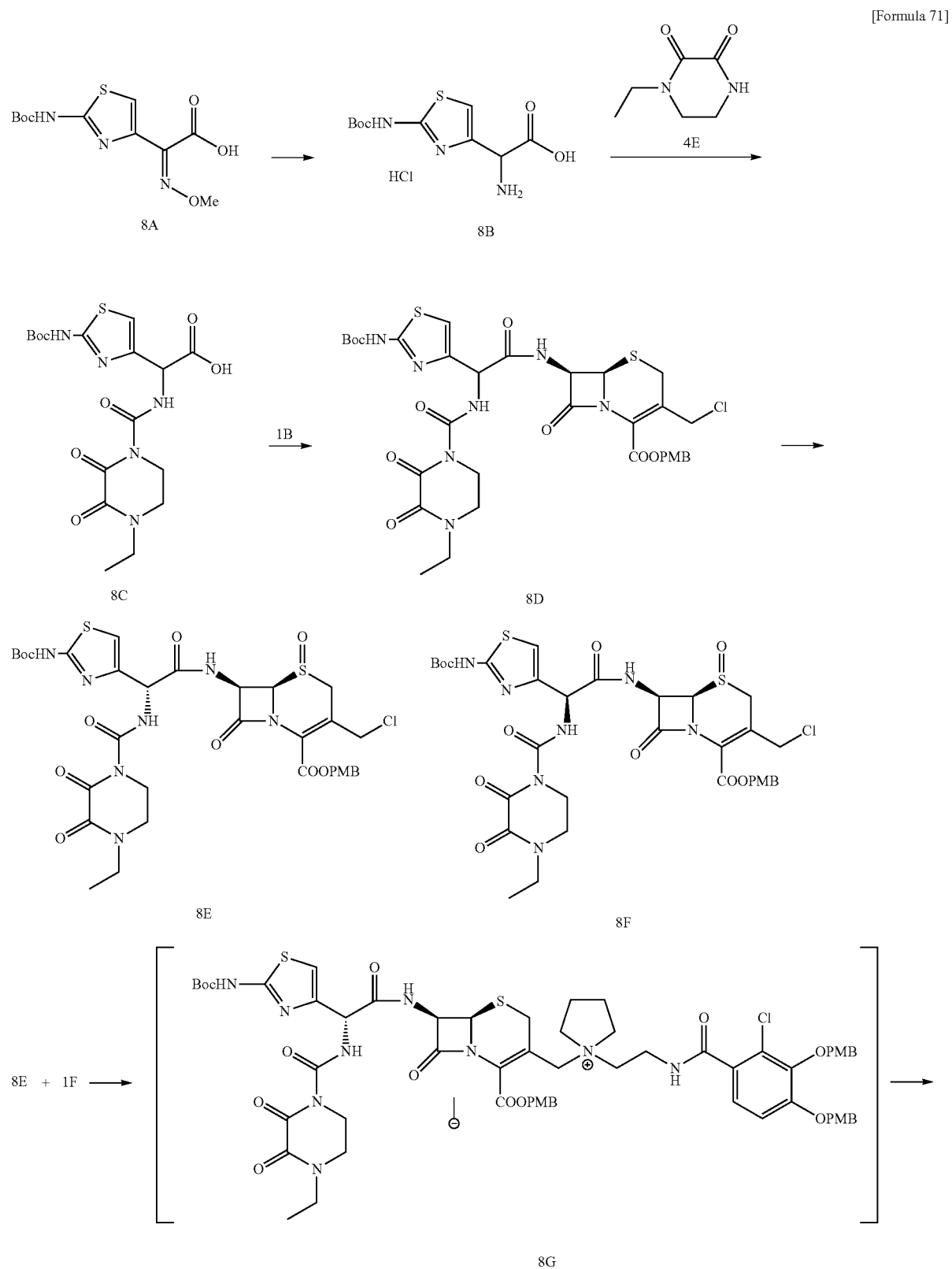

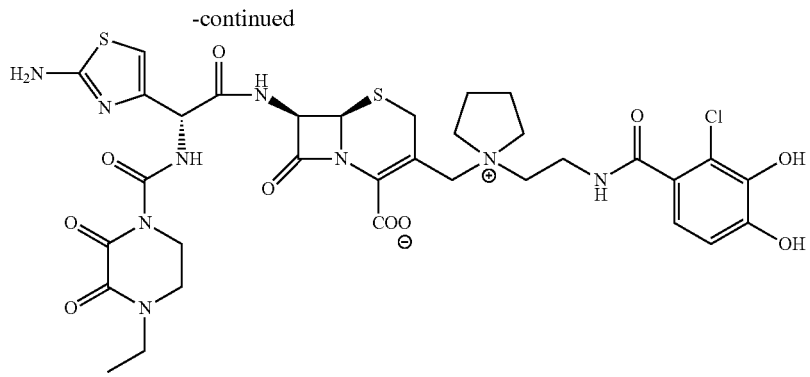

II-8

Step 1: Synthesis of Compound 8B

To a methanol (60 mL) solution of compound 8A (5.98 g, 19.9 mmol) were added 10% palladium/carbon (50% water-containing product) (4.22 g, 2.0 mmol) and 2 mol/L hydrochloric acid (11.9 mL, 23.8 mmol), and the mixture was stirred at room temperature for 4.5 hours under 1 atm hydrogen. After insolubles were removed by Celite-filtration, the solvent was distilled off under reduced pressure, and dried under reduced pressure to obtain compound 8B (6.06 g, yield 99%) as a white foam.

$^1$H-NMR (DMSO-$d_6$) δ: 1.48 (9H, s), 5.10 (1H, d, J=4.1 Hz), 7.36 (1H, s), 8.76 (2H, d, J=3.1 Hz), 11.62 (1H, s).

Step 2: Synthesis of Compound 8C

After a dichloromethane (20 mL) solution of compound 4E (909 mg, 6.4 mmol) was ice-cooled, triethylamine (1.22 mL, 8.8 mmol) and trimethylchlorosilane (899 μL, 7.0 mmol) were added, and the mixture was stirred at room temperature for 1 hour. After the reaction mixture was cooled to −30° C., triphosgene (721 mg, 2.4 mmol) was added, and the mixture was stirred at −30° C. for 1 hour. The solvent was distilled off under reduced pressure, and this was dried under reduced pressure to obtain the residue A as a pale orange solid.

After a dichloromethane (20 mL) suspension of compound 8B (2.72 g, 10.8 mmol) was ice-cooled, triethylamine (2.84 mL, 20.5 mmol) and trimethylchlorosilane (1.80 mL, 14.1 mmol) were added, and the mixture was stirred at room temperature for 2 hours. After the reaction mixture was cooled to −40° C., the residue A which had been obtained in the above-mentioned paragraph was dissolved in dichloromethane (20 mL), the mixture was stirred at −40° C. for 30 minutes and, thereafter, the mixture was further stirred for 1 hour under ice-cooling, and at room temperature for 1 hour. To the reaction mixture was added water, dichloromethane was distilled off under reduced pressure, and ethyl acetate was added. After pH was adjusted to 8.0 with an aqueous saturated sodium bicarbonate solution, the aqueous layer was separated. To the separated aqueous layer was added ethyl acetate, pH was adjusted to 2.0 with 1 mol/L hydrochloric acid, and this was extracted with ethyl acetate. The organic layer was sequentially washed with water and brine, and dried over anhydrous magnesium sulfate. The inorganic substances were removed by filtration, and the filtrate was concentrated under reduced pressure, and dried under reduced pressure to obtain compound 8C (3.92 g, yield 86%) as a yellow foam.

$^1$H-NMR (CDCl$_3$) δ: 1.20 (3H, t, J=7.2 Hz), 1.52 (9H, s), 3.46-3.68 (4H, m), 4.02-4.18 (2H, m), 5.64 (1H, d, J=6.8 Hz), 6.95 (1H, s), 9.93 (1H, d, J=6.8 Hz).

Step 3: Synthesis of Compound 8D

To a dichloromethane (16 mL) solution of compound 8C (1.57 g, 3.6 mmol) were added compound 1B (1.73 g, 4.3 mmol) and HOBt (529 mg, 3.9 mmol). After cooled to −20° C., N-methylmorpholine (469 μL, 4.3 mmol) and EDC hydrochloride (750 mg, 3.9 mmol) were added, and the mixture was stirred for 1 hour under ice-cooling. To the resulting reaction mixture was added 0.2 mol/L hydrochloric acid, dichloromethane was distilled off under reduced pressure, and this was extracted with ethyl acetate. The organic layer was sequentially washed with water, a 5% aqueous sodium bicarbonate solution and brine, and dried over anhydrous magnesium sulfate. The inorganic substances were removed by filtration, and the filtrate was concentrated under reduced pressure. The resulting crude product was purified by silica gel column chromatography (hexane-ethyl acetate) to obtain compound 8D (2.24 g, yield 79%) as a yellow foam.

$^1$H-NMR (CDCl$_3$) δ: 1.21 (3H, t, J=7.0 Hz), 1.55 (9H, s), 3.38-3.68 (5H, m), 3.80 (3H, d, J=1.8 Hz), 3.90-4.15 (2H, m), 4.36-4.56 (2H, m), 4.73-4.96 (2H, m), 5.19-5.23 (2H, m), 5.81-5.93 (1H, m), 6.85-6.90 (3H, m), 7.30-7.36 (2H, m), 9.90 (1H, s).

Step 4: Synthesis of Compounds 8E and 8F

According to the similar manner as described in step 2 of Reference Example 1, compound 8E (887 mg, yield 39%) as a yellow foam, and compound 8F (1.01 g, yield 44%) as a yellow foam were obtained, from compound 8D (2.24 g, 2.8 mmol).

8e: $^1$H-NMR (CDCl$_3$) δ: 1.21 (3H, t, J=7.5 Hz), 1.53 (9H, s), 3.47-3.63 (5H, m), 3.77 (1H, d, J=13.7 Hz), 3.80 (3H, s), 3.98-4.19 (2H, m), 4.31 (1H, d, J=12.2 Hz), 4.62 (1H, d, J=3.8 Hz), 4.83 (1H, d, J=12.0 Hz), 5.26 (2H, s), 5.65 (1H, d, J=6.6 Hz), 6.09 (1H, dd, J=10.1, 4.9 Hz), 6.81 (1H, s), 6.89 (2H, d, J=8.5 Hz), 7.35 (2H, d, J=8.5 Hz), 8.44 (1H, d, J=9.8 Hz), 8.75 (1H, s), 9.91 (1H, d, J=6.4 Hz).

8f: $^1$H-NMR (CDCl$_3$) δ: 1.22 (3H, t, J=7.1 Hz), 1.53 (9H, s), 3.46-3.58 (5H, m), 3.80 (3H, s), 3.81 (1H, d, J=17.8 Hz), 4.00-4.15 (2H, m), 4.32 (1H, d, J=12.2 Hz), 4.71 (1H, d, J=4.1 Hz), 4.86 (1H, d, J=12.2 Hz), 5.23 (2H, s), 5.73 (1H, d, J=7.0 Hz), 6.00 (1H, dd, J=9.7, 4.8 Hz), 6.79 (1H, s), 6.88 (2H, d, J=8.5 Hz), 7.33 (2H, d, J=8.5 Hz), 8.17 (1H, d, J=9.0 Hz), 9.25 (1H, s), 9.88 (1H, d, J=4.7 Hz).

Step 5: Synthesis of Compound II-8

After a DMA (1 mL) solution of compound 1F (263 mg, 0.50 mmol) was cooled to 15° C., compound 8E (404 mg, 0.50 mmol) was added, and the mixture was degassed under reduced pressure. Sodium iodide (150 mg, 1.0 mmol) was added, and the mixture was stirred at 15° C. for 6 hours. After DMF (3.0 mL) was added, the mixture was cooled to −40° C., phosphorus tribromide (94 μL, 1.0 mmol) was added, and the mixture was stirred at −40° C. for 30 minutes. The reaction mixture was slowly added to an ice-cooled 5% aqueous sodium chloride solution. The precipitated solid was filtered, washed with water, suspended in water, and lyophilized to obtain compound 8G as a brown solid. The resulting compound 8G was used in the next reaction without purification.

After the total amount of the resulting compound 8G was dissolved in dichloromethane (6 ml), and the solution was cooled to −40° C., anisole (546 μL, 5.0 mmol) and a 2 mol/L-aluminum chloride/nitromethane solution (2.5 mL, 5.0 mmol) were sequentially added, and the mixture was stirred at 0° C. for 30 minutes. To the reaction solution were added diisopropyl ether, and a small amount of water, the mixture was stirred to generate the precipitate, and the supernatant was removed by decantation. To the insolubles which had been left in a container were added dilute hydrochloric acid and acetonitrile, the mixture was stirred to completely dissolve the materials, diisopropyl ether was added, and the aqueous layer was separated. After the organic layer was extracted again with water, all aqueous layers were combined, the HP20-SS resin was added, and acetonitrile was distilled off under reduced pressure, the resulting mixed solution was purified by ODS column chromatography (water-acetonitrile). The fractions containing the desired compound were collected, and this was concentrated under reduced pressure, and lyophilized to obtain compound II-8 (192 mg, yield 47%) as a white powder.

$^1$H-NMR (DMSO-$d_6$) δ: 1.08 (3H, t, J=7.1 Hz), 1.98-2.12 (4H, m), 3.38-3.58 (11H, m), 3.72-3.93 (6H, m), 5.01-5.09 (2H, m), 5.43 (1H, d, J=7.5 Hz), 5.60 (1H, dd, J=8.6, 5.1 Hz), 6.53 (1H, s), 6.77 (2H, s), 7.03 (2H, s), 8.41 (1H, t, J=5.5 Hz), 9.01 (1H, d, J=8.6 Hz), 9.33 (1H, s), 9.64 (1H, d, J=7.5 Hz), 10.29 (1H, s).

MS (m+1)=820.39

Elemental analysis: $C_{33}H_{38}ClN_9O_{10}S_2 \cdot 4.9H_2O$

Cal'd: C, 43.62; H, 5.30; Cl, 3.90; N, 13.87; S, 7.06(%).

Found: C, 43.64; H, 5.14; Cl, 4.04; N, 13.66; S, 7.07(%).

Reference Example 9

Synthesis of Compound II-9

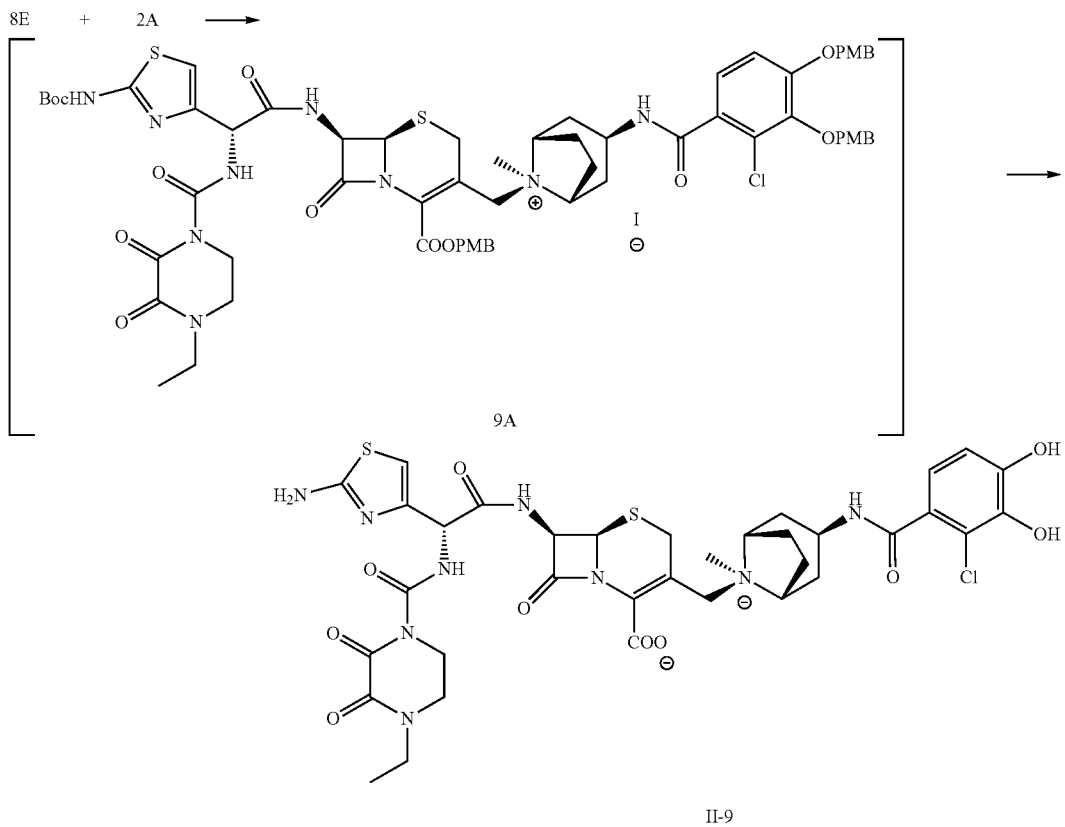

[Formula 72]

Step 1: Synthesis of Compound II-9

According to the similar manner as described in step 5 of Reference Example 8, compound II-9 (183 mg, yield 43%) was obtained as a white powder, from compound 8E (404 mg, 0.50 mmol) and compound 2A (276 mg, 0.50 mmol).

$^1$H-NMR (DMSO-$d_6$) δ: 1.08 (3H, t, J=7.2 Hz), 1.91-1.99 (2H, m), 2.30-2.53 (6H, br m), 2.96 (3H, s), 3.56 (4H, t, J=5.6 Hz), 3.72-4.00 (8H, m), 4.86 (1H, d, J=12.8 Hz), 5.01 (1H, d, J=5.1 Hz), 5.44 (1H, d, J=7.4 Hz), 5.59 (1H, dd, J=8.4, 5.1 Hz), 6.53 (1H, s), 6.70 (1H, d, J=8.2 Hz), 6.77 (1H, d, J=8.2 Hz), 7.04 (2H, s), 8.32 (1H, d, J=3.2 Hz), 9.00 (1H, d, J=9.0 Hz), 9.64 (1H, d, J=7.4 Hz).

MS (m+1)=864.49

Elemental analysis: $C_{35}H_{40}ClN_9O_{10}S_2 \cdot 5.6H_2O$

Cal'd: C, 44.38; H, 5.45; Cl, 3.74; N, 13.31; S, 6.77(%).

Found: C, 44.36; H, 5.37; Cl, 3.65; N, 13.36; S, 6.72(%).

Reference Example 10

Synthesis of Compound II-10

[Formula 73]

8F + 1F →

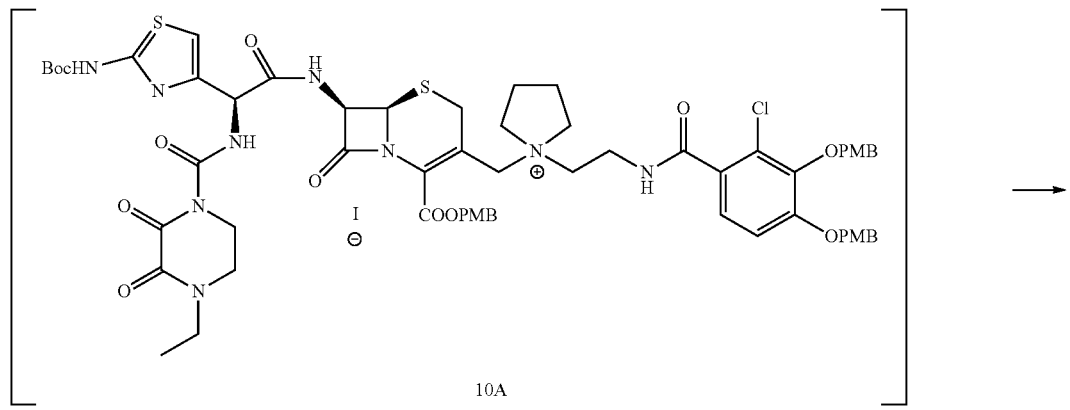

10A

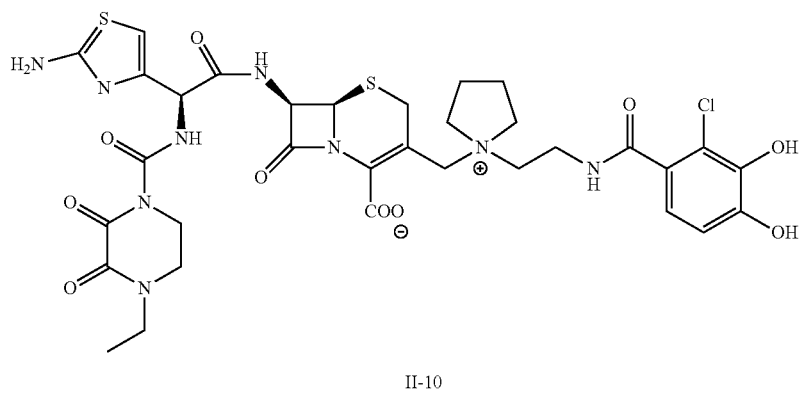

II-10

Step: Synthesis of Compound II-10

According to the similar manner as described in step 5 of Reference Example 8, compound II-10 (163 mg, yield 40%) was obtained as a white powder, from compound 8F (404 mg, 0.50 mmol) and compound 1F (263 mg, 0.50 mmol).

$^1$H-NMR (DMSO-$d_6$) δ: 1.08 (3H, t, J=7.0 Hz), 1.99-2.13 (4H, m), 3.40-3.56 (10H, m), 3.78-3.93 (6H, m), 5.05-5.09 (2H, m), 5.39 (1H, d, J=7.6 Hz), 5.48 (1H, dd, J=7.7, 5.1 Hz), 6.50 (1H, s), 6.77 (2H, s), 7.07 (2H, s), 8.41 (1H, s), 9.17 (1H, d, J=7.7 Hz), 9.63 (1H, d, J=7.6 Hz).

MS (m+1)=820.51

Elemental analysis: $C_{33}H_{38}ClN_9O_{10}S_2 \cdot 4.6H_2O$

Cal'd: C, 43.89; H, 5.27; Cl, 3.93; S, 7.10(%).

Found: C, 43.86; H, 5.20; Cl, 3.94; S, 7.03(%).

Reference Example 11

Synthesis of Compound II-11

[Formula 74]

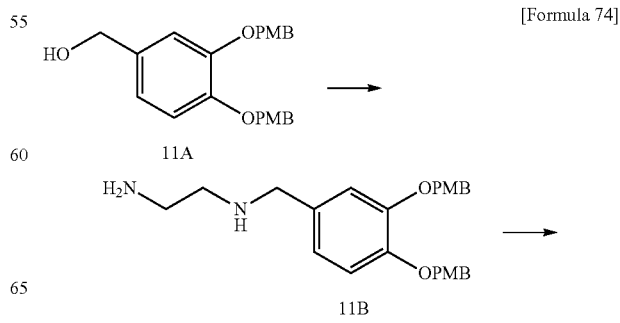

11A

11B

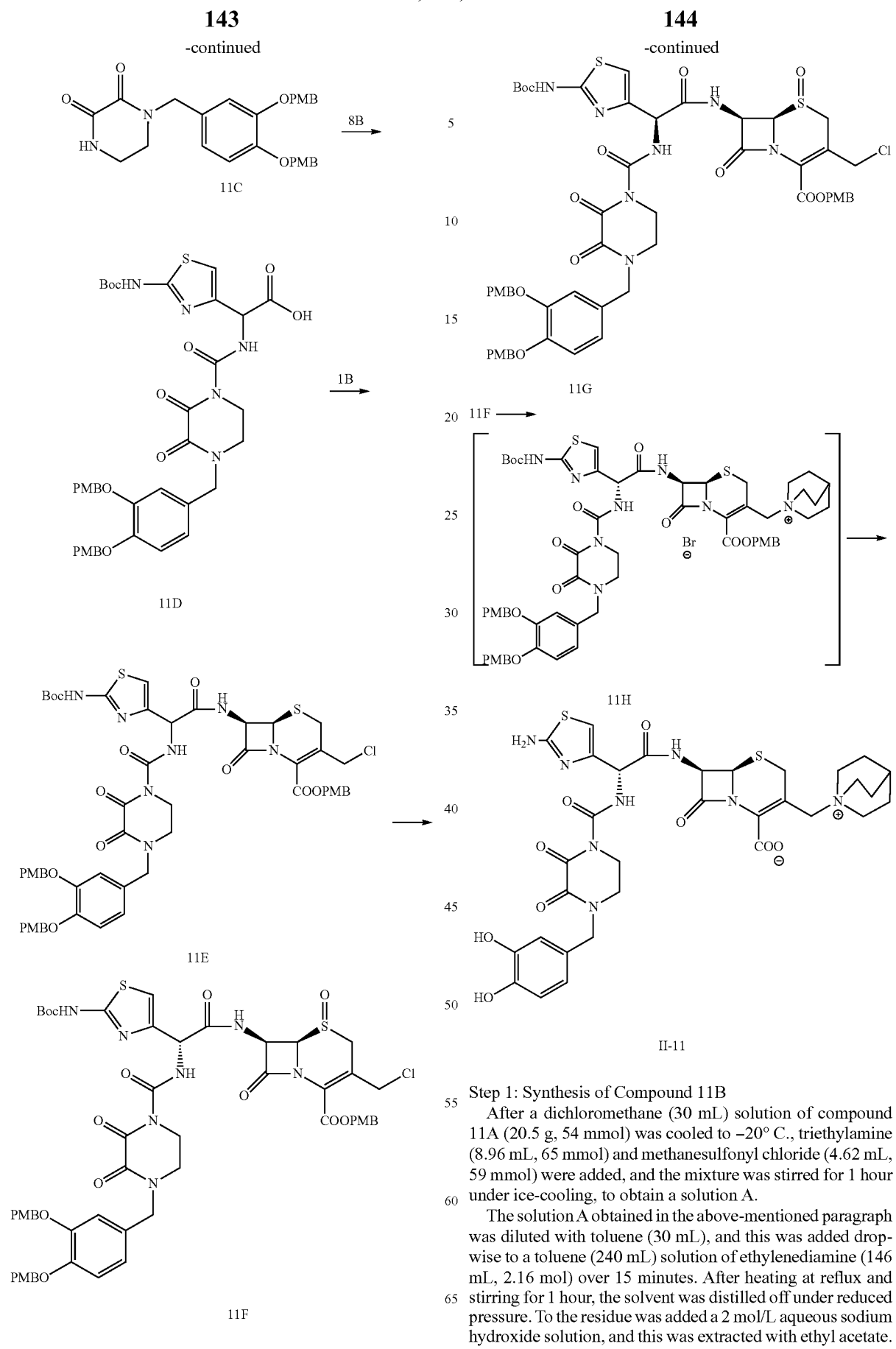

Step 1: Synthesis of Compound 11B

After a dichloromethane (30 mL) solution of compound 11A (20.5 g, 54 mmol) was cooled to −20° C., triethylamine (8.96 mL, 65 mmol) and methanesulfonyl chloride (4.62 mL, 59 mmol) were added, and the mixture was stirred for 1 hour under ice-cooling, to obtain a solution A.

The solution A obtained in the above-mentioned paragraph was diluted with toluene (30 mL), and this was added dropwise to a toluene (240 mL) solution of ethylenediamine (146 mL, 2.16 mol) over 15 minutes. After heating at reflux and stirring for 1 hour, the solvent was distilled off under reduced pressure. To the residue was added a 2 mol/L aqueous sodium hydroxide solution, and this was extracted with ethyl acetate.

The organic layer was washed with water, this was extracted with 1 mol/L hydrochloric acid, and the aqueous layer was separated. To the aqueous layer was added again a 2 mol/L aqueous sodium hydroxide solution to make the solution basic and, thereafter, this was extracted with ethyl acetate. The organic layer was sequentially washed with water and brine, and dried over anhydrous sodium sulfate. The inorganic substances were removed by filtration, and the filtrate was concentrated under reduced pressure. The resulting crude product was purified by basic silica gel column chromatography (chloroform-methanol) to obtain compound 11B (16.4 g, yield 72%) as a brown oil.

$^1$H-NMR (CDCl$_3$) δ: 2.56-2.65 (2H, m), 2.78 (1H, t, J=5.9 Hz), 3.06 (1H, t, J=7.0 Hz), 3.54 (1H, s), 3.68 (1H, s), 3.80 (6H, s), 5.04 (2H, s), 5.06 (2H, s), 6.78-6.88 (6H, m), 6.94 (1H, dd, J=4.2, 1.8 Hz), 7.33 (4H, d, J=8.1 Hz).

Step 2: Synthesis of Compound 11C

To an ethanol (160 mL) solution of compound 11B (16.3 g, 39 mmol) was added diethyl oxalate (15.8 mL, 116 mmol), and the mixture was heat-refluxed under stirring for 6 hours. The solvent was distilled off under reduced pressure, and the resulting residue was purified by silica gel column chromatography (ethyl acetate-methanol) to obtain compound 11C (5.48 g, yield 30%) as a white solid.

$^1$H-NMR (CDCl$_3$) δ: 3.27 (2H, s), 3.27 (2H, s), 3.80 (3H, s), 3.81 (3H, s), 4.54 (2H, s), 5.06 (2H, s), 5.08 (2H, s), 6.45 (1H, s), 6.73 (1H, dd, J=8.2, 1.9 Hz), 6.82-6.90 (5H, m), 7.33 (4H, t, J=8.2 Hz).

Step 3: Synthesis of Compound 11D

According to the similar manner as described in step 2 of Reference Example 8, compound 11D (4.71 g, yield 53%) was obtained as a yellow foam, from compound 11C (5.48 g, 11.5 mmol) and compound 8B (3.56 g, 11.5 mmol).

$^1$H-NMR (CDCl$_3$) δ: 1.50 (9H, s), 3.21-3.33 (2H, m), 3.71 (3H, s), 3.75-3.87 (2H, m), 3.79 (3H, s), 4.37-4.62 (2H, m), 5.02 (4H, s), 5.64 (1H, d, J=6.8 Hz), 6.69-6.95 (8H, m), 7.26 (2H, d, J=8.5 Hz), 7.32 (2H, d, J=8.5 Hz), 9.94 (1H, d, J=6.8 Hz).

Step 4: Synthesis of Compound 11E

According to the similar manner as described in step 3 of Reference Example 8, compound 11E (4.91 g, yield 72%) was obtained as a yellow foam, from compound 11D (4.70 g, 6.1 mmol) and compound 1B (2.95 g, 7.3 mmol).

MS (m+1)=1127.02

Step 5: Synthesis of Compound 11F and Compound 11G

According to the similar manner as described in step 2 of Reference Example 1, compound 11F (1.77 g, yield 36%) as a yellow foam, and compound 11G (2.24 g, yield 45%) as a yellow foam were obtained, from compound 11E (4.90 g, 4.35 mmol).

Compound 11F: $^1$H-NMR (CDCl$_3$) δ: 1.64 (9H, s), 3.23-3.33 (2H, m), 3.45 (1H, d, J=19.5 Hz), 3.67-3.75 (2H, m), 3.75 (3H, s), 3.81 (3H, s), 3.81 (3H, s), 3.90-3.95 (1H, m), 4.28 (1H, d, J=12.5 Hz), 4.43 (1H, d, J=14.0 Hz), 4.53 (1H, d, J=4.1 Hz), 4.62 (1H, d, J=14.6 Hz), 4.92 (1H, d, J=12.5 Hz), 5.06 (4H, s), 5.26 (2H, s), 5.62 (1H, d, J=6.7 Hz), 6.07 (1H, dd, J=10.1, 4.8 Hz), 6.73-6.91 (10H, m), 7.31 (2H, d, J=8.5 Hz), 7.35 (4H, d, J=8.8 Hz), 8.47 (1H, d, J=10.1 Hz), 8.62 (1H, s), 9.95 (1H, d, J=6.7 Hz).

Compound 11G: $^1$H-NMR (CDCl$_3$) δ: 1.53 (9H, s), 3.32 (2H, s), 3.44 (1H, d, J=18.4 Hz), 3.73-3.81 (3H, m), 3.74 (3H, s), 3.79 (3H, s), 3.80 (3H, s), 4.30 (1H, d, J=12.4 Hz), 4.54 (2H, s), 4.67 (1H, s), 4.86 (1H, d, J=11.3 Hz), 5.05 (4H, s), 5.23 (2H, s), 5.76 (1H, s), 6.01 (1H, dd, J=9.8, 4.8 Hz), 6.74-6.90 (10H, m), 7.32 (6H, t, J=8.5 Hz), 8.14 (1H, s), 9.27 (1H, s), 9.91 (1H, s).

Step 6: Synthesis of Compound II-11

After a DMA (1 mL) solution of quinuclidine (55.6 mg, 0.50 mmol) was cooled to 15° C., compound 11F (571 mg, 0.50 mmol) was added, and the mixture was degassed under reduced pressure. Sodium bromide (103 mg, 1.0 mmol) was added, and the mixture was stirred at 15° C. for 3 hours. After DMF (3.0 mL) was added, the mixture was cooled to −40° C., phosphorus tribromide (94 μL, 1.0 mmol) was added, and the mixture was stirred at −40° C. for 30 minutes. The reaction mixture was slowly added to an ice-cooled 5% aqueous sodium chloride solution. The precipitated solid was filtered, washed with water, suspended in water, and lyophilized to obtain compound 11H as a brown solid. The resulting compound 11H was used in the next reaction without purification.

The total amount of the resulting compound 11H was dissolved in dichloromethane (6 ml), the solution was cooled to −40° C., thereafter, anisole (546 μL, 5.0 mmol) and a 2 mol/L-aluminum chloride/nitromethane solution (2.5 mL, 5.0 mmol) were sequentially added, and the mixture was stirred at 0° C. for 30 minutes. To the reaction solution were added diisopropyl ether, and a small amount of water, the mixture was stirred to generate the precipitate, and the supernatant was removed by decantation. To the insolubles which had been left in a container were added dilute hydrochloric acid and acetonitrile, the mixture was stirred to completely dissolve the materials, diisopropyl ether was added, and the aqueous layer was separated. The organic layer was extracted again with water, all aqueous layers were combined, the HP20-SS resin was added, and acetonitrile was distilled off under reduced pressure. The resulting mixed solution was purified by ODS column chromatography (water-acetonitrile). The fractions containing the desired compound were collected, and this was concentrated under reduced pressure, and lyophilized to obtain compound II-11 (168 mg, yield 45%) as a white powder.

$^1$H-NMR (DMSO-d$_6$) δ: 1.82 (6H, s), 2.02 (1H, s), 3.13-3.34 (9H, m), 3.71 (2H, d, J=16.5 Hz), 3.89 (2H, d, J=2.7 Hz), 4.41 (2H, s), 4.84 (1H, d, J=12.8 Hz), 5.00 (1H, d, J=5.0 Hz), 5.43 (1H, d, J=7.5 Hz), 5.58 (1H, dd, J=8.7, 5.0 Hz), 6.53-6.57 (2H, m), 6.67-6.69 (2H, m), 7.04 (2H, s), 8.99 (1H, d, J=8.7 Hz), 9.04 (2H, s), 9.63 (1H, d, J=7.5 Hz).

MS (m+1)=741.50

Elemental analysis: C$_{32}$H$_{36}$N$_8$O$_9$S2.5.8H$_2$O

Cal'd: C, 45.47; H, 5.68; N, 13.26; S, 7.59(%).

Found: C, 45.50; H, 5.64; N, 13.24; S, 7.54(%).

Reference Example 12

Synthesis of Compound II-12

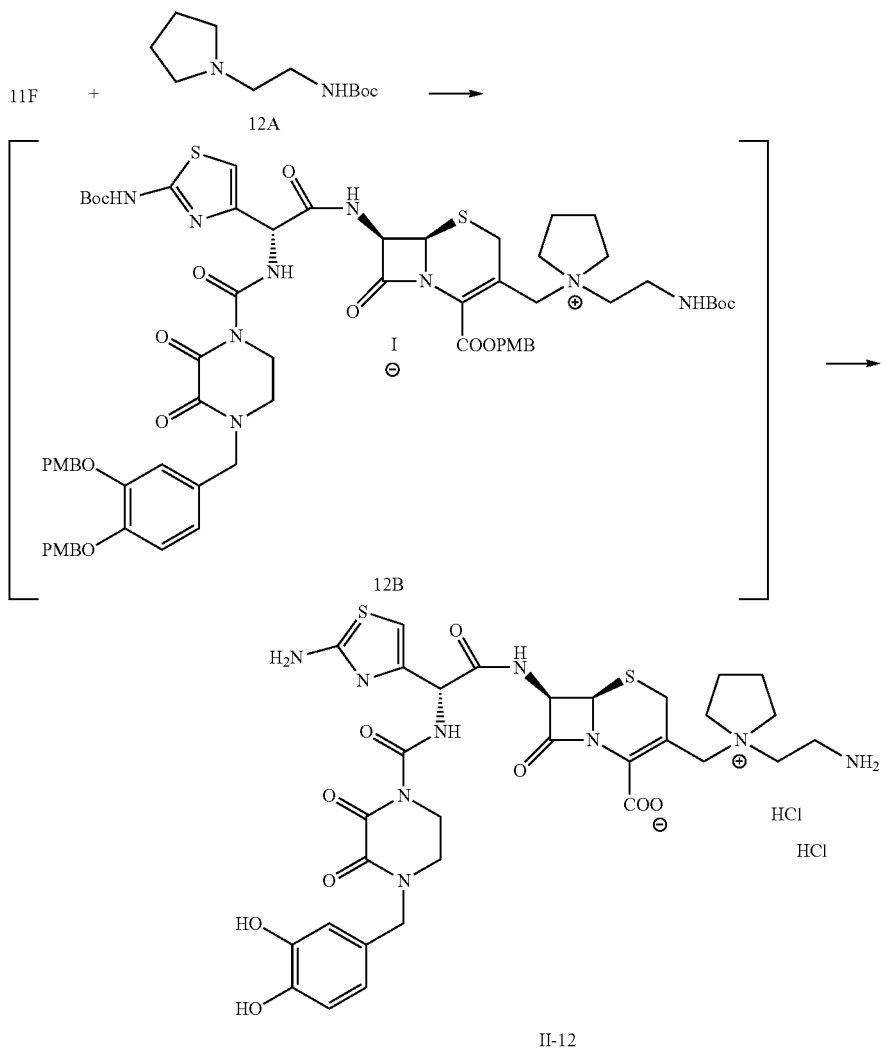

[Formula 75]

Step: Synthesis of Compound II-12

After a DMA (1 mL) solution of compound 12A (107 mg, 0.50 mmol) was cooled to 15° C., compound 11F (571 mg, 0.50 mmol) was added, and the mixture was degassed under reduced pressure. Sodium iodide (150 mg, 1.0 mmol) was added, and the mixture was stirred at 15° C. for 6 hours. After DMF (3.0 mL) was added, the mixture was cooled to −40° C., phosphorus tribromide (94 µL, 1.0 mmol) was added, and the mixture was stirred at −40° C. for 30 minutes. The reaction mixture was slowly added to an ice-cooled 5% aqueous sodium chloride solution. The precipitated solid was filtered, washed with water, suspended in water, and lyophilized to obtain compound 12B as a brown solid. The resulting compound 12B was used in the next reaction without purification.

After the total amount of the resulting compound 12B was dissolved in dichloromethane (6 ml), and the solution was cooled to −40° C., anisole (546 µL, 5.0 mmol) and a 2 mol/L-aluminum chloride/nitromethane solution (2.5 mL, 5.0 mmol) were sequentially added, and the mixture was stirred at 0° C. for 30 minutes. To the reaction solution were added diisopropyl ether, and a small amount of water, the mixture was stirred to generate the precipitate, and the supernatant was removed by decantation. To the insolubles which had been left in a container were added dilute hydrochloric acid and acetonitrile, the mixture was stirred to completely dissolve the materials, thereafter, diisopropyl ether was added, and the aqueous layer was separated. The organic layer was extracted again with water, all aqueous layer were combined, the HP20-SS resin was added, and acetonitrile was distilled off under reduced pressure. The resulting mixed solution was purified by ODS column chromatography (1 mmol/L hydrochloric acid-acetonitrile). The fractions containing the desired compound were collected, and this was concentrated under reduced pressure, and lyophilized to obtain compound II-12 (96 mg, yield 24%) as a white powder. $^1$H-NMR (D$_2$O) δ: 2.23 (4H, br s), 3.39-3.62 (12H, m), 3.87 (1H, d, J=16.8 Hz), 3.98 (2H, dd, J=10.4, 5.2 Hz), 4.06 (1H, d, J=14.1 Hz), 4.56 (2H, d, J=3.3 Hz), 5.28 (1H, d, J=4.7 Hz), 5.63 (1H, s), 5.73 (1H, d, J=4.7 Hz), 6.78-6.95 (4H, m).

MS (m+1)=744.54

Elemental analysis: C$_{31}$H$_{37}$N$_9$O$_9$S2.2.6HCl.7.1H$_2$O
Cal'd: C, 38.52; H, 5.61; Cl, 9.54; N, 13.04; S, 6.64(%).
Found: C, 38.53; H, 5.47; Cl, 9.60; N, 13.05; S, 6.62(%).

Test Example 1

The in vitro antimicrobial activity of compound (I) of the subject invention was confirmed.
(Test Method)

Measurement of a minimum growth inhibition concentration (MIC: µg/mL) was performed according to CLSI (Clinical and Laboratory Standards Institute) method, by broth microdilution method, using an inoculation microbe amount of 10000 cfu/well and cation-adjusted Mueller Hinton broth containing human-derived 20 µM apo-transferrin as a test medium.

TABLE 1

|  | Example compound No. | | | | | | |
| --- | --- | --- | --- | --- | --- | --- | --- |
|  | I-1 | I-2 | I-3 | I-5 | I-6 | I-7 | I-8 |
| E. coli ATCC BAA-196_TEM-10 | 0.25 | 0.25 | 1. | 8. | 0.25 | 0.125 | 0.5 |
| K. pneumoniae ATCC 700603_SHV18 | 2. | 4. |  |  | 0.125 | 0.063 | 1. |
| P. aeruginosa SR24 | 0.125 | 0.125 | 0.25 |  | 0.125 | 0.125 | 0.125 |
| P. aeruginosa SR27060(metallo) | 0.25 | 0.125 | 1. |  | 0.25 | 0.125 | 4. |
| S. maltophilia SR21970(L-1) |  |  |  |  |  |  |  |
| A. baumannii SR24396 | ≤0.031 | 0.063 | 0.125 | ≤0.031 | ≤0.031 | ≤0.031 | 0.063 |
| P. aeruginosa SR27001(MDRP, IMP-1+) | 0.5 | 0.25 | 4. |  | 0.25 | 0.5 | 8. |

TABLE 2

|  | Example compound No. | | | | | Comparative Example compound 1 | Comparative Example compound 2 |
| --- | --- | --- | --- | --- | --- | --- | --- |
|  | I-9 | I-13 | I-20 | I-22 | I-23 | | |
| E. coli ATCC BAA-196_TEM-10 | 0.5 | 1. | 2. | 1. | 1. | 16. | 32. |
| K. pneumoniae ATCC 700603_SHV18 | 0.125 | 0.5 |  | 8. | 8. | 16. | 16. |
| P. aeruginosa SR24 | 0.125 | 0.125 |  | 0.125 | 0.125 | 8. | 8. |
| P. aeruginosa SR27060(metallo) | 1. | 2. | 4. | 2. | 0.5 | >32 | >32 |
| S. maltophilia SR21970(L-1) | 1. | >32 |  | 32. | 8. | >32 | >32 |
| A. baumannii SR24396 | 0.063 | 0.063 |  | 0.5 | 0.25 | 4. | 16. |
| P. aeruginosa SR27001(MDRP, IMP-1+) | 2. | 2. |  |  | >32 | >32 | >32 |

TABLE 3

|  | Example compound No. | | | | | | |
| --- | --- | --- | --- | --- | --- | --- | --- |
|  | I-4 | I-10 | I-11 | I-12 | I-14 | I-15 | I-16 |
| E. coli ATCC BAA-196_TEM-10 | 0.5 | 1. | 1. | 2. | 0.5 | 1. | 0.125 |
| K. pneumoniae ATCC 700603_SHV18 |  | 0.5 | 4. | 1. | 1. | 1. | 1. |
| P. aeruginosa SR24 | 0.125 | 0.25 | 0.25 | 0.25 | 0.5 | 0.25 | 0.25 |
| P. aeruginosa SR27001 (MDRP, IMP-1+) |  | 2. | 4. | 4. |  | 4. | 2. |

TABLE 4

|  | Example compound No. | | | | | |
| --- | --- | --- | --- | --- | --- | --- |
|  | I-17 | I-18 | I-19 | I-24 | I-25 | I-26 |
| E. coli ATCC BAA-196_TEM-10 | 4 |  | 8 | 1 | 2 | 1 |
| K. pneumoniae ATCC 700603_SHV18 | 8 |  |  | 0.5 | 1 | 1 |
| P. aeruginosa SR24 | 0.25 | 0.5 | 0.5 | 0.5 | 0.5 | 1 |
| P. aeruginosa SR27001(MDRP, IMP-1+) |  |  |  | 16 | 4 | 4 |

TABLE 5

|  | Example compound No. | | | | | |
| --- | --- | --- | --- | --- | --- | --- |
|  | I-27 | I-28 | I-29 | I-30 | I-31 | I-32 |
| E. coli ATCC BAA-196_TEM-10 | 2 | 0.5 | 0.5 | 0.5 | 0.25 | 0.5 |
| K. pneumoniae ATCC 700603_SHV18 | 0.5 | 1 | 1 | 2 | 0.25 | 1 |
| P. aeruginosa SR24 | 0.25 | 0.25 | 0.5 | 0.25 | 0.5 | 0.25 |
| P. aeruginosa SR27001(MDRP, IMP-1+) | 4 | 8 | 2 | 8 | 1 | 2 |

The species, the enzyme produced by the strain (beta-lactamase) and the strain type of the bacteria in the above Tables are listed in Table 6.

TABLE 6

| Species | Strain name | Produced enzyme | Strain Type |
| --- | --- | --- | --- |
| E. coli | ATCC BAA-196 | TEM-10 | ESBL producing strain |
| K. pneumoniae | ATCC700603 | SHV-18 | ESBL producing strain |
| P. aeruginosa | SR24 | None | Ceftazidime-sensitive strain |
| P. aeruginosa | SR27060 | IMP-1 | MBL producing strain (carbapenem-resistant strain) |

TABLE 6-continued

| Species | Strain name | Produced enzyme | Strain Type |
|---|---|---|---|
| S. maltophilia | SR21970 | L-1 | MBL producing strain (carbapenem-resistant strain) |
| A. baumannii | SR24396 | None | |
| P. aeruginosa | SR27001 | IMP-1 | MBL producing strain (carbapenem-resistant strain) |

Structural formulae of Comparative Compounds are shown below.

[Formula 76]

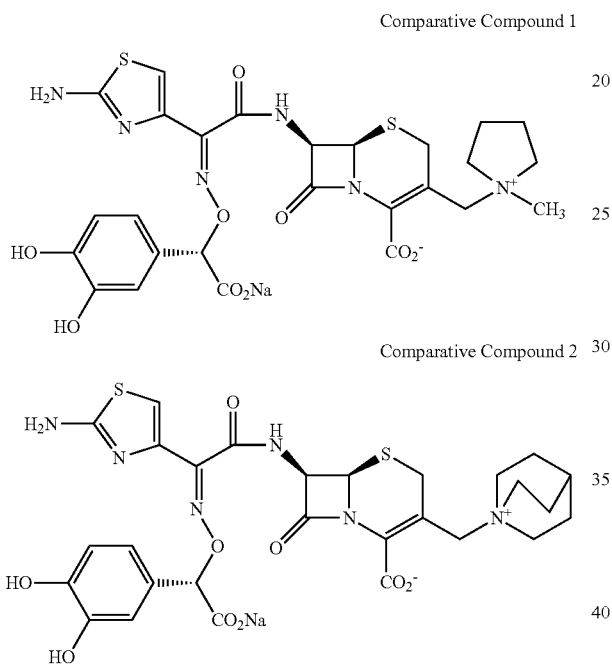

Comparative Compound 1

Comparative Compound 2

From the foregoing results, it was shown that the compound of the subject invention has a wide range of antimicrobial spectrum, exhibits strong antimicrobial spectrum, particularly, against Gram negative bacteria, and/or is also effective against multiple-drug-resistant microbes, and also has high stability against beta-lactamase producing Gram negative bacteria. In addition, the compound of the subject invention exhibited high antimicrobial activity, compared with Comparative Compounds 1 and 2 having similar structures. Thus, it was shown that the compound of the subject invention is useful as a pharmaceutical product.

Formulation Example 1

Injectables are prepared by powderizing and filling the compound of the subject invention.

INDUSTRIAL APPLICABILITY

The compound in connection with the subject invention has a wide range of antimicrobial spectrum, and is also effective as an antimicrobial drug having high stability against beta-lactamase producing Gram negative bacteria. In addition, since the compound of the subject invention has good disposition, and also has high water-solubility, and thus particularly effective as an injection drug.

The invention claimed is:

1. A compound of formula (I):

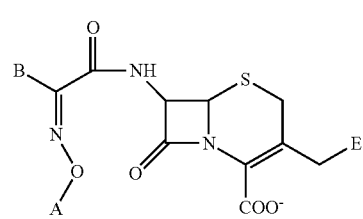

(I)

wherein,

A is a group of any one of the following formula (ia), (ib), (iia) and (iii):

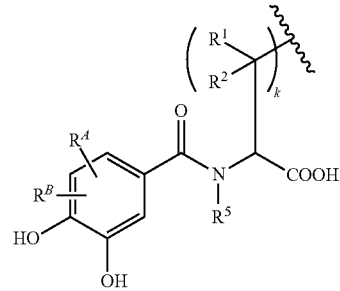

(ia)

(ib)

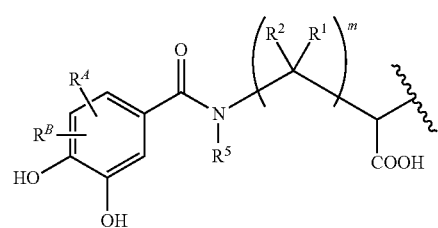

(iia)

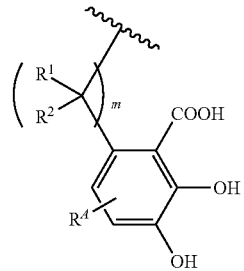

(iii)

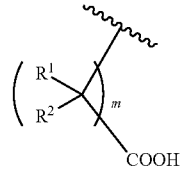

wherein, m and k are each independently an integer of 0 to 3;

$R^1$ is each independently hydrogen atom, alkyl, carboxy, or haloalkyl;

$R^2$ is each independently hydrogen atom, alkyl, carboxy, or haloalkyl;

$R^5$ is hydrogen atom, or alkyl;

$R^A$ and $R^B$ are each independently hydrogen atom, halogen atom, hydroxyl, carboxyl, alkyl, or haloalkyl;

B is a group of the following formula (v) or (vi):

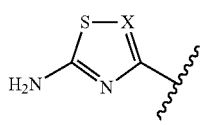

(v)

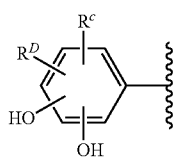

(vi)

wherein, X is —CH=, —C(—Cl)=, or —N=;

$R^C$ and $R^D$ are each independently hydrogen atom, halogen atom, hydroxyl, amino, alkyl, or haloalkyl;

E is selected from the following formula:

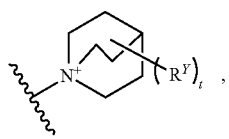

(5)

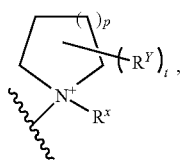

(8)

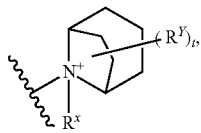

(20)

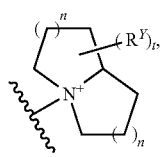

(23)

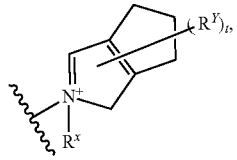

(37)

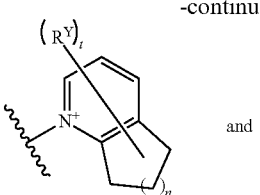

and

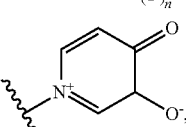

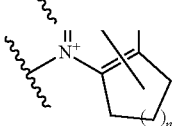

and

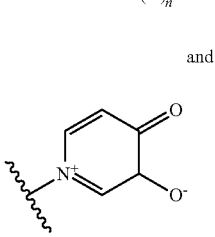

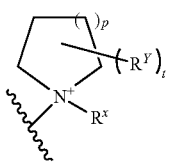

(8)

$R^X$ is substituted or unsubstituted alkyl, $R^Y$ is amino, hydroxyl, substituted or unsubstituted alkyl, and p is an integer of 1 to 3, n is an integer of 1 or 2, and t is an integer of 0 to 3, provided that when A is formula (iii), B is formula (vi), or a pharmaceutically acceptable salt thereof.

2. The compound, or a pharmaceutically acceptable salt thereof according to claim 1, wherein E is formula (5), (8), (20), (23), (39), or (40).

3. The compound, or a pharmaceutically acceptable salt thereof according to claim 1, wherein t is 0 or 1.

4. The compound, or a pharmaceutically acceptable salt thereof according to claim 1,
wherein,
$R^1$ is each independently hydrogen atom, alkyl, or carboxy; and
$R^2$ is each independently hydrogen atom, alkyl, or carboxy.

5. The compound, or a pharmaceutically acceptable salt thereof according to claim 1, wherein $R^A$ and $R^B$ are each independently hydrogen atom, halogen atom or carboxy.

6. The compound, or a pharmaceutically acceptable salt thereof according claim 1, wherein B is formula (v).

7. A pharmaceutical composition, comprising the compound or the pharmaceutically acceptable salt thereof according to claim 1.

8. A method for treating a Gram-negative bacterial infectious disease, comprising administering the compound or the pharmaceutically acceptable salt thereof according to claim 1 to a subject in need thereof.

* * * * *